(12) United States Patent
Verseck et al.

(10) Patent No.: US 7,872,100 B2
(45) Date of Patent: Jan. 18, 2011

(54) NITRILE HYDRATASES FROM METAGENOME LIBRARIES

(75) Inventors: Stefan Verseck, Hanau (DE); Klaus Liebeton, Zwingenberg (DE); Jurgen Eck, Bensheim (DE)

(73) Assignee: B.R.A.I.N. Biotechnology Research and Information Networks AG (DE)

( * ) Notice: Subject to any disclaimer, the term of this patent is extended or adjusted under 35 U.S.C. 154(b) by 328 days.

(21) Appl. No.: 10/593,357

(22) PCT Filed: Mar. 10, 2005

(86) PCT No.: PCT/EP2005/002556

§ 371 (c)(1), (2), (4) Date: Sep. 18, 2006

(87) PCT Pub. No.: WO2005/090595

PCT Pub. Date: Sep. 29, 2005

(65) Prior Publication Data

US 2008/0171389 A1    Jul. 17, 2008

(30) Foreign Application Priority Data

Mar. 20, 2004    (DE) .................. 10 2004 013 842

(51) Int. Cl.
*C07K 14/00* (2006.01)
*C07K 17/00* (2006.01)
*C07H 21/02* (2006.01)
*C07H 21/04* (2006.01)

(52) U.S. Cl. ...................................... 530/350; 930/240

(58) Field of Classification Search .................. None
See application file for complete search history.

(56) References Cited

FOREIGN PATENT DOCUMENTS

| WO | 97/12964 | 4/1997 |
|---|---|---|
| WO | 02/053774 | 7/2002 |
| WO | 02/095053 | 11/2002 |

OTHER PUBLICATIONS

GenBank Accession No. U89363.1 (Jan. 28, 2000).*
GenBank Accession No. X64360 (Feb. 26, 1993).*
Blast alignment of the alpha-subunit encoded by GenBank Accession No. U89363.1 with the alpha-subunit encoded by GenBank Accession No. X64360.*
Blast alignment of the beta-subunit encoded by GenBank Accession No. U89363.1 with the beta-subunit encoded by GenBank Accession No. X64360.*
Liebeton, K., et al., Identification and Expression in *E. coli* of Novel Nitrile Hydratases from the Metagenome, *Eng. Life Sci.*, 4(6):557-562 (2004).
Lorenz, P., et al., Metagenome—a Challenging Source of Enzyme Discovery, *Journal of Molecular Catalysis B: Enzymatic* 19-20:13-19 (2002).
Lorenz, P., et al., Screening for Novel Enzymes for Biocatalytic Processes: Accessing the Metagenome as a Resource of Novel Functional Sequence Space, *Current Opinion in Biotechnology*, 13:572-577 (2002).
Lopes Lourenco, P.M., et al., Searching for Nitrile Hydratase Using the Consensus-Degenerate Hybrid Oligonucleotide Primers Strategy, *J. Basic Microbiol.*, 44(3):203-214 (2004).
Precigou, S., et al., Rapid and Specific Identification of Nitrile Hydratase (NHase)-encoding Genes in Soil Samples by Polymerase Chain Reaction, *FEMS Microbiology Letters*, 204:155-161 (2001).
Database EMBL 'Online!, Feb. 12, 1992 "R.rhodochrous gene for L-NHHase", Database Accession No. RRLNHASE.
Database EMBL Online!, Mar. 19, 1997 "Pseudomanas Putida P38K, Amidase, Nitrile Hydratase Alpha Subunit, Nitrile Hydratase Beta Subunit, and P14K Genes, Complete Cds", Database Accession No. PPU89363.
Compton, Teresa, Degenerate Primers for DNA Amplification, PCR Protocols: A Guide to Methods and Applications, Academic Press, Inc., 1990, pp. 39-45.
Cowan, Don, et al., Biochemistry and Biotechnology of Mesophilic and Thermophilic Nitrile Metabolizing Enzymes, Extremophiles, 1998, 2:207-216.
Duran, Robert, et al., Characterization of Nitrile Hydratase Genes Cloned by DNA Screeing from *Rhodococcus erythropolis*, Biosci. Biotech. Biochem., 1993, 57:1323-1328.
Ikehata, Osamu, et al., Primary Structure of Nitrile Hydratase Deduced from the Nucleotide Sequence of a *Rhodococcus* Species and Its Expression in *Escherichia coli*, Eur. J. Biochem., 1989, 181:563-570.
Knietsch, Anja, et al., Construction and Screening of Metagenomic Libraries Derived from Enrighment Cultures: Generation of a Gene Bank for Genes Conferring Alcohol Oxidoreductase Activity on *Escherichia coli*, Applied and Environmental Microbiology, 2003, 69(3):1408-1416.
Kobayashi, Michihiko, et al., Cloning, Nucleotide Sequence and Expression in *Escherichia coli* of Two Cobalt-Containing Nitrile Hydratase Genes From *Rhodococcus rhodochrous* J1, Biochemica et Biophysica Acta, 1991, 1129:23-33.
Kobayashi, Michihiko, et al., Nitrile Hydrolases, Current Opinion in Chemical Biology, 2000, 4:95-102.
Nojiri, Masaki, et al., Functional Expression of Nitrile Hydratase in *Escherichia coli*: Requirement of a Nitrile Hydratase Activator and Post-Translational Modification of a Ligand Cysteine, J. Biochem., 1999, 125:696-704.
Rondon, Michelle R., et al., Cloning the Soil Metagenome: a Strategy for Accessing the Genetic and Functional Diversity of Uncultured Microorganisms, Applied and Environmental Microbiology, 2000, 66(6):2541-2547.
Rose, Timothy M., et al., CODEHOP (COnsensus-DEgenerate Hybrid Oligonucleotide Primer) PCR Primer Design, Nucleic Acids Research, 2003, 31(13):3763-3766.
Rose, Timothy, M., et al., Consensus-Degenerate Hybrid Oligonucleotide Primers for Amplification of Distantly Related Sequences, Nucleic Acids Research, 1998, 26(7):1628-1635.

* cited by examiner

*Primary Examiner*—Teresa E Strzelecka
(74) *Attorney, Agent, or Firm*—Pillsbury Winthrop Shaw Pittman LLP

(57) ABSTRACT

The present invention is concerned with the preparation of novel nitrile hydratases. These latter are preferably obtained from nonculturable organisms by means of a PCR-based screening, in metagenome DNA libraries, using special degenerate primers.

6 Claims, 7 Drawing Sheets

NITRILE HYDRATASES FROM METAGENOME LIBRARIES

The present invention is directed toward specific degenerate primers. These latter are preferably employed in a process for preparing nitrile hydratases. The present invention therefore also relates to the nitrile hydratases which are prepared by the process which is performed using the primers and to other proteins which are required for the nitrile hydratases to be active. The nucleic acids encoding these protein sequences, and expression systems comprising these nucleic acids, likewise form an additional part of the subject matter of the application. The use of the nitrile hydratases, and of the underlying nucleic acid sequences, constitutes an additional aspect of the present invention.

The amide and carboxylic acid structural classes are becoming ever more important as precursors of fine chemicals. Specific aminoamides and (proteinogenic and nonproteinogenic) amino acids are key intermediates for synthesizing pharmaceutical and agrochemical products as well as in the foodstuffs field. Enantiomerically pure amides and amino acids, in particular, play an ever greater role in the abovementioned areas of application.

Aminonitrile precursors, as are required for preparing the abovementioned compound classes, can be readily obtained in racemic form by way of what is termed Strecker synthesis. The nitrites which have been obtained in this way can then be converted into the corresponding amides and carboxylic acids by means of chemical or enzymic hydrolysis.

Three enzymes which are capable of being involved in the enzymic hydrolysis of nitrites are known. Nitrilases convert a nitrile function directly into the acid whereas nitrile hydratases (E.C. 4.2.1.84) in this case form the corresponding amide. This latter can then finally be converted into the corresponding carboxylic acid by means of an amidase (E.C. 3.5.1.4) (scheme 1).

Scheme 1:

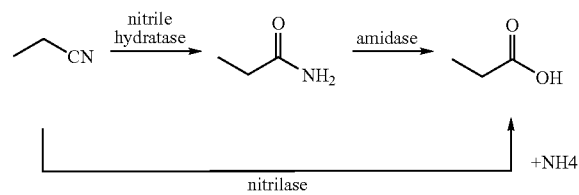

Using isolated enzymes or whole-cell catalysts to hydrolyze nitrites to give the corresponding amides and acids helps to save large quantities of salt which would otherwise accrue in the neutralization step following the chemical hydrolysis of nitrites. For this reason, the enzymic hydrolysis of nitrites to give, for example, aminoamides and/or amino acids represents a more sustainable production process.

In their active form, nitrile hydratases consist of 2 nonhomologous, α and β subunits. These latter form heterodimers and tetramers, while even decamers have been demonstrated to be present in the case of Rhodococcus rhodochrous J1. While the α and β subunits are of approximately the same size, they do not otherwise share any similarities. Nitrile hydratases are metalloproteins which contain $Fe^{3+}$ or $Co3^+$ ions (Bunch A. W. (1998), Nitriles, in: Biotechnology, Volume 8a, Biotransformations I, Chapter 6, Eds.: Rehm H J, Reed G, Wiley-VCH, p. 277-324; Shearer J, Kung I Y, Lovell S, Kaminsky W, Kovacs J A (2001) Why is there an "inert" metal center in the active site of nitrile hydratase? Reactivity and ligand dissociation from a five-coordinate Co(III) nitrile hydratase model. J Am Chem Soc 123: 463-468; Kobayashi M, Shimizu S (2000) Nitrile hydrolases. Current Opinion in Chemical Biology 4: 95-102).

One of the greatest challenges thus far has been that of heterologously preparing nitrile hydratases in a suitable host, preferably E. coli. This Gram-negative bacterium is known to express heterologous proteins at high rates. An additional advantage is the yield of biomass in high cell density fermentations using E. coli. In such fermentations, it is possible to achieve productivities of more than 100 g of dry biomass (DBM) in a period of from 24 to 44 hours (Lee S Y (1996) High cell-density culture of Escherichia coli. TIBTECH 14:98-105; Riesenberg D, Guthke R (1999) High-cell-density cultivation of microorganisms. Appl microbiol Biotechnol 51:422-430).

Most nitrile hydratase α and β subunit sequences are known from the genus Rhodococcus. However, it is precisely the nitrile hydratases from this genus which it has thus far only been possible to express in E. coli with particular difficulty (Ikehata O, Nishiyama M, Horinouchi S, Beppu T (1989) Primary structure of nitrile hydratase deduced from the nucleotide sequence of a Rhodococcus species and its expression in Escherichia coli. Eur J Biochem 181: 563-570).

The literature describes systems for expressing nitrile hydratases whose specific activities are between 4.2 and 12.2 U/mg of total protein in the case of Co-dependent nitrile hydratases from R. rhodochrous J1 (Kobayasjhi M, Nishiyama M, Nagasawa T, Horinouchi S, Beppu T, Yamada H (1991) Cloning, nucleotide sequence and expression in Escherichia coli of two cobalt-containing nitrole hydratase genes from Rhodococcus rhodochrous. Biochim Biophys Acta 1129: 23-33) and 452 U/mg of total protein in the case of an iron-dependent nitrile hydratase from Rhodococcus spec. N-771 (Njori M, Yohda M, Odaka M, Matsushita Y, Tsujimura M, Yoshida T, Dohmae N, Takio K Endo I (1999) Functional expression of Nitrile hydratases in E. coli: Requirement of a nitrile hydratase activator and a post-translational modification of a ligand cysteine. J Biochem 125: 696-704), with this corresponding to about approx. 248 U/mg of DBM (dry biomass) (calculation in accordance with Goodsell D S (1991) Inside a cell. TIBS 16: 203-206). Interestingly, it was not possible to reproduce the latter activity using nitrile hydratases from R. erythropolis, which is closely related to Rhodococcus spec. N-711, and employing similar vector systems and arrangements of the structural genes. There was, therefore, still a need for processes and systems which enable the enzymes in question to be made available in a manner which is adequate for the industrial scale.

Methods which have thus far been described for screening for nitrile hydratases have been restricted to isolating microorganisms which exhibit a corresponding enzyme activity. These microorganisms have either been taken from existing strain collections or selectively propagated in what are termed enrichment media (Colquhoun J A, Heald S C, Li L, Tamaoka J, Kato C, Horikoshi K and Bull A T (1998a) Taxonomy and biotransformation activities of some deep-sea actinomycetes. Extremophiles 2: 269-277; Colquhoun J A, Mexson J, Goodfellow M, Ward A C, Horikoshi K and Bull A T (1998b) Novel rhodococci and other mycolate actinomycetes from the deep sea. Antonie van Leeuwenhoek 74: 27-40). A disadvantage of these screening methods is that they have in the main found microorganisms of the genera Rhodococcus, Bacillus or Pseudomonas, or the like, and the diversity of the corresponding nitrile hydratases in regard to activity or substrate specificity is also limited as a consequence (Bunch A. W. (1998), Nitriles, in: Biotechnology, Volume 8a, Biotransformations I, Chapter 6, Eds.: Rehm H. J., Reed G., Wiley-VCH, p. 277-324; Cowan D, Cramp R, Pereira R, Graham D, Almathawa Q (1998) Biochemistry and biotechnology of mesophilic and thermophilic nitrile metabolising enzymes. Extremophiles 2: 207-216; Yamada H, Kobayashi M (1996) Nitrile hydratase and its application to industrial production of acrylamide. Biosci Biotechnol Biochem 60: 1391-141).

Current estimates assume that, as a rule, only 0.01-1% of the microorganisms in a habitat can be cultured and thereby made available for screening in accordance with the above-described method (Amann R I, Ludwig W, Schleifer K H (1995) Phylogenetic identification and in situ detection of individual microbial cells without cultivation. Microbiol. Rev. 59: 143-169; Pace N R (1997) A molecular view of microbial diversity and the biosphere. Science 276: 734-740; Cowan D A (2000) Microbial genomes the untapped resource. Trends Biotechnol. 18: 14-16). "Directly cloning" the genomic DNA of, if at all possible, all the organisms in a soil sample (i.e. the "metagenome"), and making this DNA available, in the form of metagenome gene libraries, for a genetic screening, is therefore increasingly gaining importance for identifying novel industrial enzymes. In this approach, the genetic screening for enzyme-encoding genes can either be effected on the basis of sequence homology, based on conserved sequence motifs, or, when suitable enzyme tests/indicator media are available, on the basis of activity homology (Lorenz P, Köhler B, Wolf M, Eck J, Zinke H (2000) Expression Cloning of Metagenome DNA from Soil. Biotechnol. 2000, Book of Abstr. Vol 2: 306).

While nitrile hydratases have already been amplified from metagenomic DNA by means of a PCR-based screening method using degenerate primers, the nature of the sequences is such that they exhibit very high degrees of similarity (90-99%) with those for known nitrile hydratases (Precigou S, Goulas P, Duran R, (2001) Rapid and specific identification of nitrile hydratase encoding genes in soil samples by polymerase chain reaction, FEMS Microbiol. Letters 204: 155-161). It is not possible to make any proper assessment of the primers which are used in this reference since the authors do not reveal the sequences of the degenerate primers or their degree of degeneracy. The high degree of similarity of the sequences to those for the *Rhodococcus rhodochrous* J1 nitrile hydratases suggests that the substrate specificity is not markedly different from that of this latter enzyme, either.

There was, therefore, still a need for processes and systems which enable additional enzymes of the type in question to be made available in a manner which is adequate for the industrial scale.

The object of the present invention was therefore to specify an additional process for preparing nitrile hydratases. In particular, the process should be able to identify nitrile hydratases which are present in what are termed nonculturable organisms. An additional object of the present invention was to prepare nitrile hydratases which are superior to those in the prior art.

These objects, and additional objects which are not specified in detail but which ensue in an obvious manner from the prior art, are achieved by the specification of specific primer constituents and their use in a process as described herein. An embodiment is drawn to a protein sequence which is required for constructing the activity of a nitrile hydratase, whereas another embodiment is drawn to a nucleic acid encoding said protein, and further, whereas another embodiment is drawn to an expression system which exhibits said nucleic acid sequence. The invention also deals with novel nitrile hydratases which have been prepared in accordance with the invention as well as their specific uses.

A prerequisite for finding novel nitrile hydratases is to specify nucleic acid sequences which are able to serve as probes for nitrile hydratase genes which are present in metagenome DNA libraries. By means of specifying degenerate primer constituents from the group consisting of

| A-01f: | gcsmrsgcstgg | (Seq. ID NO. 1) |
| B-01f: | ggsctsccscc | (Seq. ID NO. 2) |
| B-01r: | ggsggsagscc | (Seq. ID NO. 3) |
| C-01r: | ggncgcwbsgg | (Seq. ID NO. 4) |
| A-01f: | gcnmrrgcntgg | (Seq. ID NO. 5) |
| B-01f: | ggnytnccncc | (Seq. ID NO. 6) |
| B-01r: | ggnggnarncc | (Seq. ID NO. 7) |
| C-01r: | gwngwrtccca | (Seq. ID NO. 8) |
| A-01f: | gcntggrynga | (Seq. ID NO. 9) |
| B-01f: | ggnytsccncc | (Seq. ID NO. 10) |
| B-01r: | ggnggsarncc | (Seq. ID NO. 11) |
| C-01r: | swnswrtccca | (Seq. ID NO. 12) | the skilled person obtains, completely surprisingly but no less advantageously for that, special nucleic acid sequences which help to construct specific probes for screening for nitrile hydratase genes in metagenome DNA libraries. These nucleic acid sequences are degenerate sequences which, on the one hand, are specific enough for finding only nitrile hydratase genes but which, on the other hand, are so nonspecific that, if at all possible, all the nitrile hydratase genes which are present are detected. At the time of the invention, it was not possible to deduce their preparation from the prior art in an obvious manner.

The present invention accordingly also related to a process for preparing protein sequences which are required for constructing the activity of a nitrile hydratase, such that a) a metagenome DNA library of a habitat is prepared, b) this library is contacted with in each case at least one forward (f) primer and one reverse (r) primer exhibiting a degenerate nucleic acid sequence in accordance with sequences 1 to 12, c) a PCR is carried out using these primers, d) the full-length sequences of the nucleic acids encoding protein sequences which are required for constructing the activity of a nitrile hydratase are generated from the part sequences which are obtained, and e) these full-length sequences are cloned into a host organism and expressed.

As already noted at the outset, nitrile hydratases consist of at least two different subunits ($\alpha$ and $\beta$ subunits). However, further protein sequences, in addition to these two subunits, may also be required to enable the nitrile hydratases to be active. The presence of particular putative "activators" (e.g. folding proteins, etc.) may sometimes be required in order to enable the corresponding nitrile hydratases to become active. The nucleic acid sequences which encode these activators are frequently located in the immediate vicinity of the nucleic acid sequences which encode the corresponding nitrile hydratase subunits. It is consequently possible, by screening for nucleic acid sequences encoding nitrile hydratases, also at the same time to detect all the protein sequences which are required for the nitrile hydratases to be active. According to the process in accordance with the invention, the first step is that of preparing a metagenome DNA library of a particular habitat. The skilled person is familiar with the way in which this library is prepared (Knietsch, A W, Tanja; B S; Henne, A D R (2003) Metagenomes of Complex Microbial Consortia Derived from Different Soils as Sources for Novel Genes Conferring Formation of Carbonyls from Short-Chain Polyols on *Escherichia coli*. Journal of Molecular Microbiology and Biotechnology 5(1): 46-56; Rondon, M R; August, P R; Bettermann A D; Brady, S F; Grossman, T H; Liles, M R; Loiacono, K A; Lynch, B A; MacNeil, I A; Mino, r C; Tiong, C L; Gilman, M; Osburne, M S; Clardy, J; Handelsman, J; Goodman, R M (2000) Cloning the soil metagenome: a strategy for accessing the genetic and functional diversity of uncultured microorganisms. Applied and environmental microbiology 66(6):2541-7). Primers which exhibit the degenerate nucleic acid sequences according to the invention (Seq. ID Nos. 1-12) are then added to this library. A PC reaction is subsequently carried out, with this reaction giving rise to part sequences of the nucleic acid sequences encoding nitrile hydratase subunits. Employing methods of the prior art, the skilled person can then use these part sequences to identify the corresponding full-length nucleic acid sequences (Schloss, P D; Handelsman, J (2003) Biotechnological prospects from metagenomics. Current Opinion in Biotechnology, 14(3): 303-310; Rondon, M R; August, P R; Bettermann A D; Brady, S F; Grossman, T H; Liles, M R; Loiacono, K A; Lynch, B A; MacNeil, I A; Mino, r C; Tiong, C L; Gilman, M; Osburne, M S; Clardy, J; Handelsman, J; Goodman, R M (2000) Cloning the soil metagenome: a strategy for accessing the genetic and functional diversity of uncultured microorganisms. Applied and environmental microbiology 66(6):2541-7). Finally, the nucleic acid sequences which have been found are recombinantly prepared in particular expression systems. The methods for doing this are likewise known to the skilled person (lit. see above).

In a preferred embodiment, the degenerate nucleic acid sequences according to the invention (Seq. ID Nos. 1-12) are employed in the present process such that in each case 3-0 primer pairs composed of primers exhibiting the nucleic acid sequences A-01f (Seq. ID Nos. 1, 5 and 9) and B-01r (Seq. ID Nos. 3, 7 and 11) or C-01r (Seq. ID Nos. 4, 8 and 12) and also B-01f (Seq. ID Nos. 2, 6 and 10) and C-01r (Seq. ID Nos. 4, 8 and 12) are used in the PCR. When these combinations are employed, the nucleic acid sequences encoding the protein sequences which are required for nitrile hydratase activity are detected in a preferred and efficient manner.

Preference is furthermore given to locating certain other nucleic acid sequences (e.g. "stabilizing regions") upstream of the above-described degenerate primer constituents (Kwok S, Chang S Y, Sninsky J J, Wang A, 1995, "Design and use of mismatched and degenerate primers" In: "PCR Primer, A laboratory Manual" Dieffenbach C W & Dveksler G S (Editors), Cold Spring Harbor Laboratory Press, pp 143-155; Compton T, 1990, "Degenerate Primers for DNA Amplification" In: "PCR Protocols, A Guide to Methods and Applications", Innis M A, Gelfand D H, Sninsky J J, White T J (Editors) Academic Press, San Diego, pp 39-45). In this case, the primers employed in the PC reaction consist of degenerate nucleic acid sequences of the above-described type (sequences ID Nos. 1 to 12) and the nucleic acid sequences mentioned in the sequences having the ID Nos. 13 to 23. Very particular preference is given, therefore, to a process in which nucleic acid sequences selected from the group consisting of:

| | |
|---|---|
| GCCAAGGTCGTC | (Seq. ID NO. 13) |
| GGCCGGTCCTG | (Seq. ID NO. 14) |
| TCCTTGTACCAGGTC | (Seq. ID NO. 15) |
| GCCCGCC | (Seq. ID NO. 16) |
| GGCGCTAATGTTGTT | (Seq. ID NO. 17) |
| TGGCCGGTTCTG | (Seq. ID NO. 18) |
| CAAATTCTTTATACCAAGTC | (Seq. ID NO. 19) |
| CCATATATCGCATTTCAGCT | (Seq. ID NO. 20) |
| GGTCGTGGCCAAG | (Seq. ID NO. 21) |
| GGCCGGTCCTG | (Seq. ID NO. 22) |
| TCCTTGTACCAGGTC | (Seq. ID NO. 23) |
| GCGCATTTCGGCG | (Seq. ID NO. | are placed upstream of the degenerate nucleic acid sequences (Seq. ID Nos. 1-12). These upstream sequences are likewise derived from conserved nitrile hydratase regions and adapted to the codon usage of organisms having a different GC content.

A process as described at the outset, in which use is made of primers which are selected from the group consisting of

| | |
|---|---|
| GCCAAGGTCGTCgcsmrsgcstgg | (Seq. ID NO. 25) |
| GGCCGGTCCTGggsctsccscc | (Seq. ID NO. 26) |
| TCCTTGTACCAGGTCggsggsagscc | (Seq. ID NO. 27) |
| GCCCGCCggncgcwbsgg | (Seq. ID NO. 28) |
| GGCGCTAAAGTTGTTgcnmrrgcntgg | (Seq. ID NO. 29) |
| TGGCCGGTTCTGggnytnccncc | (Seq. ID NO. 30) |
| CAAATTCTTTATACCAAGTCggnggnarncc | (Seq. ID NO. 31) |
| CCATATATCGCATTTCAGCTgwngwrtccca | (Seq. ID NO. 32) |
| GGTCGTGGCCAAGgcntggrynga | (Seq. ID NO. 33) |
| GGCCGGTCCTGggnytsccncc | (Seq. ID NO. 34) |
| TCCTTGTACCAGGTCggnggsarncc | (Seq. ID NO. 35) |
| GCGCATTTCGGCGswnswrtccca | (Seq. ID NO. 36) | is therefore very particularly advantageous.

Using these primers, it was possible to detect nucleic acid sequences encoding nitrile hydratases, as well as other genes for putative "activators", in metagenome DNA libraries.

Accordingly, a next part of the subject matter of the present invention is constituted by the protein sequences which are required for constructing the activity of a nitrile hydratase, with these sequences possessing less than 100% homology, preferably less than 97%, more preferably less than 96%, even more preferably less than 95%, yet more preferably less than 90%, very preferably less than 85%, and extremely preferably less than 80%, homology, at the amino acid level, with such known protein sequences, and with the nucleic acid sequences encoding them being generated from part sequences which give a positive hybridization signal, under stringent conditions, with the primers according to the invention exhibiting the nucleic acid sequences having the sequences ID Nos. 1 to 12.

The positive hybridization is a prerequisite for it to be possible to find corresponding nucleic acid sequences using the PC reaction-based screening. Methods with which the skilled person is familiar can then be used to obtain the corresponding recombinant protein sequences from these nucleic acid sequences.

These recombinant techniques are used to obtain organisms which are able to provide the protein sequence in question in a quantity which is adequate for an industrial process. The rec-protein sequences according to the invention are prepared using recombinant DNA methods which are known to the skilled person (Sambrook, J.; Fritsch, E. F. and Maniatis, T. (1989), Molecular cloning: a laboratory manual, $2^{nd}$ ed., Cold Spring Harbor Laboratory Press, New York; Balbas, P. and Bolivar, F. (1990), Design and construction of expression plasmid vectors in *E. coli*, Methods Enzymol. 185, 14-37; Rodriguez, R. L. and Denhardt, D. T (eds) (1988), Vectors: a survey of molecular cloning vectors and their uses, 205-225, Butterworth, Stoneham). With regard to the general procedure (PCR, cloning, expression, etc.), the reader may be referred to the following literature and the references cited therein: Universal GenomeWalker™ Kit User Manual, Clontech, 3/2000, and the literature cited therein; Triglia T.; Peterson, M. G. and Kemp, D. J. (1988), A procedure for in vitro amplification of DNA segments that lie outside the boundaries of known sequences, Nucleic Acids Res. 16, 8186; Sambrook, J.; Fritsch, E. F. and Maniatis, T. (1989), Molecular cloning: a laboratory manual, $2^{nd}$ ed., Cold Spring Harbor Laboratory Press, New York; Rodriguez, R. L. and Denhardt, D. T (eds) (1988), Vectors: a survey of molecular cloning vectors and their uses, Butterworth, Stoneham.

The corresponding nucleic acid sequences, which encode the protein sequences which have just been described, also constitute a next part of the present invention. These nucleic acid sequences are therefore all those which, within the bounds of the degeneracy of the genetic code, encode the same protein sequence. This consequently likewise also encompasses those nucleic acid sequences which possess, at the nucleic acid level, a homology with the nucleic acid sequences found in accordance with the invention of at least 70 percent, or corresponding fragments of these nucleic acid sequences, which in turn encode protein sequences which are involved in constructing the activity of a nitrile hydratase. Preference is given to these nucleic acid sequences encoding protein sequences which are improved as compared with the protein sequences found in accordance with the invention.

Examples of nucleic acid sequences according to the invention are those of the odd-numbered Seq. ID Nos. 37 to 85. It is possible, as described above, to use the nucleic acid sequences which have been found to obtain the protein sequences according to the invention in high yields from rapidly growing host organisms, e.g. *E. coli*.

This takes place by incorporating (cloning) the nucleic acid sequences according to the invention into special expression systems which can be used to obtain the corresponding protein sequences recombinantly from preferred host organisms. A next aspect of the present invention is therefore constituted by a (artificially prepared) expression system which exhibits one or more of the nucleic acid sequences according to the invention. In principle, all the systems which are familiar to the skilled person for this purpose are suitable for use as the expression system. These systems are preferably plasmids or vectors and microorganisms.

In principle, all the embodiments which are available to the skilled person for this purpose are suitable for use as plasmids or vectors. These plasmids and vectors can be found, for example, in Studier and coworkers (Studier, W. F.; Rosenberg A. H.; Dunn J. J.; Dubendroff J. W.; (1990), Use of the T7 RNA polymerase to direct expression of cloned genes, Methods Enzymol. 185, 61-89) or in the brochures supplied by the companies Novagen, Promega, New England Biolabs, Clontech or Gibco BRL. Other preferred plasmids and vectors can be found in: Glover, D. M. (1985), DNA cloning: a practical approach, Vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, $2^{nd}$ ed., Cold Spring Harbor Laboratory Press, New York.

Plasmids which can very preferably be used to clone the construct containing the nucleic acid sequences according to the invention into the host organism are: pUC18 (Roche Biochemicals), pKK-177-3H (Roche Biochemicals), pBTac2 (Roche Biochemicals), pKK223-3 (Amersham Pharmacia Biotech), pKK-233-3 (Stratagene) or pET (Novagen). Extreme preference is given to plasmids of the pET series.

As has been said, the recombinant microorganism into which the plasmids or vectors which contain the nucleic acid sequences according to the invention are cloned is used for replicating and isolating an adequate quantity of the recombinant protein sequence. The methods for doing this are well known to the skilled person (Sambrook, J.; Fritsch, E. F. and Maniatis, T. (1989), Molecular cloning: a laboratory manual, $2^{nd}$ ed., Cold Spring Harbor Laboratory Press, New York). In principle, the microorganisms which are used can be any organisms which the skilled person takes into consideration for this purpose, for example yeasts, such as *Hansenula polymorpha, Pichia* sp., *Saccharomyces cerevisiae*, prokaryotes, such as *E. coli* or *Bacillus subtilis*, or eukaryotes, such as mammalian cells, insect cells or plant cells. Preference is given to using *E. coli* strains for this purpose. The following are very particularly preferred: *E. coli* XL1 Blue, NM 522, JM101, JM109, JM105, RR1, DH5α, TOP 10⁻ or HB101, BL21, BL21 (DE3), or BL21 (DE3) codon plus RIL.

Furthermore, the nucleic acid sequences which are in accordance with the invention (uneven-numbered Seq. ID Nos. 37 to 85) and which are additionally further improved, and which encode the protein sequences which are required for constructing the activity of a nitrile hydratase, are preferably suitable for preparing what are termed whole-cell catalysts. In principle, whole-cell catalysts of this type are recombinant microorganisms such as those which have just been mentioned. However, in addition to the cloned genes encoding a nitrile hydratase, these whole-cell catalysts also comprise additional enzymes which are required for decomposing nitrites into acids. As explained at the outset, these enzymes are enzymes which exhibit amidase activity.

For this reason, whole-cell catalysts which comprise at least one cloned gene for a protein sequence possessing (D- or L-)amidase activity and cloned genes encoding an active nitrile hydratase are also regarded as being recombinant microorganisms of the abovementioned type. Optionally, the whole-cell catalyst can comprise additional nucleic acid sequences which encode enzymes which are advantageous for decomposing a nitrile function into an acid function. These enzymes are, in particular, enzymes which are selected from the group of protein sequences possessing α-aminonitrile racemase activity, possessing cyanohydrin racemase activity, possessing α-hydroxycarboxylic acid racemase activity or possessing (α- or β-)-amino acid amide racemase activity.

In addition to producing the protein sequences according to the invention, which are required for constructing a nitrile hydratase activity, the whole-cell catalyst according to the invention preferably produces a protein sequence possessing L-amidase activity from *rhizobium*, preferably *R. huautlense* DSM 14983 (WO2004/005517) or possessing D-amidase activity, e.g. that from *Variovorax* (EP 1318193).

Corresponding racemases are known, for example, from *Pseudomonas putida* and *Rhodococcus* sp. (Godtfredsen, S. E.; Clausen, K.; Ingvorsen, K.; Hermes, H. F.; Van Balken, J. A.; Meijer, E. M. (1989, EP 0 307 023; WO 8 901 525). Other amino acid amide racemases have been described in *Klebsiella oxytoca* by Hermes and coworkers (Hermes, H. F. M.; Peeters, W. P.; Peters, P. J. (1990), EP 0 383 403), as well as in *Agrobacterium rhizogenes* and *Ochrobacterium anthropi* (Boesten, W. H. J.; Raemakers-Franken, P. C.; Sonke, T.; Euverink, G. J. W.; WO 03106691). The advantage of using corresponding racemases is based on the fact that 100% of a racemic nitrile can be converted into the corresponding enantiomerically enriched acid.

An organism which is mentioned in DE10155928 as being a host organism is preferably used as whole-cell catalyst. The advantage of such an organism is that several enzyme systems are expressed simultaneously, which means that it is only necessary to grow one rec-organism for reacting a readily preparable nitrile or cyanohydrin or α-aminonitrile to give the corresponding enantiomerically enriched acid. In order to adjust the expression of the nucleic acid sequences in question with regard to the turnover rates of the protein sequences (enzymes) which they encode, the corresponding nucleic acid sequences can be installed on different plasmids possessing different copy numbers and/or promoters of differing strength can be used so as to ensure that the nucleic acid sequences are expressed at different strengths. In enzyme systems which have been adjusted in this way, there is, advantageously, no accumulation of an intermediate compound, which might possibly have an inhibitory effect, and the reaction under consideration can take place at an optimal overall rate. However, this is sufficiently well known to the skilled person (Gellissen, G.; Piontek, M.; Dahlems, U.; Jenzelewski, V.; Gavagan, J. W.; DiCosimo, R.; Anton, D. L.; Janowicz, Z. A. (1996), Recombinant *Hansenula polymorpha* as a biocatalyst. Co-expression of the spinach glycolate oxidase (GO) and the *S. cerevisiae* catalase T (CTT1) gene, Appl. Microbiol. Biotechnol. 46, 46-54; Farwick, M.; London, M.; Dohmen, J.; Dahlems, U.; Gellissen, G.; Strasser, A. W.; DE19920712).

It is consequently possible to use the present process to prepare the α and β subunits of nitrile hydratases using metagenome DNA libraries as the starting material. Accordingly, another part of the subject matter of the present invention is constituted by the nitrile hydratases which exhibit the protein sequences according to the invention for nitrile hydratase α subunits and β subunits and which can be prepared from the nucleic acid sequences which are made available by this process and which encode the α and β subunits according to the invention. As is demonstrated in the examples, active nitrile hydratases are also formed, in this connection, when any arbitrary α subunits are combined with any arbitrary β subunits. This thereby makes it possible to increase still further the diversity of possible nitrile hydratases.

Other parts of the subject matter of the present invention relate to the use of the nucleic acid sequences which are prepared by the process according to the invention for producing improved protein sequences which are required for constructing the activity of a nitrile hydratase. The way in which the skilled person proceeds when improving protein sequences on the basis of altering nucleic acid sequences is well known. In general, this is effected by using methods of mutagenesis. Any methods which are available to the skilled person for this purpose are suitable for being used as mutagenesis methods. In particular, these methods are saturation mutagenesis, random mutagenesis, in-vitro recombination methods and site-directed mutagenesis (Eigen, M. and Gardiner, W. (1984), Evolutionary molecular engineering based on RNA replication, Pure Appl. Chem. 56, 967-978; Chen, K. and Arnold, F. (1991), Enzyme engineering for nonaqueous solvents: random mutagenesis to enhance activity of subtilisin E in polar organic media. Bio/Technology 9, 1073-1077; Horwitz, M. and Loeb, L. (1986), Promoters Selected From Random DNA-Sequences, Proc Natl Acad Sci USA 83, 7405-7409; Dube, D. and L. Loeb (1989), Mutants Generated By The Insertion Of Random Oligonucleotides Into The Active-Site Of The Beta-Lactamase Gene, Biochemistry 28, 5703-5707; Stemmer, P. C. (1994), Rapid evolution of a protein in vitro by DNA shuffling, Nature 370, 389-391 and Stemmer, P. C. (1994), DNA shuffling by random fragmentation and reassembly: In vitro recombination for molecular evolution. Proc Natl Acad Sci USA 91, 10747-10751).

The novel nucleic acid sequences which are obtained in this way are cloned into a host organism, and expressed, using the above-described methods, and the protein sequences which have been prepared in this way are detected by means of suitable screening methods and then isolated. In principle, any detection reactions which are possible for the molecules which are formed are suitable for the detection. Nitrile hydratase activities can be detected in a coupled enzymic test using amidases, with ammonium being formed as a by product. In principle, any possible reactions for detecting ammonia or ammonium ions, such as Nessler reagent (Vogel, A., I., (1989) Vogel's textbook of quantitative chemical analysis, John Wiley & Sons, Inc., $5^{th}$ ed., 679-698, New York), the indophenol reaction, also termed Berthelot's reaction (Wagner, R., (1969) Neue Aspekte zur Stickstoffanalytik in der Wasserchemie, Vom Wasser, [Novel aspects of nitrogen analysis in water chemistry, about water] VCH-Verlag, vol. 36, 263-318, Weinheim), in particular the enzymic determination using glutamate dehydrogenase (Bergmeyer, H., U., and Beutler, H. O. (1985) Ammonia, in: Methods of Enzymatic Analysis, VCH-Verlag, $3^{rd}$ Edition, Vol. 8: 454-461, Weinheim), or else detection using ammonium-sensitive electrodes, are suitable for detecting it. Furthermore, HPLC methods are used for detecting amino acids, for example a derivative method based on o-phthaldialdehyde and N-isobutyryl-cysteine for enantiomerically separating amino acids (Brückner, H., Wittner R., and Godel H., (1991) Fully automated high-performance liquid chromatographic separation of DL-amino acids derivatized with o-Phthaldialdehyde together with N-isopropyl-cysteine. Application to food samples, Anal. Biochem. 144, 204-206). The amide which is directly formed by the nitrile hydratase reaction can likewise be detected using HPLC methods (e.g. reverse phase).

In a last embodiment of the present invention, the latter relates to the use of the nitrile hydratases according to the invention for preparing organic acid amides and acids, in particular enantiomerically enriched α-hydroxy acids or α-amino acids.

For this application, the nitrile hydratase in question can be used in free form, as a homogeneously purified compound or as a recombinantly prepared enzyme. Furthermore, the enzyme can also be employed as a constituent of an intact host organism or in combination with the disrupted, and, if desired, highly purified, cell mass of the host organism. It is likewise possible to use the enzyme in immobilized form (Sharma B. P.; Bailey L. F. and Messing R. A. (1982), Immobilisierte Biomaterialiern—Techniken und Anwendungen [Immobilized biomaterials—techniques and applications], Angew. Chem. 94, 836-852). The immobilization is advantageously effected by means of lyophilization (Paradkar, V. M.; Dordick, J. S. (1994), Aqueous-Like Activity of α-Chymotrypsin Dissolved in Nearly Anhydrous Organic Solvents, J. Am. Chem. Soc. 116, 5009-5010; Mori, T.; Okahata, Y. (1997), A variety of lipi-coated glycoside hydrolases as effective glycosyl transfer catalysts in homogeneous organic solvents, *Tetrahedron Lett.* 38, 1971-1974; Otamiri, M.; Adlercreutz, P.; Matthiasson, B. (1992), Complex formation between chymotrypsin and ethyl cellulose as a means to solubilize the enzyme in active form in toluene, Biocatalysis 6, 291-305). Very particular preference is given to lyophilization in the presence of surface-active substances such as Aerosol OT or polyvinylpyrrolidone or polyethylene glycol (PEG) or Brij 52 (diethylene glycol monocetyl ether) (Kamiya, N.; Okazaki, S.-Y.; Goto, M. (1997), Surfactant-horseradish peroxidase complex catalytically active in anhydrous benzene, Biotechnol. Tech. 11, 375-378).

Greatest preference is given to immobilization on Eupergit®, in particular Eupergit C® and Eupergit 250L® (Röhm) (Eupergit® C, a carrier for immobilization of enzymes of industrial potential. Katchalski-Katzir, E.; Kraemer, D. M. Journal of Molecular Catalysis B: Enzymatic (2000), 10(1-3), 157-176).

Preference is also given to immobilization on Ni-NTA in combination with the polypeptide being provided with a His tag (hexahistidine) (Purification of proteins using polyhistidine affinity tags. Bornhorst, Joshua A.; Falke, Joseph J. Methods in Enzymology (2000), 326, 245-254).

It is likewise possible to conceive of using the polypeptides as CLECs (St. Clair, N.; Wang, Y.-F.; Margolin, A. L. (2000), Cofactor-bound cross-linked enzyme crystals (CLEC) of alcohol dehydrogenase, Angew. Chem. Int. Ed. 39, 380-383).

By using these procedures, it is possible to successfully generate polypeptides which are able to function in mixtures of aqueous and organic solvents, or in media which are entirely organic, from polypeptides which are rendered unstable by organic solvents.

The present invention describes the isolation of nitrile hydratases and their corresponding genes by using molecular genetic methods to tap the uncultured microbial diversity of different habitats. Using degenerate primers in connection with the PCR-based screening of metagenome DNA libraries identifies nitrile hydratase genes and elucidates the part sequences of the PCR products which are obtained in this way. In a subsequent step, the complete DNA sequences of the genes are determined in order, after cloning and heterologous expression, to provide enzyme samples for activity profiling and investigating applications.

By means of rationally selecting soil samples, which might possibly contain nitrites, for preparing metagenome libraries (metagenome DNA libraries) and focusing on application-relevant substrates within the context of enrichment cultures, it is possible to enrich nitrile-converting microorganisms. In any case, the genetic screening in metagenome libraries provides a pool of corresponding nitrile hydratase genes for subsequent expression, which pool can, however, also serve as the basis for enzyme optimization by means of directional evolution.

Metagenome libraries which were prepared from four different habitats and sites (grassland, forest, sandy ecosystem and biofilm), and which contained more than 83 000 clones, were screened for identifying novel nitrile hydratases. The skilled person is familiar with the construction of such metagenome libraries (Schloss, P D; Handelsman, J (2003) Biotechnological prospects from metagenomics. Current Opinion in Biotechnology, 14(3): 303-310; Knietsch, A W, Tanja; B S; Henne, A D R (2003) Metagenomes of Complex Microbial Consortia Derived from Different Soils as Sources for Novel Genes Conferring Formation of Carbonyls from Short-Chain Polyols on *Escherichia coli*. Journal of Molecular Microbiology and Biotechnology 5(1): 46-56; Rondon, M R; August, P R; Bettermann A D; Brady, S F; Grossman, T H; Liles, M R; Loiacono, K A; Lynch, B A; MacNeil, I A; Mino, r C; Tiong, C L; Gilman, M; Osburne, M S; Clardy, J; Handelsman, J; Goodman, R M (2000) Cloning the soil metagenome: a strategy for accessing the genetic and functional diversity of uncultured microorganisms. Applied and environmental microbiology 666): 2541-7). These clones together contain about 3000 MBp of DNA. The metagenome DNA libraries were screened for novel nitrile hydratases by means of a PCR screening which used degenerate oligonucleotides which were derived from conserved primary structural motifs of known nitrile hydratases. The degenerate primers employed were those depicted in sequence ID Nos. 25 to 36.

In this connection, the primers having the primer constituent A-01f can, in particular, in each case be combined with those having the primer constituents B-01r (size of the PCR product to be expected, approx. 210 bp) or C-01r (size of the PCR product to be expected, approx. 350 bp), while the primers having the primer constituent B-01f can be combined with those having the primer constituent C-01r (size of the PCR product to be expected, approx. 180 bp). In particular, the degenerate "core" part of the primers (underlined in sequence ID Nos. 25 to 36) is important for identifying novel nitrile hydratases while the nondegenerate segment can be varied.

The corresponding PC reaction can be carried out using known methods. When special polymerases are used, the PCR must be amended in accordance with the manufacturer's instructions.

It was possible to identify clones carrying genes for nitrile hydratases in all 5 of the metagenome libraries. The skilled person is familiar with methods for using the part sequences of the nitrile hydratase genes for identifying the gene-carrying clone and elucidating the full-length sequence (Schloss, P D; Handelsman, J (2003) Biotechnological prospects from metagenomics. Current Opinion in Biotechnology, 14(3): 303-310; Duran, R; Nishiyama, M; Horinouchi, S; Beppy, T (1993) Characterization of nitrile hydratase genes cloned by DNA screening from *Rhodococcus erythropolis*. Biosci Biotech Biochem 57(8): 1323-1328).

It was thus possible to determine the full-length sequences (nucleic acid sequences) of a total of 12 genes encoding α subunits and a total of 10 genes encoding β subunits (FIG. 1). The sequences of three genes which could encode putative nitrile hydratase "activators" were also determined.

In order to prepare the nitrile hydratases, the genes encoding the α and β subunits were in each case placed separately under the control of the phage T7 gene 10 promoter. The vectors pET22b and, respectively, pET26b (Novagen, CN Bioscience, Inc.) were used for this purpose (FIGS. 5 and 6). Using a two-vector expression system made it possible to simply combine the nitrile hydratase subunits from different enzymes. Corresponding constructs were expressed in *E. coli* strain BL21 (DE3) CodonPlus RIL (Novagen, CN Bioscience, Inc.). The cells were incubated at 26° C. using LB medium and induced with 0.5 mM IPTG on reaching a cell density of O.D.580=1.0. It was possible to deal with the problem, which occasionally arose, of protein aggregation following overexpression at 37° C. by reducing the temperature down to 26° C. Coexpressing various chaperones (trigger factor, GroEL/GroES and Dnak/DnaJ/GrpE) did not, at 26° C., show any additional effect which went beyond that achieved by reducing the temperature.

The yields with regard to activity against benzonitrile varied considerably (FIG. 2) with it not being possible to demonstrate any clear correlation between the protein quantity which was prepared and the activity which was produced. Thus, at 30 U/g of DBM, the yield in the case of the clone containing the nitrile hydratase M49bD9 (Seq. ID No. 49/71) was relatively high even though it was not possible to detect any proteins for the nitrile hydratase in the SDS-PAGE analysis. This contrasts with the clone M12K24 (Seq. ID No. 39/63), which was determined to have an activity of about 2.5 U/g of DBM even though it was possible to overexpress both subunits relatively strongly and a substantial proportion could be found in the soluble fraction. The magnitude of the activity consequently depends to a high degree on the particular enzyme in question.

In the case of a variety of nitrile hydratases, an additional small open reading frame, which encodes a protein sequence which appears to be involved in activating the nitrile hydratase, was identified in the immediate vicinity of the genes for the subunits of the enzyme. These proteins were designated P12K (Seq. ID No. 81/83) or P14K (Seq. ID No. 85) since their molecular weight was about 12 or 14 kDa. While it was possible to prepare some nitrile hydratases in active form even without these P12K homologs, the presence of these proteins was essential for other nitrile hydratases to be expressed in active form. In order to investigate the influence of P12K homologs, whose genes were also found in three metagenome clones, on the expression of the corresponding nitrile hydratases, and also on that of nitrile hydratases from other clones, two of these genes were cloned into the vector pBBR1MCS5 (Kovach et al., 1995, Four new derivatives of the broad host range cloning vector pBBR1MCS, carrying different antibiotic-resistance cassettes, Gene 166: 175-176) and, in this vector, placed under the control of the lac promoter. The corresponding constructs were designated pBBR5—P12K-M49bD9 and pBBR5—P12K-M3aG10 (FIGS. 6 and 7).

The nitrile hydratase genes M49bD9 (Seq. ID No. 49/71) and M3aG10 (Seq. ID No. 57/79) were expressed in the presence of the corresponding P12K homologs (Seq. ID No. 83—M49bD9; Seq. ID No. 85—M3aG10) at 26° C. in *E. coli* strain BL21 CodonPlus RIL. In both cases, it was possible to markedly overexpress the subunits of the nitrile hydratases.

The presence of the P12K homolog (Seq. ID No. 83) increased the activity of the clone M49bD9 nitrile hydratases (Seq. ID No. 49/71) by about a factor of 27, up to approx. 830 U/g of DBM (table 1). In the case of the clone M3aG10 enzyme (Seq. ID No. 57/79), it was possible to detect activity (approx. 23 U/g of DBM) for the first time under these conditions. These results verify that the presence of the P12K homologs (Seq. ID No. 85) can be crucial for increasing the activity yield.

TABLE 1

Activity of nitrile hydratases following coexpression with P12K homologs (Seq. ID Nos. 83 and 85)

| Clone | Without P12K | With P12K |
| --- | --- | --- |
| M49bD9 (α, β) | 30 U/g of DBM | 826 U/g of DBM |
| M3aG10 | 0 U/g of DBM | 23 U/g of DBM |

Combining subunits from different metagenome clones opens up the possibility of generating nitrile hydratases which possess potentially novel substrate specificities. By combining α subunits with different β subunits, it would be possible to generate a great diversity of combinations of novel nitrile hydratases. Such a combination of subunits from unrelated nitrile hydratases has not thus far been disclosed in the literature.

In order to evaluate this possibility, the α subunits of clones M73dC9 and M15aA6 (Seq. ID Nos. 59 and 45), for which it was not possible to find any α subunits, were expressed with the β subunit of clone M12K24 (Seq. ID No. 63) in *E. coli* strain BL21 codon plus RIL.

Whereas both subunits could be expressed at approximately equal strengths when the a-M73dC9a/b-M12K24 (Seq. ID Nos. 59 and 63) pair was expressed, the α subunit of clone M15aA6 (Seq. ID No. 45) appears to have been expressed more strongly than does the β subunit of clone M12K24 (Seq. ID No. 63).

Combining the α subunit of clone M73dC9 (Seq. ID No. 59) and the β subunit of clone M12K24 (Seq. ID No. 63) surprisingly led to the formation of an active nitrile hydratase having an activity of approx. 0.07 U/g of DBM (FIG. 3). This result verifies that it is in principle possible to prepare active enzymes by combining nitrile hydratase subunits from different clones. At the time of the invention, it was not possible to deduce this, as such, from the prior art.

Stringent conditions: in this present document, the expression "under stringent conditions" is understood as described in Sambrook et al. (Sambrook, J.; Fritsch, E. F. and Maniatis, T. (1989), Molecular cloning: a laboratory manual, $2^{nd}$ ed., Cold Spring Harbor Laboratory Press, New York). A stringent hybridization in accordance with the present invention preferably exists when a positive hybridization signal is still observed after washing for 1 hour with 1×SSC (150 mM sodium chloride, 15 mM sodium citrate, pH 7.0) and 0.1% SDS (sodium dodecyl sulfate) at 50° C., preferably at 55° C., more preferably at 62° C. and most preferably at 68° C., and more preferably for 1 hour with 0.2×SSC and 0.1% SDS at 50° C., more preferably at 55° C., yet more preferably at 62° C. and most preferably at 68° C.

Within the context of the invention, optically enriched (enantiomerically enriched, enantiomer enriched) compounds are understood as meaning the presence of one optical antipode at >50 mol % in a mixture with the other antipode. All types of single-stranded DNA, and DNA which is complementary thereto or double-stranded DNA (e.g. genomic DNA or cDNA), as well as RNA (e.g. mRNA), or mixtures thereof, are subsumed under the term nucleic acid sequences.

Improved nucleic acid sequences encode improved protein sequences. Improved protein sequences are those which exhibit an improvement, as compared with the original sequences, in regard to activity and/or selectivity and/or stability. According to the invention, this means that the proteins are more active and/or more selective or less selective, or are more stable under the reaction conditions employed. While the activity and the stability of the proteins should naturally be as high as possible for the industrial application, an improvement with regard to selectivity is said to have taken place when the substrate selectivity decreases but the enantioselectivity of the proteins is increased. This also applies to proteins as constituents of nitrile hydratases insofar as they help to confer the corresponding improved properties on the enzyme.

According to the invention, the claimed protein sequences and nucleic acid sequences also encompass those sequences which exhibit a homology (excluding the natural degeneracy) which is greater than 70% (with regard to the nucleic acid sequence) or 80% (with regard to the protein sequences), preferably greater than 90%, 91%, 92%, 93% or 94%, more preferably greater than 95% or 96% and particularly preferably greater than 97%, 98% or 99%, with one of these sequences, provided the mode of action or purpose of such a sequence is preserved. The expression "homology" (or identity), as used herein, can be defined by the equation H (%)= $[1-V/X] \times 100$, in which H denotes homology, X is the total number of nucleobases/amino acids in the comparison sequence and V is the number of different nucleobases/amino acids in the sequence to be considered, based on the comparison sequence. In any case, the term nucleic acid sequences which encode polypeptides encompasses all the sequences which appear possible in accordance with the degeneracy of the genetic code.

EXPERIMENTAL SECTION

General PCR Protocol

Culturing Microorganisms

Figure 1:
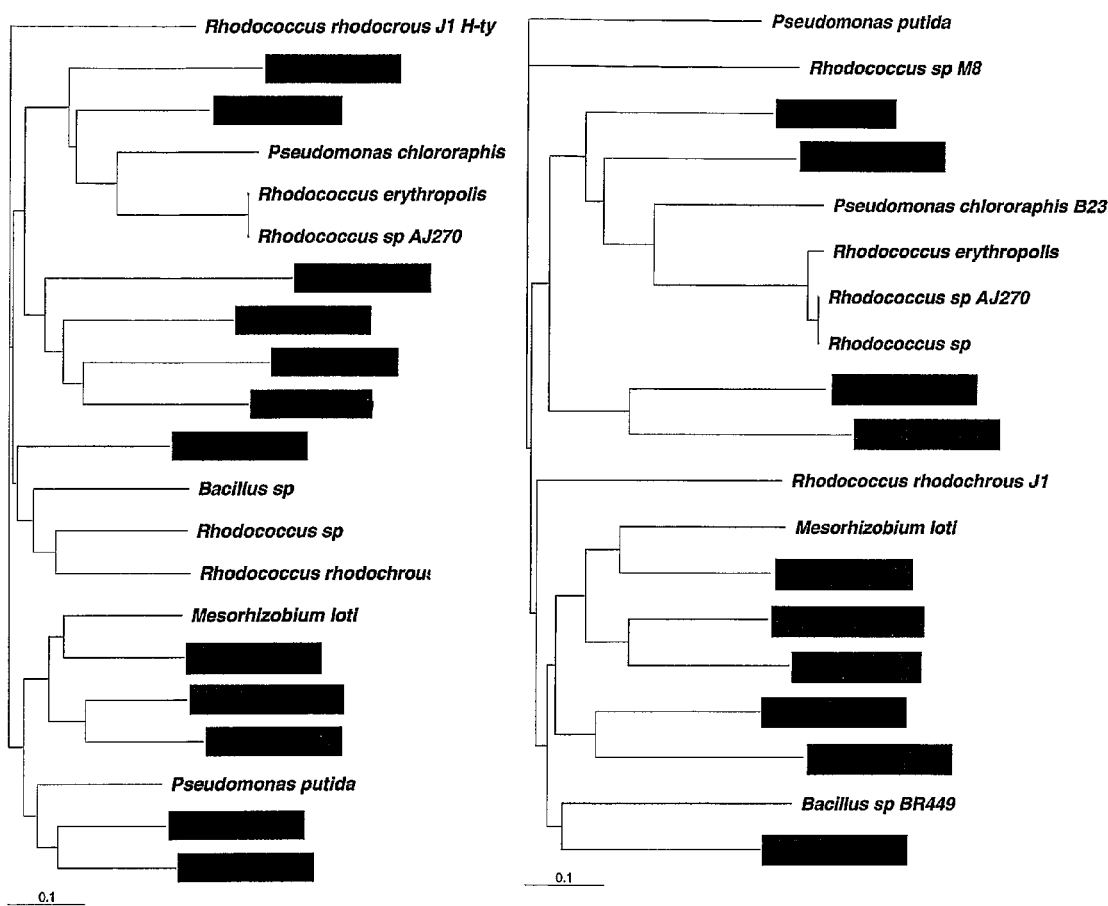
FIG. 1: Homology among the nitrile hydratase α and β subunits which were found by means of a genetic screening.
Figure 2:
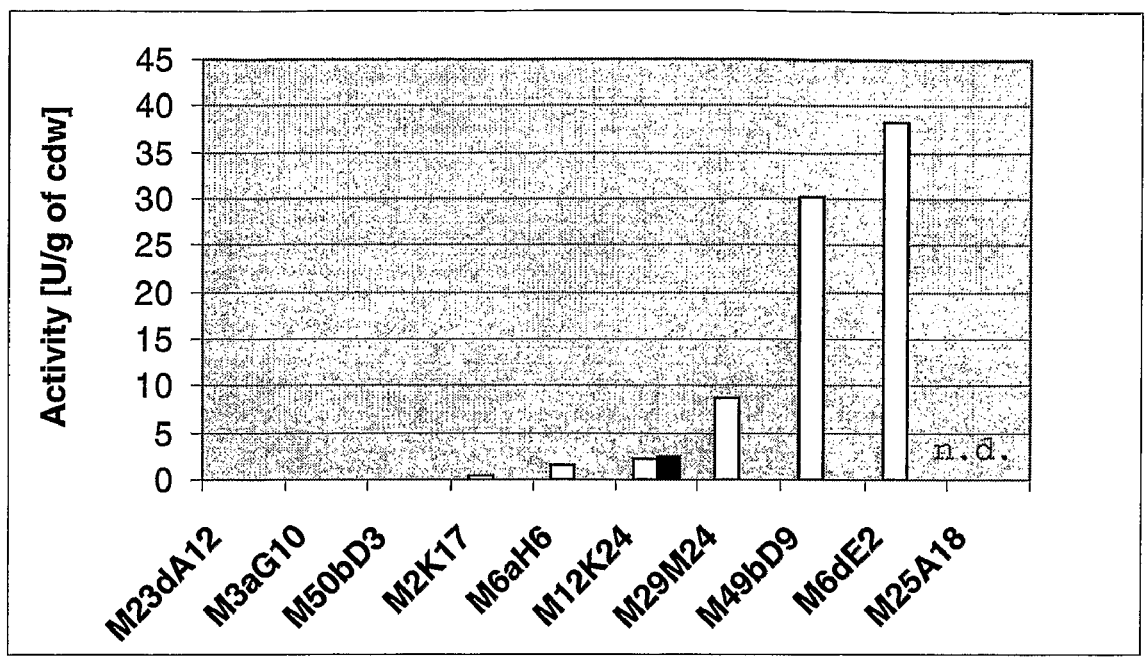
FIG. 2: Activity of different metagenome nitrile hydratases toward benzonitrile following expression in *E. coli* BL21 (DE3) codon plus RIL, with ☐ and ■ without coexpression of the trigger factor (n.d.: not determined).
Figure 3:
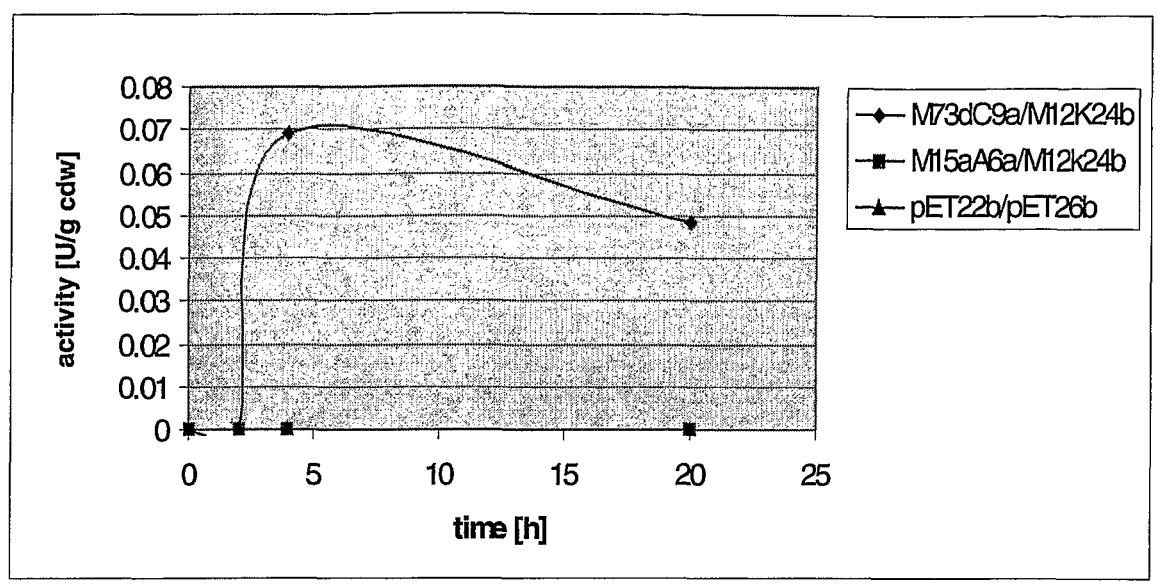
FIG. 3: Activity of nitrile hydratases when subunits from different metagenome clones are combined.
Figure 4:
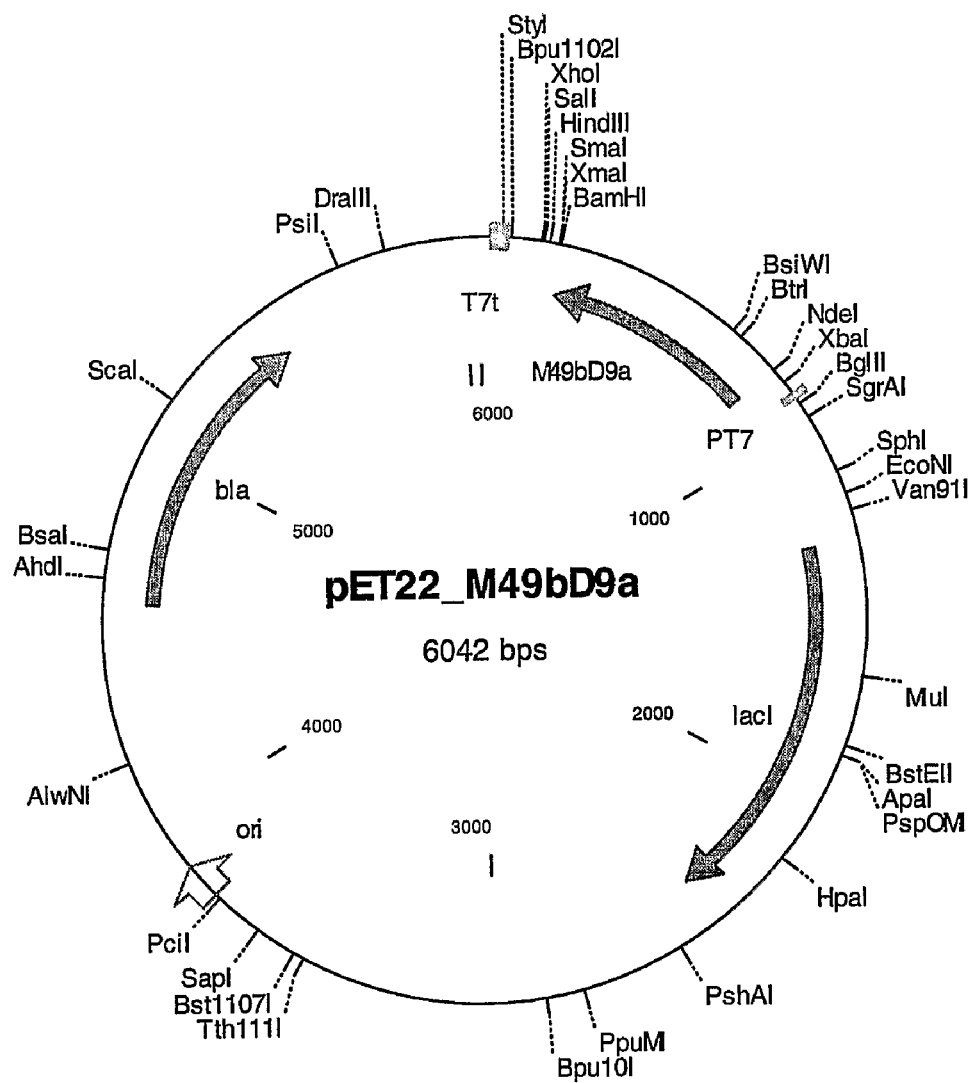
FIG. 4: The vector map shows the general arrangement of the α subunits in plasmid pET22, taking clone M49bD9 as an example.
Figure 5:
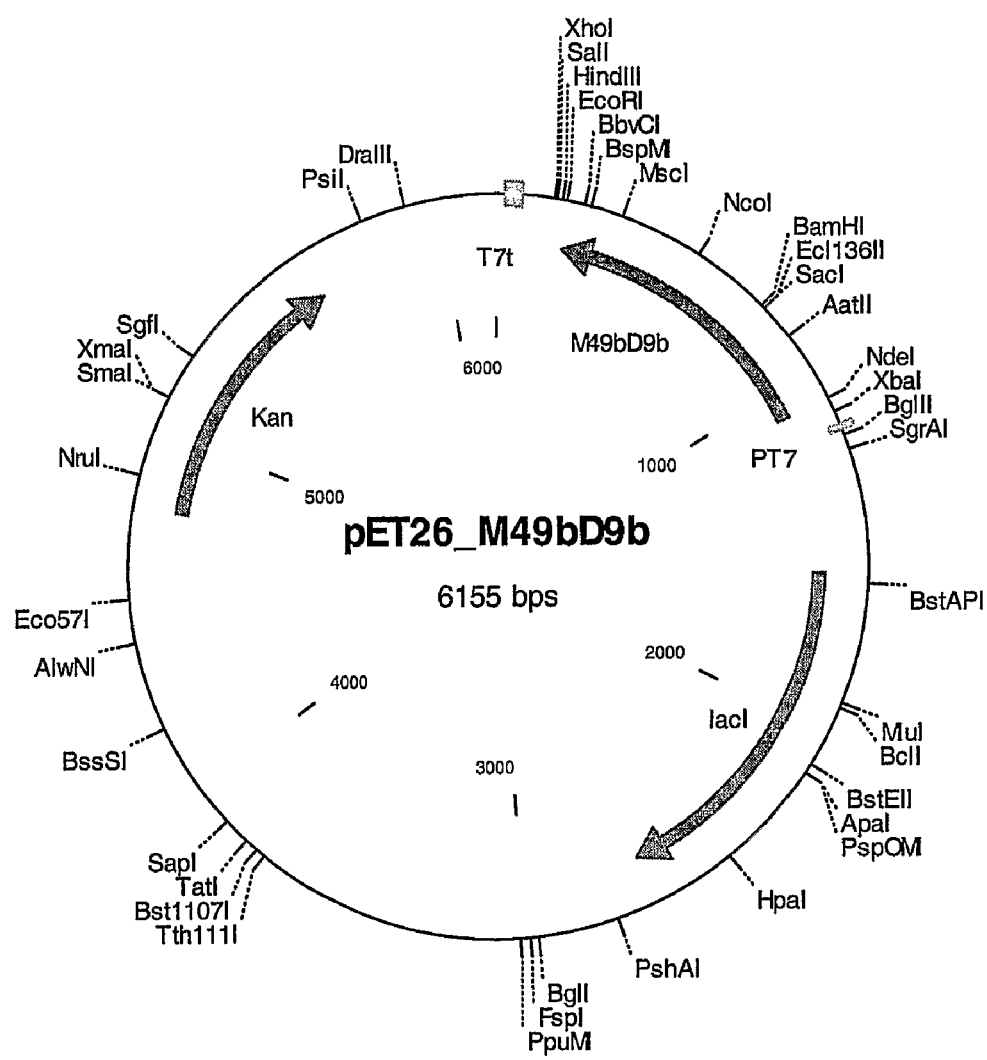
FIG. 5: The vector map shows the general arrangement of the β subunits in plasmid pET26 taking clone M49bD9 as an example.
Figure 6:
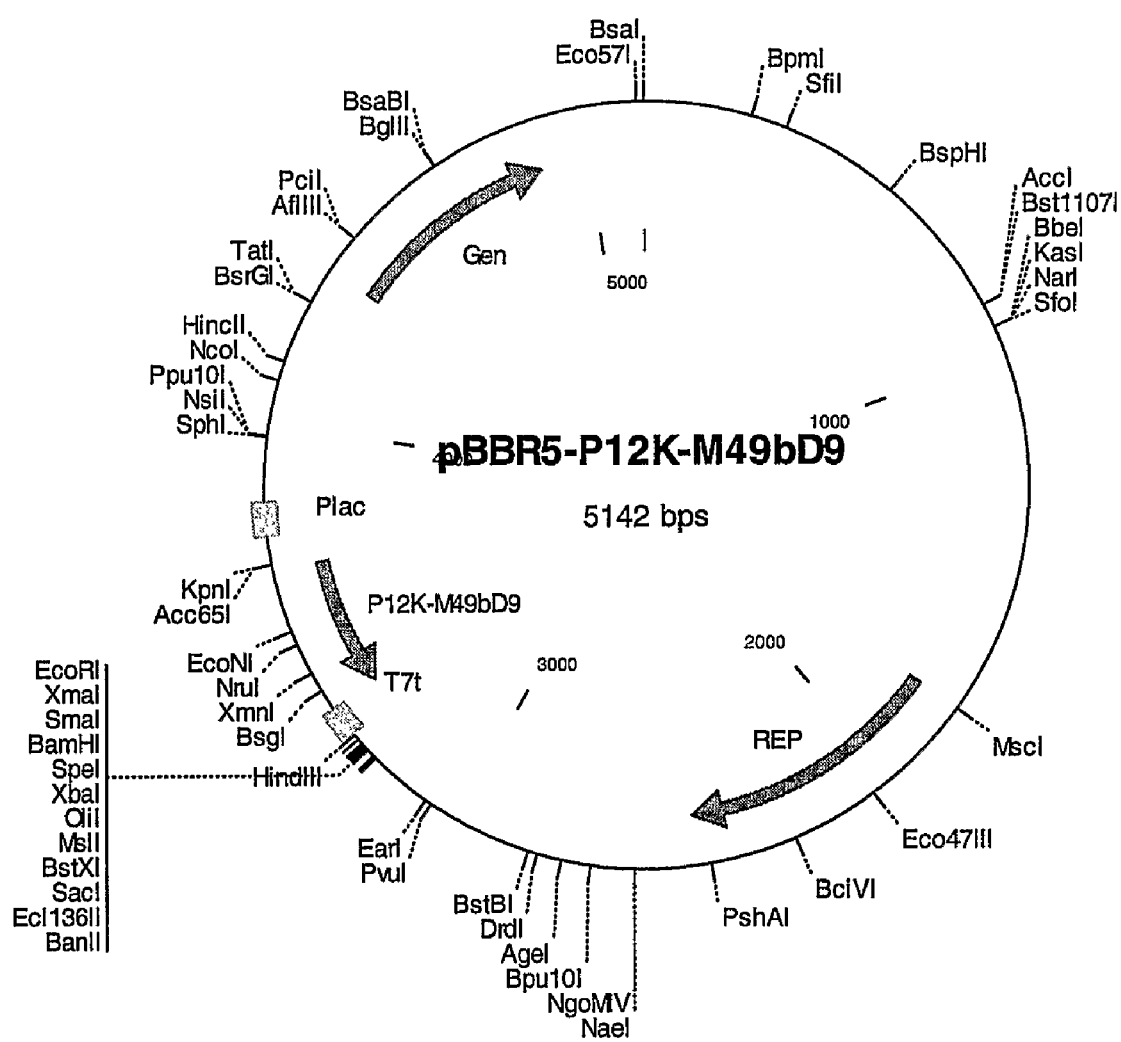
FIG. 6: The vector map shows the arrangement of the P12K protein from clone M49bD9 in plasmid pBBR5.
Figure 7:
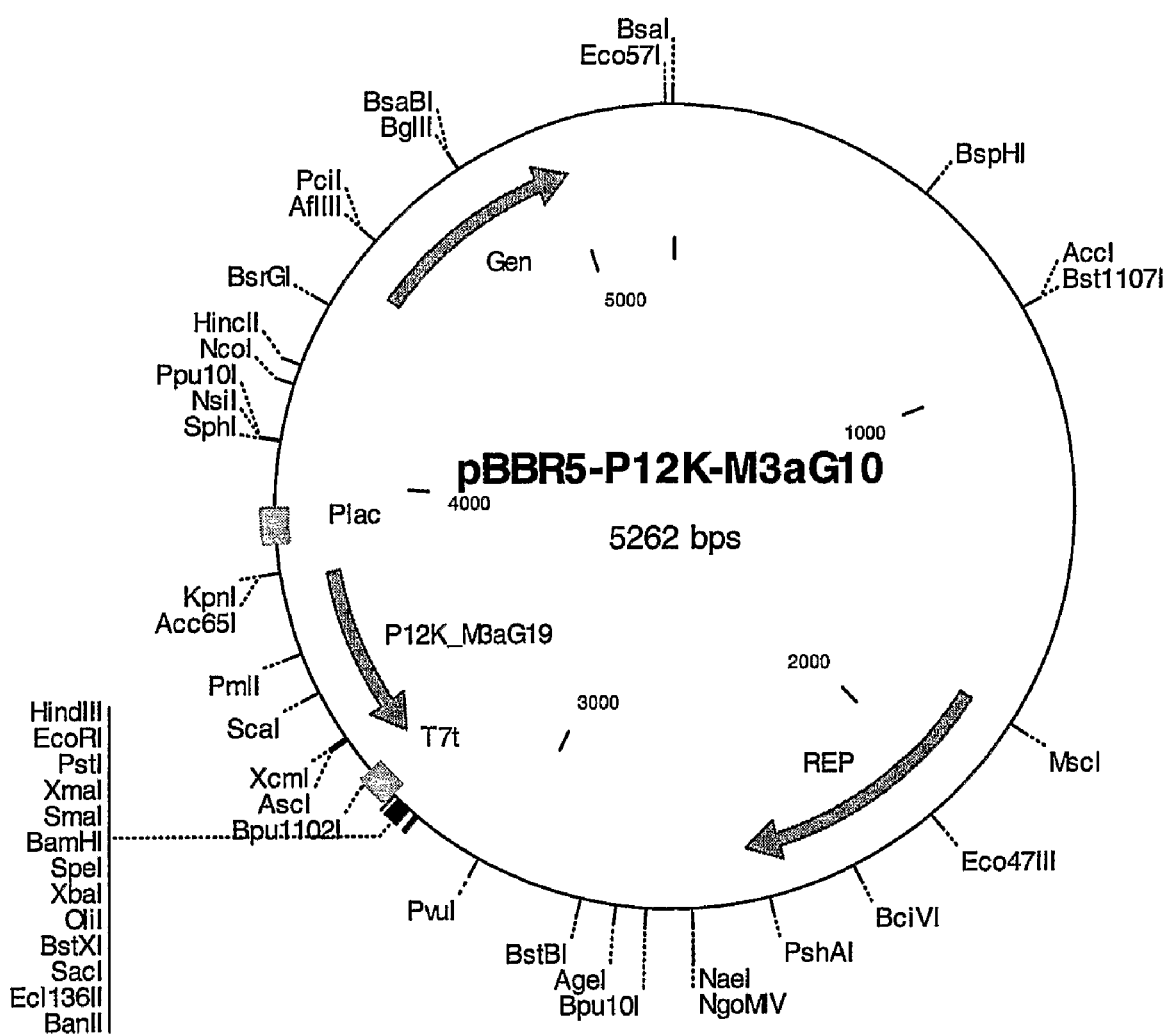
FIG. 7: The vector map shows the arrangement of the P12K protein from clone M3aG10 in plasmid pBBR5.

The *E. coli* cells were cultured and stored as described in Sambrock et al. (Sambrook, J.; Fritsch, E. F. and Maniatis, T. (1989), Molecular cloning: a laboratory manual, 2$^{nd}$ ed., Cold Spring Harbor Laboratory Press, New York).

PCR Protocol:

A typical PCR protocol is described below, with it being necessary to adapt the protocol in accordance with the manufacturer's instructions when using a different polymerase.
25 µl of HotStarTaq mastermix, Qiagen (2.5 U of polymerase, 200 g dNTPs, 1×PCR buffer)
25 pmol of primer 01f
25 pmol of primer 01r
2 µl of template DNA (20-200 ng)
dist. water to 50 µl Program:

| Initial denaturation: | 1 × 15 min at 95° C. |
|---|---|
| Cycle program: | 35 × { 1 min at 95° C.<br>1 min at 55-69° C.<br>1 min at 72° C. |
| Final elongation: | 1 × 7 min at 72° C. |
| Last extension: | 7 min at 72° C. |

Digestion with Restriction Enzymes

The DNA to be cut is provided with 5 U of restriction enzyme and the appurtenant buffer and, unless otherwise required, incubated at 37° C. Chromosomal DNA is digested with 10 U of enzyme. The incubation period is 1.5-2.5 hours.

Treatment with Alkaline Phosphatase

In order to prevent vectors which have only been cut with one restriction endonuclease from religating with themselves, the phosphate residue protruding at the 5' end is removed with alkaline phosphatase. Circular DNA can only be formed once again by inserting a DNA fragment.

The vector which has been cut with a restriction endonuclease is incubated at 65° C. for 15 minutes in order to stop the restriction endonuclease. The dephosphorylation buffer is then added and the vector is incubated with 1 U of shrimp alkaline phosphatase at 37° C. for 10 min. The enzyme is then separated off from the vector DNA by means of a subsequent gel electrophoresis.

Treatment with T4 DNA Ligase

Vector and insert are used for the ligation in a ratio of 1:3. The volume is chosen to be as small as possible (7-20 µl). The mixture is incubated overnight at 16° C. in ligation buffer and in the presence of 1 U of ligase.

Transformation

100 µl of competent cells are added by pipette to the ligation mixture, the constituents of which are mixed by being repeatedly drawn up into the pipette. After 30 min of incubation on ice, a heat shock step at 42° C. is carried out for 45 sec and the mixture is incubated once again on ice for 2 min. 120-900 µl of SOC medium are added and the mixture is incubated at 37° C. for 45 min while being agitated. The mixture is subsequently plated out and incubated overnight at 37° C.

Expression of Metagenome Nitrile Hydratases

The constructs containing T7 promoters were expressed in accordance with the following protocol:

50 ml of LB$_{amp100}$ medium containing 2 mM Fe citrate and in each case 50 µg of kanamycin and ampicillin/ml were inoculated in a ratio of 99:1 with an overnight culture. After an OD$_{600}$ of approx. 0.5 had been reached, expression of the nitrile hydratases was induced with 1 mM IPTG (isopropylthiogalactoside). The cells were harvested approx. 24 hours after induction at 26° C.

Detection of Activity Using Benzonitrile as Substrate

The biotransformation was carried out on a 10 ml scale using approx. 100 mg of moist biomass ($OD_{600}$=5) in potassium phosphate buffer (100 mM), pH 7.0. The incubation took place at 30° C. and the substrate concentration was approx. 5 mM benzonitrile. Samples were taken every 5-10 min over a period of at most 1 hour. The sample volume was 100 μl and the reaction was stopped by adding 10 μl of 50% phosphoric acid.

The concentrations of benzonitrile and benzamide were then determined by means of HPLC:

Column: RP18 Phenomenex Hypersil ODS 5μ column (with precolumn)

Mobile phase: 10 mM K2HPO4, (pH 2.3)

Flow rate: 1 ml/min

Wavelength: 202 nm

Injection volume: 20 μl

Duration of HPLC run: 12-15 min

The activity was calculated by calculating a μmol turnover after one minute, with one μmol corresponding to one U (unit). Specific activities are given in U per g of DBM or mg of protein.

The invention claimed is:

1. A protein sequence, comprising:
   a) any of SEQ ID NOs: 50, 52, 54, 56, 58 or 60, or a protein sequence with 90% or more identity to any of SEQ ID NOs: 38, 40, 42, 46, 48, 50, 58 or 60;
   b) any of SEQ ID NOs: 62, 64, 72, 74, 76, 78, or 80, or a protein sequence with 90% or more identity to any of SEQ ID NOs: 62, 64, 66, 68, 70, 72, or 80; or
   c) any of SEQ ID NOs: 84 or 86, or a protein sequence with 90% or more identity to any of SEQ ID NOs: 84, or 86, wherein when any of the proteins of a) and b) are combined, or wherein when any of the proteins of a), b) and c) are combined, the combination has a nitrile hydratase activity.

2. A nitrile hydratase comprising protein sequences for α subunits and β subunits, respectively, in
   a) any of SEQ ID NOs: 50, 52, 54, 56, 58 or 60, or a protein sequence with 90% or more identity to any of SEQ ID NOs: 50, 52, 54, 56, 58 or 60; and
   b) any of SEQ ID NOs: 64, 66, 68, 70, 72, 74, 76, 78, or 80, or a protein sequence with 90% or more identity to any of SEQ ID NOs: 62, 64, 72, 74, 76, 78, or 80.

3. The protein sequence of claim 1, wherein the nitrile hydratase activity is conversion of benzonitrile into benzamide.

4. The protein sequence of claim 1, wherein the protein sequence is 95% or more identical to any of SEQ ID NOs: 50, 52, 54, 56, 58, 60, 62, 64, 72, 74, 76, 78, 80, 82, 84 or 86.

5. The protein sequence of claim 1, wherein the protein sequence is identical to any of SEQ ID NOs: 50, 52, 54, 56, 58, 60, 62, 64, 72, 74, 76, 78, 80, 84 or 86.

6. The nitrile hydratase of claim 2, further comprising a protein sequence of any of SEQ ID NOs: 84 or 86, or a protein sequence with 90% or more identity to any of SEQ ID NOs: 84, or 86.

* * * * *

SEQUENCE LISTING

```
<160> NUMBER OF SEQ ID NOS: 86

<210> SEQ ID NO 1
<211> LENGTH: 12
<212> TYPE: DNA
<213> ORGANISM: Artificial Sequence
<220> FEATURE:
<223> OTHER INFORMATION: Primer

<400> SEQUENCE: 1
gcsmrsgcst gg                                                          12

<210> SEQ ID NO 2
<211> LENGTH: 11
<212> TYPE: DNA
<213> ORGANISM: Artificial Sequence
<220> FEATURE:
<223> OTHER INFORMATION: Primer

<400> SEQUENCE: 2
ggsctsccsc c                                                           11

<210> SEQ ID NO 3
<211> LENGTH: 11
<212> TYPE: DNA
<213> ORGANISM: Artificial Sequence
<220> FEATURE:
<223> OTHER INFORMATION: Primer

<400> SEQUENCE: 3
ggsggsagsc c                                                           11

<210> SEQ ID NO 4
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u

<400> SEQUENCE: 4
ggncgcwbsg g                                                           11

<210> SEQ ID NO 5
<211> LENGTH: 12
<212> TYPE: DNA
<213> ORGANISM: Artificial Sequence
<220> FEATURE:
```

```
<223> OTHER INFORMATION: Primer
<220> FEATURE:
<221> NAME/KEY: misc_feature
<222> LOCATION: (3)..(3)
<223> OTHER INFORMATION: a or c
<220> FEATURE:
<221> NAME/KEY: misc_feature
<222> LOCATION: (9)..(9)
<223> OTHER INFORMATION: a or g or c or t/u

<400> SEQUENCE: 5
gcnmrrgcnt gg                                                              12

<210> SEQ ID NO 6
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u
<220> FEATURE:
<221> NAME/KEY: misc_feature
<222> LOCATION: (6)..(6)
<223> OTHER INFORMATION: a or g or c or t/u
<220> FEATURE:
<221> NAME/KEY: misc_feature
<222> LOCATION: (9)..(9)
<223> OTHER INFORMATION: a or g or c or t/u

<400> SEQUENCE: 6
ggnytnccnc c                                                               11

<210> SEQ ID NO 7
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u
<220> FEATURE:
<221> NAME/KEY: misc_feature
<222> LOCATION: (6)..(6)
<223> OTHER INFORMATION: a or g or c or t/u
<220> FEATURE:
<221> NAME/KEY: misc_feature
<222> LOCATION: (9)..(9)
<223> OTHER INFORMATION: a or g or c or t/u

<400> SEQUENCE: 7
ggnggnarnc c                                                               11

<210> SEQ ID NO 8
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u

<400> SEQUENCE: 8
gwngwrtccc a                                                               11
```

```
<210> SEQ ID NO 9
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u
<220> FEATURE:
<221> NAME/KEY: misc_feature
<222> LOCATION: (9)..(9)
<223> OTHER INFORMATION: a or g or c or t/u

<400> SEQUENCE: 9
gcntggryng a                                                                11

<210> SEQ ID NO 10
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u
<220> FEATURE:
<221> NAME/KEY: misc_feature
<222> LOCATION: (9)..(9)
<223> OTHER INFORMATION: a or g or c or t/u

<400> SEQUENCE: 10
ggnytsccnc c                                                                11

<210> SEQ ID NO 11
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u
<220> FEATURE:
<221> NAME/KEY: misc_feature
<222> LOCATION: (9)..(9)
<223> OTHER INFORMATION: a or g or c or t/u

<400> SEQUENCE: 11
ggnggsarnc c                                                                11

<210> SEQ ID NO 12
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: a or g or c or t/u

<400> SEQUENCE: 12
swnswrtccc a                                                                11

<210> SEQ ID NO 13
<211> LENGTH: 12
<212> TYPE: DNA
```

```
<213> ORGANISM: Artificial Sequence
<220> FEATURE:
<223> OTHER INFORMATION: Primer

<400> SEQUENCE: 13
gccaaggtcg tc                                                              12

<210> SEQ ID NO 14
<211> LENGTH: 11
<212> TYPE: DNA
<213> ORGANISM: Artificial Sequence
<220> FEATURE:
<223> OTHER INFORMATION: Primer

<400> SEQUENCE: 14
ggccggtcct g                                                               11

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
tccttgtacc aggtc                                                           15

<210> SEQ ID NO 16
<211> LENGTH: 7
<212> TYPE: DNA
<213> ORGANISM: Artificial Sequence
<220> FEATURE:
<223> OTHER INFORMATION: Primer

<400> SEQUENCE: 16 gcccgcc                                                                     7

<210> SEQ ID NO 17
<211> LENGTH: 15
<212> TYPE: DNA
<213> ORGANISM: Artificial Sequence
<220> FEATURE:
<223> OTHER INFORMATION: Primer

<400> SEQUENCE: 17
ggcgctaaag ttgtt                                                           15

<210> SEQ ID NO 18
<211> LENGTH: 12
<212> TYPE: DNA
<213> ORGANISM: Artificial Sequence
<220> FEATURE:
<223> OTHER INFORMATION: Primer

<400> SEQUENCE: 18
tggccggttc tg                                                              12

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
caaattcttt ataccaagtc                                                      20
```

-continued

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ccatatatcg catttcagct                                                  20

<210> SEQ ID NO 21
<211> LENGTH: 13
<212> TYPE: DNA
<213> ORGANISM: Artificial Sequence
<220> FEATURE:
<223> OTHER INFORMATION: Primer

<400> SEQUENCE: 21
ggtcgtggcc aag                                                         13

<210> SEQ ID NO 22
<211> LENGTH: 11
<212> TYPE: DNA
<213> ORGANISM: Artificial Sequence
<220> FEATURE:
<223> OTHER INFORMATION: Primer

<400> SEQUENCE: 22
ggccggtcct g                                                           11

<210> SEQ ID NO 23
<211> LENGTH: 15
<212> TYPE: DNA
<213> ORGANISM: Artificial Sequence
<220> FEATURE:
<223> OTHER INFORMATION: Primer

<400> SEQUENCE: 23
tccttgtacc aggtc                                                       15

<210> SEQ ID NO 24
<211> LENGTH: 13
<212> TYPE: DNA
<213> ORGANISM: Artificial Sequence
<220> FEATURE:
<223> OTHER INFORMATION: Primer

<400> SEQUENCE: 24
gcgcatttcg gcg                                                         13

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gccaaggtcg tcgcsmrsgc stgg                                             24

<210> SEQ ID NO 26
<211> LENGTH: 22
<212> TYPE: DNA
<213> ORGANISM: Artificial Sequence
<220> FEATURE:

```
<223> OTHER INFORMATION: Primer

<400> SEQUENCE: 26
ggccggtcct gggsctsccs cc                                              22

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
tccttgtacc aggtcggsgg sagscc                                          26

<210> SEQ ID NO 28
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (10)..(10)
<223> OTHER INFORMATION: a or c or g or t/u

<400> SEQUENCE: 28
gcccgccggn cgcwbsgg                                                   18

<210> SEQ ID NO 29
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: a or c or g or t/u
<220> FEATURE:
<221> NAME/KEY: misc_feature
<222> LOCATION: (24)..(24)
<223> OTHER INFORMATION: a or c or g or t/u

<400> SEQUENCE: 29
ggcgctaaag ttgttgcnmr rgcntgg                                         27

<210> SEQ ID NO 30
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: a or c or g or t/u
<220> FEATURE:
<221> NAME/KEY: misc_feature
<222> LOCATION: (18)..(18)
<223> OTHER INFORMATION: a or c or g or t/u
<220> FEATURE:
<221> NAME/KEY: misc_feature
<222> LOCATION: (21)..(21)
<223> OTHER INFORMATION: a or c or g or t/u

<400> SEQUENCE: 30
tggccggttc tgggnytncc nc                                              22
```

```
<210> SEQ ID NO 31
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: a or c or g or t/u
<220> FEATURE:
<221> NAME/KEY: misc_feature
<222> LOCATION: (26)..(26)
<223> OTHER INFORMATION: a or c or g or t/u
<220> FEATURE:
<221> NAME/KEY: misc_feature
<222> LOCATION: (29)..(29)
<223> OTHER INFORMATION: a or c or g or t/u

<400> SEQUENCE: 31
caaattcttt ataccaagtc ggnggnarnc c                              31

<210> SEQ ID NO 32
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: a or c or g or t/u

<400> SEQUENCE: 32
ccatatatcg catttcagct gwngwrtccc a                              31

<210> SEQ ID NO 33
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: a or c or g or t/u
<220> FEATURE:
<221> NAME/KEY: misc_feature
<222> LOCATION: (22)..(22)
<223> OTHER INFORMATION: a or c or g or t/u

<400> SEQUENCE: 33
ggtcgtggcc aaggcntggr ynga                                      24

<210> SEQ ID NO 34
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(14)
<223> OTHER INFORMATION: a or c or g or t/u
<220> FEATURE:
<221> NAME/KEY: misc_feature
<222> LOCATION: (20)..(20)
<223> OTHER INFORMATION: a or c or g or t/u

<400> SEQUENCE: 34
ggccggtcct gggnytsccn cc                                        22
```

-continued

```
<210> SEQ ID NO 35
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: a or c or g or t/u
<220> FEATURE:
<221> NAME/KEY: misc_feature
<222> LOCATION: (24)..(24)
<223> OTHER INFORMATION: a or c or g or t/u

<400> SEQUENCE: 35
tccttgtacc aggtcggngg sarncc                                         26

<210> SEQ ID NO 36
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: a or c or g or t/u

<400> SEQUENCE: 36
gcgcatttcg gcgswnswrt ccca                                           24

<210> SEQ ID NO 37
<211> LENGTH: 705
<212> TYPE: DNA
<213> ORGANISM: Unknown
<220> FEATURE:
<223> OTHER INFORMATION: Metagenome - alpha unit nitrile hydratase -
      M6aH6
<220> FEATURE:
<221> NAME/KEY: CDS
<222> LOCATION: (1)..(705)

<400> SEQUENCE: 37 atg agc aag cac gta cac gat tac tac gcg aag aag aag cac gac cac     48
Met Ser Lys His Val His Asp Tyr Tyr Ala Lys Lys Lys His Asp His
1               5                   10                  15 gat cat gac cac gac gtc cac gag gcg atc gag gac cgg gac gag ggt     96
Asp His Asp His Asp Val His Glu Ala Ile Glu Asp Arg Asp Glu Gly
            20                  25                  30 ccg ccg tcg gaa ttc gag atc atg agc cgc gcc atg cag gag ctg ctg    144
Pro Pro Ser Glu Phe Glu Ile Met Ser Arg Ala Met Gln Glu Leu Leu
        35                  40                  45 gaa gag aag ggc gtc gtc acc gcg gag cag gtc cgg cgc agc atg gag    192
Glu Glu Lys Gly Val Val Thr Ala Glu Gln Val Arg Arg Ser Met Glu
    50                  55                  60 aag ttc gag gaa gag ctg ccc tac cgg ggg gcg cgg gtc gtc gcg cac    240
Lys Phe Glu Glu Glu Leu Pro Tyr Arg Gly Ala Arg Val Val Ala His
65                  70                  75                  80 gcc tgg acc gac ccg gaa ttc aag aag cgg ctg ctg gcg gac ggc aag    288
Ala Trp Thr Asp Pro Glu Phe Lys Lys Arg Leu Leu Ala Asp Gly Lys
                85                  90                  95 gcc gcc gtc tcg gag ttc ggc atc gat ttg gaa gcc gag cgg ctg atc    336
Ala Ala Val Ser Glu Phe Gly Ile Asp Leu Glu Ala Glu Arg Leu Ile
            100                 105                 110 gcg gtc gcg aac aca acg gac gtg cac aac gtc atc gtg tgc acg ctg    384
```

```
Ala Val Ala Asn Thr Thr Asp Val His Asn Val Ile Val Cys Thr Leu
            115                 120                 125 tgc tcg tgc tac ccg cgc acg ctg ctc ggc atg ccg ccg acc tgg tac       432
Cys Ser Cys Tyr Pro Arg Thr Leu Leu Gly Met Pro Pro Thr Trp Tyr
130                 135                 140 aag agc gat aac tac cgc tcg cgc gtg gtc tac gaa ccg cgc gcg gtg       480
Lys Ser Asp Asn Tyr Arg Ser Arg Val Val Tyr Glu Pro Arg Ala Val
145                 150                 155                 160 ctg aag gaa ttc ggc acc gtg ctg ccg gag cgc gtc acc gtg cgc gtg       528
Leu Lys Glu Phe Gly Thr Val Leu Pro Glu Arg Val Thr Val Arg Val
                165                 170                 175 cac gac tcc aac gcc gac atg cgc tac gtg gtg atc ccc atg cgc ccg       576
His Asp Ser Asn Ala Asp Met Arg Tyr Val Val Ile Pro Met Arg Pro
            180                 185                 190 cag gga acc gag ggc tgg agc gag gag cgg ctc gcg gag ctg ctg acg       624
Gln Gly Thr Glu Gly Trp Ser Glu Glu Arg Leu Ala Glu Leu Leu Thr
        195                 200                 205 cgc gac acg ctg gtg ggg gtc acc gtg cca aaa gtg gaa gtc gga agt       672
Arg Asp Thr Leu Val Gly Val Thr Val Pro Lys Val Glu Val Gly Ser
210                 215                 220 cga aag tcg aaa ggc gga agt aaa acc cgc tag                           705
Arg Lys Ser Lys Gly Gly Ser Lys Thr Arg
225                 230

<210> SEQ ID NO 38
<211> LENGTH: 234
<212> TYPE: PRT
<213> ORGANISM: Unknown
<220> FEATURE:
<223> OTHER INFORMATION: Metagenome - alpha unit nitrile hydratase -
      M6aH6

<400> SEQUENCE: 38

Met Ser Lys His Val His Asp Tyr Tyr Ala Lys Lys His Asp His
1               5                   10                  15

Asp His Asp His Asp Val His Glu Ala Ile Glu Asp Arg Asp Glu Gly
            20                  25                  30

Pro Pro Ser Glu Phe Glu Ile Met Ser Arg Ala Met Gln Glu Leu Leu
        35                  40                  45

Glu Glu Lys Gly Val Val Thr Ala Glu Gln Val Arg Arg Ser Met Glu
50                  55                  60

Lys Phe Glu Glu Glu Leu Pro Tyr Arg Gly Ala Arg Val Val Ala His
65                  70                  75                  80

Ala Trp Thr Asp Pro Glu Phe Lys Lys Arg Leu Leu Ala Asp Gly Lys
                85                  90                  95

Ala Ala Val Ser Glu Phe Gly Ile Asp Leu Glu Ala Glu Arg Leu Ile
            100                 105                 110

Ala Val Ala Asn Thr Thr Asp Val His Asn Val Ile Val Cys Thr Leu
            115                 120                 125

Cys Ser Cys Tyr Pro Arg Thr Leu Leu Gly Met Pro Pro Thr Trp Tyr
130                 135                 140

Lys Ser Asp Asn Tyr Arg Ser Arg Val Val Tyr Glu Pro Arg Ala Val
145                 150                 155                 160

Leu Lys Glu Phe Gly Thr Val Leu Pro Glu Arg Val Thr Val Arg Val
                165                 170                 175

His Asp Ser Asn Ala Asp Met Arg Tyr Val Val Ile Pro Met Arg Pro
            180                 185                 190

Gln Gly Thr Glu Gly Trp Ser Glu Glu Arg Leu Ala Glu Leu Leu Thr
```

```
                195                 200                 205
Arg Asp Thr Leu Val Gly Val Thr Val Pro Lys Val Glu Val Gly Ser
    210                 215                 220

Arg Lys Ser Lys Gly Gly Ser Lys Thr Arg
225                 230
```

<210> SEQ ID NO 39
<211> LENGTH: 657
<212> TYPE: DNA
<213> ORGANISM: Unknown
<220> FEATURE:
<223> OTHER INFORMATION: Metagenome - alpha unit nitrile hydratase - M12K24
<220> FEATURE:
<221> NAME/KEY: CDS
<222> LOCATION: (1)..(657)

<400> SEQUENCE: 39

```
atg tcg gac gga aca aca att gga atc cag gcc gcg aca acc ctt cga     48
Met Ser Asp Gly Thr Thr Ile Gly Ile Gln Ala Ala Thr Thr Leu Arg
1               5                   10                  15 tca gcc atg aac att cca gct cgt gaa ttc gcc ctc cag cgc act gcg     96
Ser Ala Met Asn Ile Pro Ala Arg Glu Phe Ala Leu Gln Arg Thr Ala
                20                  25                  30 ccg gtc gag cag cgt gtc gac gcg atc cag gcg gcg ctc gac gaa cgc    144
Pro Val Glu Gln Arg Val Asp Ala Ile Gln Ala Ala Leu Asp Glu Arg
            35                  40                  45 ggt ttg aac gcc agt gac gca gtc cag gaa ttg agc cac ctg gcg gag    192
Gly Leu Asn Ala Ser Asp Ala Val Gln Glu Leu Ser His Leu Ala Glu
        50                  55                  60 gag caa tgg att ccg cgc aat ggc gcg cgg gtc gtc gcc aaa gcc tgg    240
Glu Gln Trp Ile Pro Arg Asn Gly Ala Arg Val Val Ala Lys Ala Trp
65                  70                  75                  80 gtc gac ccg gaa ttc cgc gcg cgg ctt ctg gcc gac ggt cgc gcc gcc    288
Val Asp Pro Glu Phe Arg Ala Arg Leu Leu Ala Asp Gly Arg Ala Ala
                85                  90                  95 gtt gcc gaa ctg ggc ctc tcg atg ccg aag cat cac cgg cac ctc gtg    336
Val Ala Glu Leu Gly Leu Ser Met Pro Lys His His Arg His Leu Val
            100                 105                 110 gtg ctg gag aac acg ccg agc gtg cag aac gtc atc tgc tgc acg cag    384
Val Leu Glu Asn Thr Pro Ser Val Gln Asn Val Ile Cys Cys Thr Gln
        115                 120                 125 tgc tcg tgc acg gcg ttc acg atc atc gga ctg ccg ccc gac tgg tac    432
Cys Ser Cys Thr Ala Phe Thr Ile Ile Gly Leu Pro Pro Asp Trp Tyr
    130                 135                 140 aag gac ctg gaa tac cgc gcg cga gtc gtc cgg gag tcg cgc acc gtg    480
Lys Asp Leu Glu Tyr Arg Ala Arg Val Val Arg Glu Ser Arg Thr Val
145                 150                 155                 160 ctg aag gag atg gga ctg gat ctg cct cgg gat gtc gaa att cgc gtc    528
Leu Lys Glu Met Gly Leu Asp Leu Pro Arg Asp Val Glu Ile Arg Val
                165                 170                 175 tgg gat acc act gcc gac acg cgc tac atg gta ttg ccg gta cag ccg    576
Trp Asp Thr Thr Ala Asp Thr Arg Tyr Met Val Leu Pro Val Gln Pro
            180                 185                 190 ccg gaa acc atc ggc tgg ccc gag gag aaa ctg gtc gac atc gtg acg    624
Pro Glu Thr Ile Gly Trp Pro Glu Glu Lys Leu Val Asp Ile Val Thr
        195                 200                 205 cgc gac ggc atg atc ggc gtc gcg cgg gta tag                        657
Arg Asp Gly Met Ile Gly Val Ala Arg Val
    210                 215
```

<210> SEQ ID NO 40
<211> LENGTH: 218
<212> TYPE: PRT
<213> ORGANISM: Unknown
<220> FEATURE:
<223> OTHER INFORMATION: Metagenome - alpha unit nitrile hydratase - M12K24

<400> SEQUENCE: 40

Met Ser Asp Gly Thr Thr Ile Gly Ile Gln Ala Ala Thr Thr Leu Arg
1               5                   10                  15

Ser Ala Met Asn Ile Pro Ala Arg Glu Phe Ala Leu Gln Arg Thr Ala
            20                  25                  30

Pro Val Glu Gln Arg Val Asp Ala Ile Gln Ala Ala Leu Asp Glu Arg
        35                  40                  45

Gly Leu Asn Ala Ser Asp Ala Val Gln Glu Leu Ser His Leu Ala Glu
    50                  55                  60

Glu Gln Trp Ile Pro Arg Asn Gly Ala Arg Val Val Ala Lys Ala Trp
65                  70                  75                  80

Val Asp Pro Glu Phe Arg Ala Arg Leu Leu Ala Asp Gly Arg Ala Ala
                85                  90                  95

Val Ala Glu Leu Gly Leu Ser Met Pro Lys His His Arg His Leu Val
            100                 105                 110

Val Leu Glu Asn Thr Pro Ser Val Gln Asn Val Ile Cys Cys Thr Gln
        115                 120                 125

Cys Ser Cys Thr Ala Phe Thr Ile Ile Gly Leu Pro Pro Asp Trp Tyr
    130                 135                 140

Lys Asp Leu Glu Tyr Arg Ala Arg Val Val Arg Glu Ser Arg Thr Val
145                 150                 155                 160

Leu Lys Glu Met Gly Leu Asp Leu Pro Arg Asp Val Glu Ile Arg Val
                165                 170                 175

Trp Asp Thr Thr Ala Asp Thr Arg Tyr Met Val Leu Pro Val Gln Pro
            180                 185                 190

Pro Glu Thr Ile Gly Trp Pro Glu Glu Lys Leu Val Asp Ile Val Thr
        195                 200                 205

Arg Asp Gly Met Ile Gly Val Ala Arg Val
    210                 215

<210> SEQ ID NO 41
<211> LENGTH: 699
<212> TYPE: DNA
<213> ORGANISM: Unknown
<220> FEATURE:
<223> OTHER INFORMATION: Metagenome - alpha unit nitrile hydratase - M29M24
<220> FEATURE:
<221> NAME/KEY: CDS
<222> LOCATION: (1)..(699)

<400> SEQUENCE: 41 atg gag acg aca cgc cgc ggc ttc ttg aag aaa gcc ggg acc gcc gcc      48
Met Glu Thr Thr Arg Arg Gly Phe Leu Lys Lys Ala Gly Thr Ala Ala
1               5                   10                  15 ggt gcg acg gct gca ccc gtt gga ctc gcc aag atc gct cac tcc cac      96
Gly Ala Thr Ala Ala Pro Val Gly Leu Ala Lys Ile Ala His Ser His
            20                  25                  30 gag cac cag gcc gtt cct tcc gac ctc acg ctc cgg gtc aag tcc ctc     144
Glu His Gln Ala Val Pro Ser Asp Leu Thr Leu Arg Val Lys Ser Leu
        35                  40                  45 gaa tcg ctg ctg gtc gag aag ggt ctc gtg gac cgt gag gcc ctc gac     192

```
                                                                          -continued Glu Ser Leu Leu Val Glu Lys Gly Leu Val Asp Arg Glu Ala Leu Asp
    50                  55                  60 gtg ctc gtc gat acc tac gag aac aag atc ggt ccg cga aac ggc gct       240
Val Leu Val Asp Thr Tyr Glu Asn Lys Ile Gly Pro Arg Asn Gly Ala
65              70                  75                  80 cgc gtc gtc gcg cgg gcg tgg gtc gat ccc gcg tac aaa gag cgc ctg       288
Arg Val Val Ala Arg Ala Trp Val Asp Pro Ala Tyr Lys Glu Arg Leu
                85                  90                  95 ctg aaa gac gcc acc tcg gcg atc gcc gag ctc ggt tac acc gga gcc       336
Leu Lys Asp Ala Thr Ser Ala Ile Ala Glu Leu Gly Tyr Thr Gly Ala
            100                 105                 110 cag ggt gag cac atg gtg gcg ctc gag aat acc ccc gcg gtg cac aac       384
Gln Gly Glu His Met Val Ala Leu Glu Asn Thr Pro Ala Val His Asn
        115                 120                 125 ctc gtc gtt tgc acg ctc tgc tcc tgc tat cca tgg ccg gtg ctc ggt       432
Leu Val Val Cys Thr Leu Cys Ser Cys Tyr Pro Trp Pro Val Leu Gly
    130                 135                 140 ctg ccc ccg gtc tgg tac aaa tcg gcg ccc tac cga tcg cgc tcg gtc       480
Leu Pro Pro Val Trp Tyr Lys Ser Ala Pro Tyr Arg Ser Arg Ser Val
145                 150                 155                 160 atc gat ccg cgc ggc gtt ctc ggc gag ttc ggg ctc gag ctg ccg gaa       528
Ile Asp Pro Arg Gly Val Leu Gly Glu Phe Gly Leu Glu Leu Pro Glu
                165                 170                 175 ggg gtc gag gtg cgc gtc tgg gac tcg acg gcg gag ctc cgg tat ctc       576
Gly Val Glu Val Arg Val Trp Asp Ser Thr Ala Glu Leu Arg Tyr Leu
            180                 185                 190 gtt ttg ccg gag cgg ccc gaa ggc acg gcg caa ctg agc gaa gaa gcg       624
Val Leu Pro Glu Arg Pro Glu Gly Thr Ala Gln Leu Ser Glu Glu Ala
        195                 200                 205 ctc gcg gat ctc gtc acc cgg gat gcc atg atc ggc gtc gcg aaa gtc       672
Leu Ala Asp Leu Val Thr Arg Asp Ala Met Ile Gly Val Ala Lys Val
    210                 215                 220 tcg ttg ccc gcg ggc ggc gcc gaa tga                                   699
Ser Leu Pro Ala Gly Gly Ala Glu
225                 230

<210> SEQ ID NO 42
<211> LENGTH: 232
<212> TYPE: PRT
<213> ORGANISM: Unknown
<220> FEATURE:
<223> OTHER INFORMATION: Metagenome - alpha unit nitrile hydratase -
      M29M24

<400> SEQUENCE: 42

Met Glu Thr Thr Arg Arg Gly Phe Leu Lys Lys Ala Gly Thr Ala Ala
1               5                   10                  15

Gly Ala Thr Ala Ala Pro Val Gly Leu Ala Lys Ile Ala His Ser His
                20                  25                  30

Glu His Gln Ala Val Pro Ser Asp Leu Thr Leu Arg Val Lys Ser Leu
            35                  40                  45

Glu Ser Leu Leu Val Glu Lys Gly Leu Val Asp Arg Glu Ala Leu Asp
        50                  55                  60

Val Leu Val Asp Thr Tyr Glu Asn Lys Ile Gly Pro Arg Asn Gly Ala
65                  70                  75                  80

Arg Val Val Ala Arg Ala Trp Val Asp Pro Ala Tyr Lys Glu Arg Leu
                85                  90                  95

Leu Lys Asp Ala Thr Ser Ala Ile Ala Glu Leu Gly Tyr Thr Gly Ala
            100                 105                 110
```

```
Gln Gly Glu His Met Val Ala Leu Glu Asn Thr Pro Ala Val His Asn
        115                 120                 125

Leu Val Val Cys Thr Leu Cys Ser Cys Tyr Pro Trp Pro Val Leu Gly
130                 135                 140

Leu Pro Pro Val Trp Tyr Lys Ser Ala Pro Tyr Arg Ser Arg Ser Val
145                 150                 155                 160

Ile Asp Pro Arg Gly Val Leu Gly Glu Phe Gly Leu Glu Leu Pro Glu
                165                 170                 175

Gly Val Glu Val Arg Val Trp Asp Ser Thr Ala Glu Leu Arg Tyr Leu
            180                 185                 190

Val Leu Pro Glu Arg Pro Gly Thr Ala Gln Leu Ser Glu Glu Ala
        195                 200                 205

Leu Ala Asp Leu Val Thr Arg Asp Ala Met Ile Gly Val Ala Lys Val
210                 215                 220

Ser Leu Pro Ala Gly Gly Ala Glu
225                 230
```

<210> SEQ ID NO 43
<211> LENGTH: 639
<212> TYPE: DNA
<213> ORGANISM: Unknown
<220> FEATURE:
<223> OTHER INFORMATION: Metagenome - alpha unit nitrile hydratase -
      M2K17
<220> FEATURE:
<221> NAME/KEY: CDS
<222> LOCATION: (1)..(639)

<400> SEQUENCE: 43

```
atg cct gac gac cat gcc cat ccg gat gat cat gcg cat ggc tcg gaa       48
Met Pro Asp Asp His Ala His Pro Asp Asp His Ala His Gly Ser Glu
1               5                   10                  15 ttg tcc gag atg gat atc cgg gtg cgg gcg ctg gag acc atc ctg acc       96
Leu Ser Glu Met Asp Ile Arg Val Arg Ala Leu Glu Thr Ile Leu Thr
            20                  25                  30 gag aag ggc tat gtc gat ccg gcg gcg ctc gac cgg atc gtc gag gcg      144
Glu Lys Gly Tyr Val Asp Pro Ala Ala Leu Asp Arg Ile Val Glu Ala
        35                  40                  45 ttc gag acc agg atc ggc ccg cat atc ggc gcc cgt atc gtg gca cgg      192
Phe Glu Thr Arg Ile Gly Pro His Ile Gly Ala Arg Ile Val Ala Arg
    50                  55                  60 gct tgg gcc gac gcc gaa ttc aag cgg cgg ctg ctc gcc gac gcg acc      240
Ala Trp Ala Asp Ala Glu Phe Lys Arg Arg Leu Leu Ala Asp Ala Thr
65                  70                  75                  80 gag gcg gcg aat tcg ctg ggt cat gcg agc ccg gtc ggc agc cat ctg      288
Glu Ala Ala Asn Ser Leu Gly His Ala Ser Pro Val Gly Ser His Leu
                85                  90                  95 atc gcg gtc gag aac acg ccg cag acc cac aac ctc gtc gtc tgc act      336
Ile Ala Val Glu Asn Thr Pro Gln Thr His Asn Leu Val Val Cys Thr
            100                 105                 110 ttg tgc tcg tgt tat ccg tgg gag gtg ctg gga ttg ccg ccg gtc tgg      384
Leu Cys Ser Cys Tyr Pro Trp Glu Val Leu Gly Leu Pro Pro Val Trp
        115                 120                 125 tac aaa tcc gct gcc tac cgc tcg cgc gtg gtg atc gac ccc aag ggc      432
Tyr Lys Ser Ala Ala Tyr Arg Ser Arg Val Val Ile Asp Pro Lys Gly
    130                 135                 140 gtc ctc gcc gag ttc ggc ctg acc ctg cca ccg gag acc ggg atc cgc      480
Val Leu Ala Glu Phe Gly Leu Thr Leu Pro Pro Glu Thr Gly Ile Arg
145                 150                 155                 160 atc tgg gat tcg acc gcc gag acc cgg ttt ctg gtg gtg ccg atg cgg      528
Ile Trp Asp Ser Thr Ala Glu Thr Arg Phe Leu Val Val Pro Met Arg
```

```
ccc ccc ggc acc gca ggc tgg agc gag gaa cgg ctc gcc gaa ctc gtc       576
Pro Pro Gly Thr Ala Gly Trp Ser Glu Glu Arg Leu Ala Glu Leu Val
            180                 185                 190 acc cgc gac agc atg atc ggc act ggt ctg gcc ggg gcg ccg cag gag       624
Thr Arg Asp Ser Met Ile Gly Thr Gly Leu Ala Gly Ala Pro Gln Glu
        195                 200                 205 atg gcc tcg gca tga                                                    639
Met Ala Ser Ala
    210
```

```
<210> SEQ ID NO 44
<211> LENGTH: 212
<212> TYPE: PRT
<213> ORGANISM: Unknown
<220> FEATURE:
<223> OTHER INFORMATION: Metagenome - alpha unit nitrile hydratase -
      M2K17

<400> SEQUENCE: 44
```

```
Met Pro Asp Asp His Ala His Pro Asp His Ala His Gly Ser Glu
1               5                   10                  15

Leu Ser Glu Met Asp Ile Arg Val Arg Ala Leu Glu Thr Ile Leu Thr
            20                  25                  30

Glu Lys Gly Tyr Val Asp Pro Ala Ala Leu Asp Arg Ile Val Glu Ala
        35                  40                  45

Phe Glu Thr Arg Ile Gly Pro His Ile Gly Ala Arg Ile Val Ala Arg
    50                  55                  60

Ala Trp Ala Asp Ala Glu Phe Lys Arg Arg Leu Leu Ala Asp Ala Thr
65                  70                  75                  80

Glu Ala Ala Asn Ser Leu Gly His Ala Ser Pro Val Gly Ser His Leu
                85                  90                  95

Ile Ala Val Glu Asn Thr Pro Gln Thr His Asn Leu Val Val Cys Thr
            100                 105                 110

Leu Cys Ser Cys Tyr Pro Trp Glu Val Leu Gly Leu Pro Pro Val Trp
        115                 120                 125

Tyr Lys Ser Ala Ala Tyr Arg Ser Arg Val Val Ile Asp Pro Lys Gly
    130                 135                 140

Val Leu Ala Glu Phe Gly Leu Thr Leu Pro Pro Glu Thr Gly Ile Arg
145                 150                 155                 160

Ile Trp Asp Ser Thr Ala Glu Thr Arg Phe Leu Val Val Pro Met Arg
                165                 170                 175

Pro Pro Gly Thr Ala Gly Trp Ser Glu Glu Arg Leu Ala Glu Leu Val
            180                 185                 190

Thr Arg Asp Ser Met Ile Gly Thr Gly Leu Ala Gly Ala Pro Gln Glu
        195                 200                 205

Met Ala Ser Ala
    210
```

```
<210> SEQ ID NO 45
<211> LENGTH: 696
<212> TYPE: DNA
<213> ORGANISM: Unknown
<220> FEATURE:
<223> OTHER INFORMATION: Metagenome - alpha unit nitrile hydratase -
      M15aA6
<220> FEATURE:
<221> NAME/KEY: CDS
<222> LOCATION: (1)..(696)
```

<400> SEQUENCE: 45

```
atg cgt tcg ccc ggt gag gcc tca gca acg caa cca gcg ctc att cgg      48
Met Arg Ser Pro Gly Glu Ala Ser Ala Thr Gln Pro Ala Leu Ile Arg
1               5                   10                  15 ctg cat gat cga gct ggc ggt gtt cga tca ttg cgc ggc aaa agg tct      96
Leu His Asp Arg Ala Gly Gly Val Arg Ser Leu Arg Gly Lys Arg Ser
                20                  25                  30 cat cgc gcc gga tcg cat cct cgg ggc gct cgc gca tcc gtc gcc aca     144
His Arg Ala Gly Ser His Pro Arg Gly Ala Arg Ala Ser Val Ala Thr
            35                  40                  45 ggg tgg ttc gtt ccg ttc tcg gcc agg ctc gcc cgg aaa ggc atc gct     192
Gly Trp Phe Val Pro Phe Ser Ala Arg Leu Ala Arg Lys Gly Ile Ala
50                  55                  60 cct ccg gcc gag atc gcc gag cgg atc gcc gtc acc gat cgc gca tca     240
Pro Pro Ala Glu Ile Ala Glu Arg Ile Ala Val Thr Asp Arg Ala Ser
65                  70                  75                  80 ccg gca atg ggc gct cgc atg gtc gcc aag gcc tgg acc gat ccc gcc     288
Pro Ala Met Gly Ala Arg Met Val Ala Lys Ala Trp Thr Asp Pro Ala
                85                  90                  95 ttc cgc acc ctg ctc ttg gaa gac gga acc cgc gcg gcg gaa tcg ctc     336
Phe Arg Thr Leu Leu Leu Glu Asp Gly Thr Arg Ala Ala Glu Ser Leu
            100                 105                 110 ggc atc atg atg cgc ggc gcc ccg cct ctc ggt gtg ctg gag aat acg     384
Gly Ile Met Met Arg Gly Ala Pro Pro Leu Gly Val Leu Glu Asn Thr
        115                 120                 125 ccc gag att cat cac ctc gtc gtt tgc acg ctg tgc agt tgt tac ccg     432
Pro Glu Ile His His Leu Val Val Cys Thr Leu Cys Ser Cys Tyr Pro
130                 135                 140 cgc gcg gtg ctg ggc tat ccg ccg ttc tgg ttc aaa tcc gcc gcc tac     480
Arg Ala Val Leu Gly Tyr Pro Pro Phe Trp Phe Lys Ser Ala Ala Tyr
145                 150                 155                 160 cgg gca cgt gcg gtg cgc gac ccg cgc ggt ctg atc gcc gaa tgg ggc     528
Arg Ala Arg Ala Val Arg Asp Pro Arg Gly Leu Ile Ala Glu Trp Gly
                165                 170                 175 acc atg ctg ccc gac gat gtc cgc gtg cga gtg gtg gac agt acg gcc     576
Thr Met Leu Pro Asp Asp Val Arg Val Arg Val Val Asp Ser Thr Ala
            180                 185                 190 gac tat cgc tgg atg gtt ctg ccg gtg cgg ccg gcc ggc act gcg ggc     624
Asp Tyr Arg Trp Met Val Leu Pro Val Arg Pro Ala Gly Thr Ala Gly
        195                 200                 205 tgg gat gag gag cgc ctc gcc gca atc gta cgc gaa ggc gat atg atc     672
Trp Asp Glu Glu Arg Leu Ala Ala Ile Val Arg Glu Gly Asp Met Ile
    210                 215                 220 ggg gtg acc atc cct cgt ctt taa                                     696
Gly Val Thr Ile Pro Arg Leu
225                 230
```

<210> SEQ ID NO 46
<211> LENGTH: 231
<212> TYPE: PRT
<213> ORGANISM: Unknown
<220> FEATURE:
<223> OTHER INFORMATION: Metagenome - alpha unit nitrile hydratase - M15aA6

<400> SEQUENCE: 46

```
Met Arg Ser Pro Gly Glu Ala Ser Ala Thr Gln Pro Ala Leu Ile Arg
1               5                   10                  15

Leu His Asp Arg Ala Gly Gly Val Arg Ser Leu Arg Gly Lys Arg Ser
                20                  25                  30
```

-continued

```
His Arg Ala Gly Ser His Pro Arg Gly Ala Arg Ala Ser Val Ala Thr
        35                  40                  45

Gly Trp Phe Val Pro Phe Ser Ala Arg Leu Ala Arg Lys Gly Ile Ala
 50                  55                  60

Pro Pro Ala Glu Ile Ala Glu Arg Ile Ala Val Thr Asp Arg Ala Ser
65                  70                  75                  80

Pro Ala Met Gly Ala Arg Met Val Ala Lys Ala Trp Thr Asp Pro Ala
                85                  90                  95

Phe Arg Thr Leu Leu Leu Glu Asp Gly Thr Arg Ala Ala Glu Ser Leu
            100                 105                 110

Gly Ile Met Met Arg Gly Ala Pro Leu Gly Val Leu Glu Asn Thr
            115                 120                 125

Pro Glu Ile His His Leu Val Val Cys Thr Leu Cys Ser Cys Tyr Pro
        130                 135                 140

Arg Ala Val Leu Gly Tyr Pro Pro Phe Trp Phe Lys Ser Ala Ala Tyr
145                 150                 155                 160

Arg Ala Arg Ala Val Arg Asp Pro Arg Gly Leu Ile Ala Glu Trp Gly
                165                 170                 175

Thr Met Leu Pro Asp Asp Val Arg Val Arg Val Val Asp Ser Thr Ala
            180                 185                 190

Asp Tyr Arg Trp Met Val Leu Pro Val Arg Pro Ala Gly Thr Ala Gly
        195                 200                 205

Trp Asp Glu Glu Arg Leu Ala Ala Ile Val Arg Glu Gly Asp Met Ile
210                 215                 220

Gly Val Thr Ile Pro Arg Leu
225                 230
```

<210> SEQ ID NO 47
<211> LENGTH: 576
<212> TYPE: DNA
<213> ORGANISM: Unknown
<220> FEATURE:
<223> OTHER INFORMATION: Metagenome - alpha unit nitrile hydratase - M23dA12
<220> FEATURE:
<221> NAME/KEY: CDS
<222> LOCATION: (1)..(576)

<400> SEQUENCE: 47

```
atg cag ttg cgc gtg cgg gcg ctg gaa acc gtt cta gcc gaa aag ggt      48
Met Gln Leu Arg Val Arg Ala Leu Glu Thr Val Leu Ala Glu Lys Gly
1               5                   10                  15 tat ctc gat ccc gcc gcg ctt gat gcg atg atc gaa gcc tac gag acg      96
Tyr Leu Asp Pro Ala Ala Leu Asp Ala Met Ile Glu Ala Tyr Glu Thr
                20                  25                  30 cgg att ggg ccg cat aac ggc gcg cgc gtc gtc gcc aag gcc tgg tcc     144
Arg Ile Gly Pro His Asn Gly Ala Arg Val Val Ala Lys Ala Trp Ser
            35                  40                  45 gac gcc gca ttc aag cga gcg ctg gtc gag gat gcg acc aag gcc gtg     192
Asp Ala Ala Phe Lys Arg Ala Leu Val Glu Asp Ala Thr Lys Ala Val
        50                  55                  60 cag tcg ttc ggc gtg gtc aat cgc gtc ggc gat cac ctg atc gcg gtc     240
Gln Ser Phe Gly Val Val Asn Arg Val Gly Asp His Leu Ile Ala Val
65                  70                  75                  80 gag aac acg ccc acg ctg cac aac atc atc gtg tgc acg ttg tgc tcc     288
Glu Asn Thr Pro Thr Leu His Asn Ile Ile Val Cys Thr Leu Cys Ser
                85                  90                  95 tgc tat ccg tgg gaa gtg ctc ggc ctg ccg ccg gtc tgg tac aaa tcg     336
```

```
gcg ccc tac cgc tcg cgc gcg gtc aac gac ccg cgc ggg gta ctc gcc    384
Ala Pro Tyr Arg Ser Arg Ala Val Asn Asp Pro Arg Gly Val Leu Ala
        115                 120                 125 gat ttc ggc ctg aag ctg gcg ccg gat atg caa atc cgt gtc tgg gat    432
Asp Phe Gly Leu Lys Leu Ala Pro Asp Met Gln Ile Arg Val Trp Asp
130                 135                 140 tcg acc gcc gag acg cgc ttc atc gtg ttg ccg atg cgc ccg gcc gga    480
Ser Thr Ala Glu Thr Arg Phe Ile Val Leu Pro Met Arg Pro Ala Gly
145                 150                 155                 160 acc gac ggc tgg agc gaa gaa aag ctc gcc gcg ctg gtg aca cgc gat    528
Thr Asp Gly Trp Ser Glu Glu Lys Leu Ala Ala Leu Val Thr Arg Asp
                165                 170                 175 tgc atg atc ggc acc ggc tta ccc aag caa ccc aac gag gtc acg taa    576
Cys Met Ile Gly Thr Gly Leu Pro Lys Gln Pro Asn Glu Val Thr
            180                 185                 190
```

```
<210> SEQ ID NO 48
<211> LENGTH: 191
<212> TYPE: PRT
<213> ORGANISM: Unknown
<220> FEATURE:
<223> OTHER INFORMATION: Metagenome - alpha unit nitrile hydratase -
      M23dA12

<400> SEQUENCE: 48
```

```
Met Gln Leu Arg Val Arg Ala Leu Glu Thr Val Leu Ala Glu Lys Gly
1               5                   10                  15

Tyr Leu Asp Pro Ala Ala Leu Asp Ala Met Ile Glu Ala Tyr Glu Thr
            20                  25                  30

Arg Ile Gly Pro His Asn Gly Ala Arg Val Val Ala Lys Ala Trp Ser
        35                  40                  45

Asp Ala Ala Phe Lys Arg Ala Leu Val Glu Asp Ala Thr Lys Ala Val
    50                  55                  60

Gln Ser Phe Gly Val Val Asn Arg Val Gly Asp His Leu Ile Ala Val
65                  70                  75                  80

Glu Asn Thr Pro Thr Leu His Asn Ile Ile Val Cys Thr Leu Cys Ser
                85                  90                  95

Cys Tyr Pro Trp Glu Val Leu Gly Leu Pro Pro Val Trp Tyr Lys Ser
            100                 105                 110

Ala Pro Tyr Arg Ser Arg Ala Val Asn Asp Pro Arg Gly Val Leu Ala
        115                 120                 125

Asp Phe Gly Leu Lys Leu Ala Pro Asp Met Gln Ile Arg Val Trp Asp
    130                 135                 140

Ser Thr Ala Glu Thr Arg Phe Ile Val Leu Pro Met Arg Pro Ala Gly
145                 150                 155                 160

Thr Asp Gly Trp Ser Glu Glu Lys Leu Ala Ala Leu Val Thr Arg Asp
                165                 170                 175

Cys Met Ile Gly Thr Gly Leu Pro Lys Gln Pro Asn Glu Val Thr
            180                 185                 190
```

```
<210> SEQ ID NO 49
<211> LENGTH: 624
<212> TYPE: DNA
<213> ORGANISM: Unknown
<220> FEATURE:
<223> OTHER INFORMATION: Metagenome - alpha unit nitrile hydratase -
      M49bD9
<220> FEATURE:
```

<210> SEQ ID NO 49
<211> LENGTH: 624
<212> TYPE: DNA
<213> ORGANISM: Unknown
<220> FEATURE:
<223> OTHER INFORMATION: Metagenome - alpha unit nitrile hydratase - M49bD9
<220> FEATURE:
<221> NAME/KEY: CDS
<222> LOCATION: (1)..(624)

<400> SEQUENCE: 49

```
atg agc gag cac gat tcc ggc gaa agc cat cac cat ccg cag cca cta    48
Met Ser Glu His Asp Ser Gly Glu Ser His His His Pro Gln Pro Leu
1               5                   10                  15 tcg cag gcg gca ttg cgc gcg aag gcg atc gaa tcg ctg ctg gtc gaa    96
Ser Gln Ala Ala Leu Arg Ala Lys Ala Ile Glu Ser Leu Leu Val Glu
            20                  25                  30 aag ggg ctg atc gcg acc gac gtg atc gat cgc gtg gta gca acg tac    144
Lys Gly Leu Ile Ala Thr Asp Val Ile Asp Arg Val Val Ala Thr Tyr
        35                  40                  45 gag aaa gaa gtc ggg ccg ctc aac ggc gct aaa gtc gtc gcg cgg gcc    192
Glu Lys Glu Val Gly Pro Leu Asn Gly Ala Lys Val Val Ala Arg Ala
    50                  55                  60 tgg acc gat ccg gag tac cgc cgc aga ctg ctc aag aac ggc acg gcg    240
Trp Thr Asp Pro Glu Tyr Arg Arg Arg Leu Leu Lys Asn Gly Thr Ala
65                  70                  75                  80 gcg att gcc gag ctg gga ttc ggc ggc ttg cag ggc gaa cac atg atg    288
Ala Ile Ala Glu Leu Gly Phe Gly Gly Leu Gln Gly Glu His Met Met
                85                  90                  95 gtc gtg gaa aac acg ccg tcc gta cat aac gtg atc tgt tgc acg cta    336
Val Val Glu Asn Thr Pro Ser Val His Asn Val Ile Cys Cys Thr Leu
            100                 105                 110 tgc tca tgc tat ccg tgg ccg gtc ctg gga ctt ccg ccg agc tgg tac    384
Cys Ser Cys Tyr Pro Trp Pro Val Leu Gly Leu Pro Pro Ser Trp Tyr
        115                 120                 125 aag tcg ctg gcg tat cgt tcg cga atc gtg cgc gag ccg cgc gcc gtc    432
Lys Ser Leu Ala Tyr Arg Ser Arg Ile Val Arg Glu Pro Arg Ala Val
    130                 135                 140 ctc ggc gaa ttc ggc ctc gaa ttg ccc gaa acg gtg gaa gtc cgc gta    480
Leu Gly Glu Phe Gly Leu Glu Leu Pro Glu Thr Val Glu Val Arg Val
145                 150                 155                 160 tgg gat agc agt gct gag atg cgc tat ctc gtg ttg ccg gag cgt cca    528
Trp Asp Ser Ser Ala Glu Met Arg Tyr Leu Val Leu Pro Glu Arg Pro
                165                 170                 175 gcg gga acg acg gag ttg agc gaa gcg gaa ttg gct tca ttg atc acg    576
Ala Gly Thr Thr Glu Leu Ser Glu Ala Glu Leu Ala Ser Leu Ile Thr
            180                 185                 190 cgc gat gcc ttg atc ggc gtg gcg aaa gtc gcg gcg cca agc cgc tag    624
Arg Asp Ala Leu Ile Gly Val Ala Lys Val Ala Ala Pro Ser Arg
        195                 200                 205
```

<210> SEQ ID NO 50
<211> LENGTH: 207
<212> TYPE: PRT
<213> ORGANISM: Unknown
<220> FEATURE:
<223> OTHER INFORMATION: Metagenome - alpha unit nitrile hydratase - M49bD9

<400> SEQUENCE: 50

```
Met Ser Glu His Asp Ser Gly Glu Ser His His His Pro Gln Pro Leu
1               5                   10                  15

Ser Gln Ala Ala Leu Arg Ala Lys Ala Ile Glu Ser Leu Leu Val Glu
            20                  25                  30

Lys Gly Leu Ile Ala Thr Asp Val Ile Asp Arg Val Val Ala Thr Tyr
        35                  40                  45

Glu Lys Glu Val Gly Pro Leu Asn Gly Ala Lys Val Val Ala Arg Ala
    50                  55                  60
```

```
Trp Thr Asp Pro Glu Tyr Arg Arg Arg Leu Leu Lys Asn Gly Thr Ala
 65                  70                  75                  80

Ala Ile Ala Glu Leu Gly Phe Gly Gly Leu Gln Gly Glu His Met Met
                 85                  90                  95

Val Val Glu Asn Thr Pro Ser Val His Asn Val Ile Cys Cys Thr Leu
            100                 105                 110

Cys Ser Cys Tyr Pro Trp Pro Val Leu Gly Leu Pro Pro Ser Trp Tyr
        115                 120                 125

Lys Ser Leu Ala Tyr Arg Ser Arg Ile Val Arg Glu Pro Arg Ala Val
    130                 135                 140

Leu Gly Glu Phe Gly Leu Glu Leu Pro Glu Thr Val Glu Val Arg Val
145                 150                 155                 160

Trp Asp Ser Ser Ala Glu Met Arg Tyr Leu Val Leu Pro Glu Arg Pro
                165                 170                 175

Ala Gly Thr Thr Glu Leu Ser Glu Ala Glu Leu Ala Ser Leu Ile Thr
            180                 185                 190

Arg Asp Ala Leu Ile Gly Val Ala Lys Val Ala Ala Pro Ser Arg
        195                 200                 205

<210> SEQ ID NO 51
<211> LENGTH: 600
<212> TYPE: DNA
<213> ORGANISM: Unknown
<220> FEATURE:
<223> OTHER INFORMATION: Metagenome - alpha unit nitrile hydratase -
      M6dE2
<220> FEATURE:
<221> NAME/KEY: CDS
<222> LOCATION: (1)..(600)

<400> SEQUENCE: 51 atg agc aac cca cgc cgt cga gaa cgg tcg gcc cca ccg gat gcg cga      48
Met Ser Asn Pro Arg Arg Glu Arg Ser Ala Pro Pro Asp Ala Arg
 1               5                  10                  15 gcc aag gcg ctc gca gaa gcg ctt tcg aag caa gga ctc gtg ccg gaa      96
Ala Lys Ala Leu Ala Glu Ala Leu Ser Lys Gln Gly Leu Val Pro Glu
             20                  25                  30 ggg ttc ctc gac cag gtc ggt tct cac gcc gcg gag gcg tgg agc ccg     144
Gly Phe Leu Asp Gln Val Gly Ser His Ala Ala Glu Ala Trp Ser Pro
         35                  40                  45 cga aac ggc gca cgg gtc gtg gcg cgg gcg tgg gtg gat ccc gag tac     192
Arg Asn Gly Ala Arg Val Val Ala Arg Ala Trp Val Asp Pro Glu Tyr
     50                  55                  60 cgg acg cgc ttg ctc gcc gac ggc acc gcc gcg tgc gcc gcg ctc ggc     240
Arg Thr Arg Leu Leu Ala Asp Gly Thr Ala Ala Cys Ala Ala Leu Gly
 65                  70                  75                  80 tac gcg gga ccg cag gga gag tac atc gtg gta ctc gaa gac acg ctg     288
Tyr Ala Gly Pro Gln Gly Glu Tyr Ile Val Val Leu Glu Asp Thr Leu
                 85                  90                  95 gcc gtt cac aac gtg atc gtg tgt acg caa tgc tcg tgt act gcg tgg     336
Ala Val His Asn Val Ile Val Cys Thr Gln Cys Ser Cys Thr Ala Trp
            100                 105                 110 ccc gtg ctg ggg ctg ccg ccc gat tgg tac aag agt ccg gag tat cgc     384
Pro Val Leu Gly Leu Pro Pro Asp Trp Tyr Lys Ser Pro Glu Tyr Arg
        115                 120                 125 gcc cgc gtc gtg cgg gag ccg cga cgg gtg ctt cgc gaa atg ggc ctc     432
Ala Arg Val Val Arg Glu Pro Arg Arg Val Leu Arg Glu Met Gly Leu
    130                 135                 140 gag cta tcc gag agc gtg acg atc cgc gtg tgg gat acg act gcg gaa     480
Glu Leu Ser Glu Ser Val Thr Ile Arg Val Trp Asp Thr Thr Ala Glu
```

```
Glu Leu Ser Glu Ser Val Thr Ile Arg Val Trp Asp Thr Thr Ala Glu
145                 150                 155                 160 acg cgc ttc ctg gtg ctg ccg ctt cgg ccg gcg gga acc gaa ggg tgg    528
Thr Arg Phe Leu Val Leu Pro Leu Arg Pro Ala Gly Thr Glu Gly Trp
                165                 170                 175 agc gcg gag cag ctc gcg tcg ctc gtc acg cgc gag gcg atg atc ggc    576
Ser Ala Glu Gln Leu Ala Ser Leu Val Thr Arg Glu Ala Met Ile Gly
            180                 185                 190 gtg gcg cgg gtc gag gtg gtg tag                                    600
Val Ala Arg Val Glu Val Val
        195
```

```
<210> SEQ ID NO 52
<211> LENGTH: 199
<212> TYPE: PRT
<213> ORGANISM: Unknown
<220> FEATURE:
<223> OTHER INFORMATION: Metagenome - alpha unit nitrile hydratase -
      M6dE2

<400> SEQUENCE: 52
```

```
Met Ser Asn Pro Arg Arg Glu Arg Ser Ala Pro Pro Asp Ala Arg
1               5                   10                  15

Ala Lys Ala Leu Ala Glu Ala Leu Ser Lys Gln Gly Leu Val Pro Glu
            20                  25                  30

Gly Phe Leu Asp Gln Val Gly Ser His Ala Ala Glu Ala Trp Ser Pro
        35                  40                  45

Arg Asn Gly Ala Arg Val Ala Arg Ala Trp Val Asp Pro Glu Tyr
    50                  55                  60

Arg Thr Arg Leu Leu Ala Asp Gly Thr Ala Ala Cys Ala Ala Leu Gly
65                  70                  75                  80

Tyr Ala Gly Pro Gln Gly Glu Tyr Ile Val Val Leu Glu Asp Thr Leu
                85                  90                  95

Ala Val His Asn Val Ile Val Cys Thr Gln Cys Ser Cys Thr Ala Trp
            100                 105                 110

Pro Val Leu Gly Leu Pro Pro Asp Trp Tyr Lys Ser Pro Glu Tyr Arg
        115                 120                 125

Ala Arg Val Val Arg Glu Pro Arg Arg Val Leu Arg Glu Met Gly Leu
    130                 135                 140

Glu Leu Ser Glu Ser Val Thr Ile Arg Val Trp Asp Thr Thr Ala Glu
145                 150                 155                 160

Thr Arg Phe Leu Val Leu Pro Leu Arg Pro Ala Gly Thr Glu Gly Trp
                165                 170                 175

Ser Ala Glu Gln Leu Ala Ser Leu Val Thr Arg Glu Ala Met Ile Gly
            180                 185                 190

Val Ala Arg Val Glu Val Val
        195
```

```
<210> SEQ ID NO 53
<211> LENGTH: 645
<212> TYPE: DNA
<213> ORGANISM: Unknown
<220> FEATURE:
<223> OTHER INFORMATION: Metagenome - alpha unit nitrile hydratase -
      M25A18
<220> FEATURE:
<221> NAME/KEY: CDS
<222> LOCATION: (1)..(645)

<400> SEQUENCE: 53
```

-continued

| | |
|---|---|
| atg agc ggc acg cat cac cac gac cat gac cac gat cat gac cat gcc<br>Met Ser Gly Thr His His His Asp His Asp His Asp His Asp His Ala<br>1               5                      10                  15 | 48 |
| cat ccg ggc gtc gcc aag gac gag aag gtc cac ggc tat tac caa ttg<br>His Pro Gly Val Ala Lys Asp Glu Lys Val His Gly Tyr Tyr Gln Leu<br>                    20                   25                   30 | 96 |
| ctc ggc ctc gcc atc aaa gag ctg ctg atc gaa aaa ggc gtc atc acc<br>Leu Gly Leu Ala Ile Lys Glu Leu Leu Ile Glu Lys Gly Val Ile Thr<br>        35                    40                   45 | 144 |
| gcc gcc gag gtg cgc caa gcg atc gag gcg cgc gac gcg atc acg ccg<br>Ala Ala Glu Val Arg Gln Ala Ile Glu Ala Arg Asp Ala Ile Thr Pro<br>50                      55                    60 | 192 |
| tcg ctc ggc ggc aag gtg gtc gcg cgc gcc tgg acc gat ccg gcc tac<br>Ser Leu Gly Gly Lys Val Val Ala Arg Ala Trp Thr Asp Pro Ala Tyr<br>65                      70                   75                  80 | 240 |
| aag gcg cgg ctg atc gcc gat ccc gcc gcc gcc atg atg gag atg ggc<br>Lys Ala Arg Leu Ile Ala Asp Pro Ala Ala Ala Met Met Glu Met Gly<br>                    85                   90                  95 | 288 |
| gtc gat ctc ggc ccc acc gga ctc gcc atc gcc gag aac acg ccg gag<br>Val Asp Leu Gly Pro Thr Gly Leu Ala Ile Ala Glu Asn Thr Pro Glu<br>                  100                  105               110 | 336 |
| gcg cac aac gtc atc gtc tgc acc ctg tgc tcg tgc tat ccg cgc gcc<br>Ala His Asn Val Ile Val Cys Thr Leu Cys Ser Cys Tyr Pro Arg Ala<br>115                    120                  125 | 384 |
| gtg ctc ggc ctg ccg ccc tcc tgg tac aag gac cgc gat tac cgg tcg<br>Val Leu Gly Leu Pro Pro Ser Trp Tyr Lys Asp Arg Asp Tyr Arg Ser<br>130                    135                  140 | 432 |
| cgc gtg gtg cgc gag ccg cgc gcc gtg ctc aag gag ttc ggc acg gaa<br>Arg Val Val Arg Glu Pro Arg Ala Val Leu Lys Glu Phe Gly Thr Glu<br>145                    150                  155               160 | 480 |
| ttg ccc gac gac gtc gac gtc cgc gtc cac gat tcg acc gcc gat ctg<br>Leu Pro Asp Asp Val Asp Val Arg Val His Asp Ser Thr Ala Asp Leu<br>                  165                  170               175 | 528 |
| cgc tat ctc gtg ctg ccg atg cgc ccg gcc ggc acc gag ggc atg agc<br>Arg Tyr Leu Val Leu Pro Met Arg Pro Ala Gly Thr Glu Gly Met Ser<br>                180                  185               190 | 576 |
| gag gcg gag ctg gcc gag atc gtg acg cgc gac tgc atg atc ggc gtg<br>Glu Ala Glu Leu Ala Glu Ile Val Thr Arg Asp Cys Met Ile Gly Val<br>        195                    200                  205 | 624 |
| acg gtg ccg aaa gcg ccc taa<br>Thr Val Pro Lys Ala Pro<br>      210 | 645 |

```
<210> SEQ ID NO 54
<211> LENGTH: 214
<212> TYPE: PRT
<213> ORGANISM: Unknown
<220> FEATURE:
<223> OTHER INFORMATION: Metagenome - alpha unit nitrile hydratase -
      M25A18

<400> SEQUENCE: 54
```

Met Ser Gly Thr His His His Asp His Asp His Asp His Asp His Ala
1               5                      10                  15

His Pro Gly Val Ala Lys Asp Glu Lys Val His Gly Tyr Tyr Gln Leu
                    20                   25                   30

Leu Gly Leu Ala Ile Lys Glu Leu Leu Ile Glu Lys Gly Val Ile Thr
        35                    40                   45

Ala Ala Glu Val Arg Gln Ala Ile Glu Ala Arg Asp Ala Ile Thr Pro
50                    55                    60

```
Ser Leu Gly Gly Lys Val Val Ala Arg Ala Trp Thr Asp Pro Ala Tyr
 65                  70                  75                  80

Lys Ala Arg Leu Ile Ala Asp Pro Ala Ala Met Met Glu Met Gly
                 85                  90                  95

Val Asp Leu Gly Pro Thr Gly Leu Ala Ile Ala Glu Asn Thr Pro Glu
            100                 105                 110

Ala His Asn Val Ile Val Cys Thr Leu Cys Ser Cys Tyr Pro Arg Ala
            115                 120                 125

Val Leu Gly Leu Pro Pro Ser Trp Tyr Lys Asp Arg Asp Tyr Arg Ser
        130                 135                 140

Arg Val Val Arg Glu Pro Arg Ala Val Leu Lys Glu Phe Gly Thr Glu
145                 150                 155                 160

Leu Pro Asp Asp Val Asp Val Arg Val His Asp Ser Thr Ala Asp Leu
                165                 170                 175

Arg Tyr Leu Val Leu Pro Met Arg Pro Ala Gly Thr Glu Gly Met Ser
            180                 185                 190

Glu Ala Glu Leu Ala Glu Ile Val Thr Arg Asp Cys Met Ile Gly Val
        195                 200                 205

Thr Val Pro Lys Ala Pro
        210

<210> SEQ ID NO 55
<211> LENGTH: 627
<212> TYPE: DNA
<213> ORGANISM: Unknown
<220> FEATURE:
<223> OTHER INFORMATION: Metagenome - alpha unit nitrile hydratase
<220> FEATURE:
<221> NAME/KEY: CDS
<222> LOCATION: (1)..(627)

<400> SEQUENCE: 55 atg agc ggt cac cat cac gac cac gac cat gag cac gac aac cac ttc     48
Met Ser Gly His His His Asp His Asp His Glu His Asp Asn His Phe
  1               5                  10                  15 acg ccg atc gaa gcg cgc gtg aag gcg ctg gaa tcg ctg ctg gtc gcc     96
Thr Pro Ile Glu Ala Arg Val Lys Ala Leu Glu Ser Leu Leu Val Ala
             20                  25                  30 aag ggc tat gtc gat ccc gcc gcg ctc gat gcg atc atc gac acc tat    144
Lys Gly Tyr Val Asp Pro Ala Ala Leu Asp Ala Ile Ile Asp Thr Tyr
         35                  40                  45 gag acg aag atc ggc ccg cgc aac ggc gcc cgc gtc gtc gcc aag gcc    192
Glu Thr Lys Ile Gly Pro Arg Asn Gly Ala Arg Val Val Ala Lys Ala
     50                  55                  60 tgg acc gat ccg gaa ttc gcg gcg cgg ctc aag cag gat ggc agc gcc    240
Trp Thr Asp Pro Glu Phe Ala Ala Arg Leu Lys Gln Asp Gly Ser Ala
 65                  70                  75                  80 gcc gtc gcc gaa ctc ggc tat ggc ggg cgt ggc ggc gag cat atc gtc    288
Ala Val Ala Glu Leu Gly Tyr Gly Gly Arg Gly Gly Glu His Ile Val
                 85                  90                  95 gcc tgt ttc aat acg ccc gaa gag cac aac ctg atc gtc tgc acg ctc    336
Ala Cys Phe Asn Thr Pro Glu Glu His Asn Leu Ile Val Cys Thr Leu
            100                 105                 110 tgc tcg tgc tat ccc tgg ccg gtg ctc ggc ctg ccg ccg gtc tgg tac    384
Cys Ser Cys Tyr Pro Trp Pro Val Leu Gly Leu Pro Pro Val Trp Tyr
        115                 120                 125 aaa tcc ccg ccc tat cgc tcg aaa gcg gtg atc gac ccg cgc ggc gtg    432
Lys Ser Pro Pro Tyr Arg Ser Lys Ala Val Ile Asp Pro Arg Gly Val
    130                 135                 140
```

```
ctg gcc gat ttc ggc gtg acc ctg ccg gag gga caa agg atc cgc gtc    480
Leu Ala Asp Phe Gly Val Thr Leu Pro Glu Gly Gln Arg Ile Arg Val
145                 150                 155                 160 tgg gat tcc acc gcc gaa acc cgc ttc att gtc atc ccc ctg cgc ccg    528
Trp Asp Ser Thr Ala Glu Thr Arg Phe Ile Val Ile Pro Leu Arg Pro
                165                 170                 175 gcc ggg acg gaa ggc tgg tcg gaa gaa cag ctg gcg gcg atc gtg acg    576
Ala Gly Thr Glu Gly Trp Ser Glu Glu Gln Leu Ala Ala Ile Val Thr
            180                 185                 190 cgt gac agc atg atc ggc acc ggc gtg gtc agc gcg gag gct tcg cga    624
Arg Asp Ser Met Ile Gly Thr Gly Val Val Ser Ala Glu Ala Ser Arg
        195                 200                 205 tga                                                                 627
```

```
<210> SEQ ID NO 56
<211> LENGTH: 208
<212> TYPE: PRT
<213> ORGANISM: Unknown
<220> FEATURE:
<223> OTHER INFORMATION: Metagenome - alpha unit nitrile hydratase

<400> SEQUENCE: 56
```

```
Met Ser Gly His His Asp His Asp His Glu His Asp Asn His Phe
1               5                   10                  15

Thr Pro Ile Glu Ala Arg Val Lys Ala Leu Glu Ser Leu Leu Val Ala
                20                  25                  30

Lys Gly Tyr Val Asp Pro Ala Ala Leu Asp Ala Ile Ile Asp Thr Tyr
            35                  40                  45

Glu Thr Lys Ile Gly Pro Arg Asn Gly Ala Arg Val Val Ala Lys Ala
        50                  55                  60

Trp Thr Asp Pro Glu Phe Ala Ala Arg Leu Lys Gln Asp Gly Ser Ala
65                  70                  75                  80

Ala Val Ala Glu Leu Gly Tyr Gly Gly Arg Gly Gly Glu His Ile Val
                85                  90                  95

Ala Cys Phe Asn Thr Pro Glu Glu His Asn Leu Ile Val Cys Thr Leu
            100                 105                 110

Cys Ser Cys Tyr Pro Trp Pro Val Leu Gly Leu Pro Pro Val Trp Tyr
        115                 120                 125

Lys Ser Pro Pro Tyr Arg Ser Lys Ala Val Ile Asp Pro Arg Gly Val
    130                 135                 140

Leu Ala Asp Phe Gly Val Thr Leu Pro Glu Gly Gln Arg Ile Arg Val
145                 150                 155                 160

Trp Asp Ser Thr Ala Glu Thr Arg Phe Ile Val Ile Pro Leu Arg Pro
                165                 170                 175

Ala Gly Thr Glu Gly Trp Ser Glu Glu Gln Leu Ala Ala Ile Val Thr
            180                 185                 190

Arg Asp Ser Met Ile Gly Thr Gly Val Val Ser Ala Glu Ala Ser Arg
        195                 200                 205
```

```
<210> SEQ ID NO 57
<211> LENGTH: 696
<212> TYPE: DNA
<213> ORGANISM: Unknown
<220> FEATURE:
<223> OTHER INFORMATION: Metagenome - alpha unit nitrile hydratase -
      M3aG10
<220> FEATURE:
<221> NAME/KEY: CDS
<222> LOCATION: (1)..(696)
```

<400> SEQUENCE: 57

```
atg gat cca acg agg cgt agt ttc ctg gcg tct acc gtt gcc ctg acc     48
Met Asp Pro Thr Arg Arg Ser Phe Leu Ala Ser Thr Val Ala Leu Thr
1               5                   10                  15 ggc ggc gca gct atc ccc gat ctg gct cat gcg gca gac cac gac cac     96
Gly Gly Ala Ala Ile Pro Asp Leu Ala His Ala Ala Asp His Asp His
            20                  25                  30 cag cat caa gat ttg ccg tcc gat ctg gcg ctg cgg gtg aag tcg ctc    144
Gln His Gln Asp Leu Pro Ser Asp Leu Ala Leu Arg Val Lys Ser Leu
        35                  40                  45 gaa tcg ctg ctt gtc gag aag ggg ctg gtg gag cga gca gcg ctc gac    192
Glu Ser Leu Leu Val Glu Lys Gly Leu Val Glu Arg Ala Ala Leu Asp
50                  55                  60 gcg ctg gtg gac acc tac gag cac aaa gtc ggg ccg cga aac gga gcg    240
Ala Leu Val Asp Thr Tyr Glu His Lys Val Gly Pro Arg Asn Gly Ala
65                  70                  75                  80 cgc gtt gtc gcg cgg gcc tgg gtt gac ccg gac tac aag caa cgg tta    288
Arg Val Val Ala Arg Ala Trp Val Asp Pro Asp Tyr Lys Gln Arg Leu
                85                  90                  95 ttc gcg aac ggt acc gcc gca gtc gcg gag ttc ggc tac tcc ggc tcg    336
Phe Ala Asn Gly Thr Ala Ala Val Ala Glu Phe Gly Tyr Ser Gly Ser
            100                 105                 110 cag ggc gct gac atc cgg gtc gtc gaa aac acg gcc act gta cat aac    384
Gln Gly Ala Asp Ile Arg Val Val Glu Asn Thr Ala Thr Val His Asn
        115                 120                 125 ctc gtc gtg tgc acg ctg tgc tct tgt tat ccc tgg ccg gtg ctg ggc    432
Leu Val Val Cys Thr Leu Cys Ser Cys Tyr Pro Trp Pro Val Leu Gly
    130                 135                 140 ttg ccg ccg gtc tgg tac aag tcc gcg ccc tat cgg tct cgc gtg gtg    480
Leu Pro Pro Val Trp Tyr Lys Ser Ala Pro Tyr Arg Ser Arg Val Val
145                 150                 155                 160 atc gat ccg cga ggt gtg ctg cgc gag ttc ggc gtg gtg ctg ccg gac    528
Ile Asp Pro Arg Gly Val Leu Arg Glu Phe Gly Val Val Leu Pro Asp
                165                 170                 175 cat atc gaa gtg cgt gtc tat gac agc acg gcg gag caa cgc tat cta    576
His Ile Glu Val Arg Val Tyr Asp Ser Thr Ala Glu Gln Arg Tyr Leu
            180                 185                 190 gtg ctg ccg gag cgg ccg gcc gga acc gaa aac ctg aca gaa gaa gcg    624
Val Leu Pro Glu Arg Pro Ala Gly Thr Glu Asn Leu Thr Glu Glu Ala
        195                 200                 205 ctg gcg ctg ctg gtg acg cgc gac gcg atg att ggc gtg gcc aag gtc    672
Leu Ala Leu Leu Val Thr Arg Asp Ala Met Ile Gly Val Ala Lys Val
    210                 215                 220 gcg ccg ccg gga ggc cgc gga tga                                    696
Ala Pro Pro Gly Gly Arg Gly
225                 230
```

<210> SEQ ID NO 58
<211> LENGTH: 231
<212> TYPE: PRT
<213> ORGANISM: Unknown
<220> FEATURE:
<223> OTHER INFORMATION: Metagenome - alpha unit nitrile hydratase - M3aG10

<400> SEQUENCE: 58

```
Met Asp Pro Thr Arg Arg Ser Phe Leu Ala Ser Thr Val Ala Leu Thr
1               5                   10                  15

Gly Gly Ala Ala Ile Pro Asp Leu Ala His Ala Ala Asp His Asp His
            20                  25                  30
```

```
Gln His Gln Asp Leu Pro Ser Asp Leu Ala Leu Arg Val Lys Ser Leu
        35                  40                  45

Glu Ser Leu Leu Val Glu Lys Gly Leu Val Glu Arg Ala Ala Leu Asp
 50                  55                  60

Ala Leu Val Asp Thr Tyr Glu His Lys Val Gly Pro Arg Asn Gly Ala
 65                  70                  75                  80

Arg Val Val Ala Arg Ala Trp Val Asp Pro Asp Tyr Lys Gln Arg Leu
                 85                  90                  95

Phe Ala Asn Gly Thr Ala Val Ala Glu Phe Gly Tyr Ser Gly Ser
                100                 105                 110

Gln Gly Ala Asp Ile Arg Val Glu Asn Thr Ala Thr Val His Asn
            115                 120                 125

Leu Val Val Cys Thr Leu Cys Ser Cys Tyr Pro Trp Pro Val Leu Gly
    130                 135                 140

Leu Pro Pro Val Trp Tyr Lys Ser Ala Pro Tyr Arg Ser Arg Val Val
145                 150                 155                 160

Ile Asp Pro Arg Gly Val Leu Arg Glu Phe Gly Val Val Leu Pro Asp
                165                 170                 175

His Ile Glu Val Arg Val Tyr Asp Ser Thr Ala Glu Gln Arg Tyr Leu
            180                 185                 190

Val Leu Pro Glu Arg Pro Ala Gly Thr Glu Asn Leu Thr Glu Glu Ala
        195                 200                 205

Leu Ala Leu Leu Val Thr Arg Asp Ala Met Ile Gly Val Ala Lys Val
    210                 215                 220

Ala Pro Pro Gly Gly Arg Gly
225                 230

<210> SEQ ID NO 59
<211> LENGTH: 609
<212> TYPE: DNA
<213> ORGANISM: Unknown
<220> FEATURE:
<223> OTHER INFORMATION: Metagenome - alpha unit nitrile hydratase -
      M73dC9
<220> FEATURE:
<221> NAME/KEY: CDS
<222> LOCATION: (1)..(609)

<400> SEQUENCE: 59 atg agc tcg aag ccc acc gaa gat ctc ggc acc tac cag ccg ctc acc      48
Met Ser Ser Lys Pro Thr Glu Asp Leu Gly Thr Tyr Gln Pro Leu Thr
 1               5                  10                  15 tac tac cag atg atg gaa gtg agc ctg cgc gag ctg ctg gtg gag aag      96
Tyr Tyr Gln Met Met Glu Val Ser Leu Arg Glu Leu Leu Val Glu Lys
                 20                  25                  30 ggc gtg atc acc gaa gcg gaa gtc gcc cgc gcg atg ggc gag atc ggc     144
Gly Val Ile Thr Glu Ala Glu Val Ala Arg Ala Met Gly Glu Ile Gly
             35                  40                  45 gcg aga agc ccg gag cgc ggc gcg aag atg gtc gcg cgc gcg tgg gtg     192
Ala Arg Ser Pro Glu Arg Gly Ala Lys Met Val Ala Arg Ala Trp Val
 50                  55                  60 gac ccg gcg tac aag gcg cgc atg ctt gcc gac ggc agc aag gcc gcc     240
Asp Pro Ala Tyr Lys Ala Arg Met Leu Ala Asp Gly Ser Lys Ala Ala
 65                  70                  75                  80 gag gag ctc ggg ttc gag gtg ccg ggc ctc aag ctg atc gtg gtc gag     288
Glu Glu Leu Gly Phe Glu Val Pro Gly Leu Lys Leu Ile Val Val Glu
                 85                  90                  95 aac acc gcg gac acg cac aac gtg gtc gtg tgc acg ctg tgc tcg tgc     336
Asn Thr Ala Asp Thr His Asn Val Val Val Cys Thr Leu Cys Ser Cys
```

```
                100                   105                   110
tac ccg cgc atc ctg ctc ggc atc ccg ccc gag tgg tac aag tcg cgc        384
Tyr Pro Arg Ile Leu Leu Gly Ile Pro Pro Glu Trp Tyr Lys Ser Arg
        115                 120                 125 agc tac cgc agc cgc aca gtg cgc gag ccg cgc gcg gtg ctc gcc gaa        432
Ser Tyr Arg Ser Arg Thr Val Arg Glu Pro Arg Ala Val Leu Ala Glu
    130                 135                 140 ttc ggc acg acc atc ccg gag aac gtc gcg atc cga gtg cac gac agc        480
Phe Gly Thr Thr Ile Pro Glu Asn Val Ala Ile Arg Val His Asp Ser
145                 150                 155                 160 act gcg gac atg cgc tac ctc gtg atg ccg atg cgg cct gcg ggc acc        528
Thr Ala Asp Met Arg Tyr Leu Val Met Pro Met Arg Pro Ala Gly Thr
                165                 170                 175 gaa aat ttc acc gaa gag cag ctc gct gca ttg gtg acg cgc gac agc        576
Glu Asn Phe Thr Glu Glu Gln Leu Ala Ala Leu Val Thr Arg Asp Ser
            180                 185                 190 ctg atc ggt gtt tcc tta gca acg ctt ccg tag                            609
Leu Ile Gly Val Ser Leu Ala Thr Leu Pro
        195                 200

<210> SEQ ID NO 60
<211> LENGTH: 202
<212> TYPE: PRT
<213> ORGANISM: Unknown
<220> FEATURE:
<223> OTHER INFORMATION: Metagenome - alpha unit nitrile hydratase -
      M73dC9

<400> SEQUENCE: 60

Met Ser Ser Lys Pro Thr Glu Asp Leu Gly Thr Tyr Gln Pro Leu Thr
1               5                   10                  15

Tyr Tyr Gln Met Met Glu Val Ser Leu Arg Glu Leu Leu Val Glu Lys
            20                  25                  30

Gly Val Ile Thr Glu Ala Glu Val Ala Arg Ala Met Gly Glu Ile Gly
        35                  40                  45

Ala Arg Ser Pro Glu Arg Gly Ala Lys Met Val Ala Arg Ala Trp Val
    50                  55                  60

Asp Pro Ala Tyr Lys Ala Arg Met Leu Ala Asp Gly Ser Lys Ala Ala
65                  70                  75                  80

Glu Glu Leu Gly Phe Glu Val Pro Gly Leu Lys Leu Ile Val Val Glu
                85                  90                  95

Asn Thr Ala Asp Thr His Asn Val Val Val Cys Thr Leu Cys Ser Cys
            100                 105                 110

Tyr Pro Arg Ile Leu Leu Gly Ile Pro Pro Glu Trp Tyr Lys Ser Arg
        115                 120                 125

Ser Tyr Arg Ser Arg Thr Val Arg Glu Pro Arg Ala Val Leu Ala Glu
    130                 135                 140

Phe Gly Thr Thr Ile Pro Glu Asn Val Ala Ile Arg Val His Asp Ser
145                 150                 155                 160

Thr Ala Asp Met Arg Tyr Leu Val Met Pro Met Arg Pro Ala Gly Thr
                165                 170                 175

Glu Asn Phe Thr Glu Glu Gln Leu Ala Ala Leu Val Thr Arg Asp Ser
            180                 185                 190

Leu Ile Gly Val Ser Leu Ala Thr Leu Pro
        195                 200

<210> SEQ ID NO 61
<211> LENGTH: 825
```

```
<212> TYPE: DNA
<213> ORGANISM: Unknown
<220> FEATURE:
<223> OTHER INFORMATION: Metagenome - beta unit nitrile hydratase
<220> FEATURE:
<221> NAME/KEY: CDS
<222> LOCATION: (1)..(825)

<400> SEQUENCE: 61 atg gtg gga cgt ggg aag tgg gca ctt ggc agt agg cag ttt gct gcg      48
Met Val Gly Arg Gly Lys Trp Ala Leu Gly Ser Arg Gln Phe Ala Ala
1               5                   10                  15 gct gcc aac tgg caa ctt atc agt cgc cct tca tgg tca gct tgt aat      96
Ala Ala Asn Trp Gln Leu Ile Ser Arg Pro Ser Trp Ser Ala Cys Asn
            20                  25                  30 ata ttg gtc ctc atg agc gcc acg cac ccc aaa aag cgc gcc gcc gac     144
Ile Leu Val Leu Met Ser Ala Thr His Pro Lys Lys Arg Ala Ala Asp
        35                  40                  45 atc ggc ggc aac aaa gcc ggc gcg gtg gac acc gcg gat cac ggc atg     192
Ile Gly Gly Asn Lys Ala Gly Ala Val Asp Thr Ala Asp His Gly Met
    50                  55                  60 aag ttc tgg gag cgg cag gcc aac gcc ctg cgc acc gcg ctg cgg cgc     240
Lys Phe Trp Glu Arg Gln Ala Asn Ala Leu Arg Thr Ala Leu Arg Arg
65                  70                  75                  80 aat gga ctg atg agc gta gat gag ctg cgc cgc gca gcg gag gac ctg     288
Asn Gly Leu Met Ser Val Asp Glu Leu Arg Arg Ala Ala Glu Asp Leu
                85                  90                  95 gga gac cgc tac gcg aag ctt gag tac ttc gag cgc acg acg ttc gcg     336
Gly Asp Arg Tyr Ala Lys Leu Glu Tyr Phe Glu Arg Thr Thr Phe Ala
            100                 105                 110 ctg cgc acg gtc ctg ctc gaa aag ggc tac ttc acg gag gag tcg ctc     384
Leu Arg Thr Val Leu Leu Glu Lys Gly Tyr Phe Thr Glu Glu Ser Leu
        115                 120                 125 gcg gcg aag atg gcc gag gtg cgg aag ccg ctt cga tgt gcc gcg caa     432
Ala Ala Lys Met Ala Glu Val Arg Lys Pro Leu Arg Cys Ala Ala Gln
    130                 135                 140 gaa gga att gcc ggt gaa gaa gaa agt gaa gcg atg aac cca gcg acg     480
Glu Gly Ile Ala Gly Glu Glu Glu Ser Glu Ala Met Asn Pro Ala Thr
145                 150                 155                 160 ggc aag cag gac ggc caa cgg ctg cca tct acg tat acc gcg gcg ccc     528
Gly Lys Gln Asp Gly Gln Arg Leu Pro Ser Thr Tyr Thr Ala Ala Pro
                165                 170                 175 ggg cac cga ttc gat gtc ggt gac cgc gtt gtg gtc aag cgc tca aat     576
Gly His Arg Phe Asp Val Gly Asp Arg Val Val Val Lys Arg Ser Asn
            180                 185                 190 ccg ccc ggc cac cgc cgc acg cct cat tac atc cgc ggc aag acg ggc     624
Pro Pro Gly His Arg Arg Thr Pro His Tyr Ile Arg Gly Lys Thr Gly
        195                 200                 205 gtg atc gag cgc atc tgc ggc gcc ttc ccc aac ccg gaa gag ctg gca     672
Val Ile Glu Arg Ile Cys Gly Ala Phe Pro Asn Pro Glu Glu Leu Ala
    210                 215                 220 tac gga ttc gac ggc gaa ccg aag aag gtg ctc tac cgc gtg cga ttc     720
Tyr Gly Phe Asp Gly Glu Pro Lys Lys Val Leu Tyr Arg Val Arg Phe
225                 230                 235                 240 cgg caa aaa gag gtg tgg ccg gcc tat cgc ggc ccg gcg cac gac gtg     768
Arg Gln Lys Glu Val Trp Pro Ala Tyr Arg Gly Pro Ala His Asp Val
                245                 250                 255 atc gag atg gag att ttc gag cat tgg ctc gag ccg gcg cag agc cag     816
Ile Glu Met Glu Ile Phe Glu His Trp Leu Glu Pro Ala Gln Ser Gln
            260                 265                 270 aaa acc tga                                                         825
```

Lys Thr

<210> SEQ ID NO 62
<211> LENGTH: 274
<212> TYPE: PRT
<213> ORGANISM: Unknown
<220> FEATURE:
<223> OTHER INFORMATION: Metagenome - beta unit nitrile hydratase

<400> SEQUENCE: 62

Met Val Gly Arg Gly Lys Trp Ala Leu Gly Ser Arg Gln Phe Ala Ala
1               5                   10                  15

Ala Ala Asn Trp Gln Leu Ile Ser Arg Pro Ser Trp Ser Ala Cys Asn
            20                  25                  30

Ile Leu Val Leu Met Ser Ala Thr His Pro Lys Lys Arg Ala Ala Asp
        35                  40                  45

Ile Gly Gly Asn Lys Ala Gly Ala Val Asp Thr Ala Asp His Gly Met
    50                  55                  60

Lys Phe Trp Glu Arg Gln Ala Asn Ala Leu Arg Thr Ala Leu Arg Arg
65                  70                  75                  80

Asn Gly Leu Met Ser Val Asp Glu Leu Arg Ala Ala Glu Asp Leu
                85                  90                  95

Gly Asp Arg Tyr Ala Lys Leu Glu Tyr Phe Glu Arg Thr Thr Phe Ala
            100                 105                 110

Leu Arg Thr Val Leu Leu Glu Lys Gly Tyr Phe Thr Glu Glu Ser Leu
        115                 120                 125

Ala Ala Lys Met Ala Glu Val Arg Lys Pro Leu Arg Cys Ala Ala Gln
    130                 135                 140

Glu Gly Ile Ala Gly Glu Glu Ser Glu Ala Met Asn Pro Ala Thr
145                 150                 155                 160

Gly Lys Gln Asp Gly Gln Arg Leu Pro Ser Thr Tyr Thr Ala Ala Pro
                165                 170                 175

Gly His Arg Phe Asp Val Gly Asp Arg Val Val Lys Arg Ser Asn
            180                 185                 190

Pro Pro Gly His Arg Arg Thr Pro His Tyr Ile Arg Gly Lys Thr Gly
        195                 200                 205

Val Ile Glu Arg Ile Cys Gly Ala Phe Pro Asn Pro Glu Glu Leu Ala
    210                 215                 220

Tyr Gly Phe Asp Gly Glu Pro Lys Lys Val Leu Tyr Arg Val Arg Phe
225                 230                 235                 240

Arg Gln Lys Glu Val Trp Pro Ala Tyr Arg Gly Pro Ala His Asp Val
                245                 250                 255

Ile Glu Met Glu Ile Phe Glu His Trp Leu Gly Pro Ala Gln Ser Gln
            260                 265                 270

Lys Thr

<210> SEQ ID NO 63
<211> LENGTH: 627
<212> TYPE: DNA
<213> ORGANISM: Unknown
<220> FEATURE:
<223> OTHER INFORMATION: Metagenome - beta unit nitrile hydratase -
      M12K24
<220> FEATURE:
<221> NAME/KEY: CDS
<222> LOCATION: (1)..(627)

<400> SEQUENCE: 63

```
atg gac ggc atg cac gac ctg gga ggc agg cag ggc ttc gga ccg gtt      48
Met Asp Gly Met His Asp Leu Gly Gly Arg Gln Gly Phe Gly Pro Val
1               5                   10                  15 cgc tac acg atc gac gcg ccc gca ttc cat tcg ccg tgg gaa gtg cgc      96
Arg Tyr Thr Ile Asp Ala Pro Ala Phe His Ser Pro Trp Glu Val Arg
                20                  25                  30 gcg aat tcg ctc tat gcg ttc gcg gtg cgc ctc ggc atc ttc aac atg     144
Ala Asn Ser Leu Tyr Ala Phe Ala Val Arg Leu Gly Ile Phe Asn Met
            35                  40                  45 gac gaa tac cgc cat gcg atc gag cgg atg gag ccg cgc cat tac ctc     192
Asp Glu Tyr Arg His Ala Ile Glu Arg Met Glu Pro Arg His Tyr Leu
        50                  55                  60 ggc gcc ggc tat tac gaa cgc tcg ttg acc ggc ctc gcg acc ttg ctg     240
Gly Ala Gly Tyr Tyr Glu Arg Ser Leu Thr Gly Leu Ala Thr Leu Leu
65                  70                  75                  80 gtc gag aag ggc gtc gtg acg cgc gag gaa ctc gag acc cgg gcg cag     288
Val Glu Lys Gly Val Val Thr Arg Glu Glu Leu Glu Thr Arg Ala Gln
                85                  90                  95 ggc cgc tac ccg ctg gcg atg ccc agc gcg cct ggc cgc acc aat gcg     336
Gly Arg Tyr Pro Leu Ala Met Pro Ser Ala Pro Gly Arg Thr Asn Ala
                100                 105                 110 cag gca cgc gag cgt ttc cag ccg ggc gac cgg gtt cgc gtc aag gcg     384
Gln Ala Arg Glu Arg Phe Gln Pro Gly Asp Arg Val Arg Val Lys Ala
            115                 120                 125 gat ttc gtg tcg ggg cac gtg cgg atg ccg gcg tac atc cgc ggc aag     432
Asp Phe Val Ser Gly His Val Arg Met Pro Ala Tyr Ile Arg Gly Lys
        130                 135                 140 acc ggc gtg gtc gtc agc gag tcc ccg gac tat ccg ttt ccc gat gcg     480
Thr Gly Val Val Val Ser Glu Ser Pro Asp Tyr Pro Phe Pro Asp Ala
145                 150                 155                 160 cat gcg cac tcg gtc gat gcc cag gac gag cca acc tac gac gtg cgc     528
His Ala His Ser Val Asp Ala Gln Asp Glu Pro Thr Tyr Asp Val Arg
                165                 170                 175 ttc cgc agc gag gat cta tgg ccg gat tcc gcc gat tcc gca ctc gtt     576
Phe Arg Ser Glu Asp Leu Trp Pro Asp Ser Ala Asp Ser Ala Leu Val
                180                 185                 190 cac gtc ggc gta ttc cag agc tac ctc gag cgg gag tcg acg cca gga     624
His Val Gly Val Phe Gln Ser Tyr Leu Glu Arg Glu Ser Thr Pro Gly
            195                 200                 205 tag                                                                  627
```

<210> SEQ ID NO 64
<211> LENGTH: 208
<212> TYPE: PRT
<213> ORGANISM: Unknown
<220> FEATURE:
<223> OTHER INFORMATION: Metagenome - beta unit nitrile hydratase -
    M12K24

<400> SEQUENCE: 64

```
Met Asp Gly Met His Asp Leu Gly Gly Arg Gln Gly Phe Gly Pro Val
1               5                   10                  15

Arg Tyr Thr Ile Asp Ala Pro Ala Phe His Ser Pro Trp Glu Val Arg
                20                  25                  30

Ala Asn Ser Leu Tyr Ala Phe Ala Val Arg Leu Gly Ile Phe Asn Met
            35                  40                  45

Asp Glu Tyr Arg His Ala Ile Glu Arg Met Glu Pro Arg His Tyr Leu
        50                  55                  60

Gly Ala Gly Tyr Tyr Glu Arg Ser Leu Thr Gly Leu Ala Thr Leu Leu
65                  70                  75                  80
```

```
Val Glu Lys Gly Val Val Thr Arg Glu Leu Glu Thr Arg Ala Gln
            85                  90                  95

Gly Arg Tyr Pro Leu Ala Met Pro Ser Ala Pro Gly Arg Thr Asn Ala
            100                 105                 110

Gln Ala Arg Glu Arg Phe Gln Pro Gly Asp Arg Val Arg Val Lys Ala
            115                 120                 125

Asp Phe Val Ser Gly His Val Arg Met Pro Ala Tyr Ile Arg Gly Lys
130                 135                 140

Thr Gly Val Val Val Ser Glu Ser Pro Asp Tyr Pro Phe Pro Asp Ala
145                 150                 155                 160

His Ala His Ser Val Asp Ala Gln Asp Glu Pro Thr Tyr Asp Val Arg
            165                 170                 175

Phe Arg Ser Glu Asp Leu Trp Pro Asp Ser Ala Asp Ser Ala Leu Val
            180                 185                 190

His Val Gly Val Phe Gln Ser Tyr Leu Glu Arg Glu Ser Thr Pro Gly
            195                 200                 205
```

<210> SEQ ID NO 65
<211> LENGTH: 660
<212> TYPE: DNA
<213> ORGANISM: Unknown
<220> FEATURE:
<223> OTHER INFORMATION: Metagenome - beta unit nitrile hydratase - M29M24
<220> FEATURE:
<221> NAME/KEY: CDS
<222> LOCATION: (1)..(660)

<400> SEQUENCE: 65

```
atg aac ggc gtt cat gac atg ggc ggc atg cac ggc atg ggt gcg atc      48
Met Asn Gly Val His Asp Met Gly Gly Met His Gly Met Gly Ala Ile
1               5                   10                  15 cgc cgc gag gag aac gag ccc gct ttc cac gag ccc tgg gag ggg cgg      96
Arg Arg Glu Glu Asn Glu Pro Ala Phe His Glu Pro Trp Glu Gly Arg
                20                  25                  30 gtt ttc gct ctg acc acg gcg gtc gag gcc tgg ggt cgg tgg acc ctc      144
Val Phe Ala Leu Thr Thr Ala Val Glu Ala Trp Gly Arg Trp Thr Leu
            35                  40                  45 gat gct tcc cga cac cgg atc gag cgg atg aat gcg gcg gac tat ctg      192
Asp Ala Ser Arg His Arg Ile Glu Arg Met Asn Ala Ala Asp Tyr Leu
    50                  55                  60 cgg gtg agc tat tac gag aag tgg ctc gag tcg ctt ctc gct ctc ctg      240
Arg Val Ser Tyr Tyr Glu Lys Trp Leu Glu Ser Leu Leu Ala Leu Leu
65                  70                  75                  80 tcc gag acc gga atg gcg agt ccg gcg gag ata cgg agt ggg gag cgt      288
Ser Glu Thr Gly Met Ala Ser Pro Ala Glu Ile Arg Ser Gly Glu Arg
                85                  90                  95 gcc gac ggc aca ccg aaa gcg acc ccg ccg ctc ccg gcc gac cac gtg      336
Ala Asp Gly Thr Pro Lys Ala Thr Pro Pro Leu Pro Ala Asp His Val
            100                 105                 110 acg gcg att ctc gcc agc ggg ttt ccc gcg agc cgg gag gcg gga gct      384
Thr Ala Ile Leu Ala Ser Gly Phe Pro Ala Ser Arg Glu Ala Gly Ala
    115                 120                 125 gcg cct cgc ttc cga gtg agc gag cgg gtg cgc acc cgg aac atc aac      432
Ala Pro Arg Phe Arg Val Ser Glu Arg Val Arg Thr Arg Asn Ile Asn
130                 135                 140 ccg acg act cac acg cgc ctt ccg cga tac gcc cgg cgg aag ctc ggg      480
Pro Thr Thr His Thr Arg Leu Pro Arg Tyr Ala Arg Arg Lys Leu Gly
145                 150                 155                 160
```

```
acg atc gag cgc gac cac gga gtg ttc gtc ttc ccg gat acg aac gcg      528
Thr Ile Glu Arg Asp His Gly Val Phe Val Phe Pro Asp Thr Asn Ala
            165                 170                 175 cac gct ctc ggg gag aaa ccg cag cac gtc tat tcg gtt cgt ttc gag      576
His Ala Leu Gly Glu Lys Pro Gln His Val Tyr Ser Val Arg Phe Glu
        180                 185                 190 gcg cgt gag ctc tgg ggc gag act gcc agg cca gag gat tcc gtc tac      624
Ala Arg Glu Leu Trp Gly Glu Thr Ala Arg Pro Glu Asp Ser Val Tyr
    195                 200                 205 atc gat ctt tgg gac gag tac ctt gaa ccc gtg tag                      660
Ile Asp Leu Trp Asp Glu Tyr Leu Glu Pro Val
    210                 215
```

<210> SEQ ID NO 66
<211> LENGTH: 219
<212> TYPE: PRT
<213> ORGANISM: Unknown
<220> FEATURE:
<223> OTHER INFORMATION: Metagenome - beta unit nitrile hydratase - M29M24

<400> SEQUENCE: 66

```
Met Asn Gly Val His Asp Met Gly Gly Met His Gly Met Gly Ala Ile
1               5                   10                  15

Arg Arg Glu Glu Asn Glu Pro Ala Phe His Glu Pro Trp Glu Gly Arg
            20                  25                  30

Val Phe Ala Leu Thr Thr Ala Val Glu Ala Trp Gly Arg Trp Thr Leu
        35                  40                  45

Asp Ala Ser Arg His Arg Ile Glu Arg Met Asn Ala Ala Asp Tyr Leu
    50                  55                  60

Arg Val Ser Tyr Tyr Glu Lys Trp Leu Glu Ser Leu Leu Ala Leu Leu
65                  70                  75                  80

Ser Glu Thr Gly Met Ala Ser Pro Ala Glu Ile Arg Ser Gly Glu Arg
                85                  90                  95

Ala Asp Gly Thr Pro Lys Ala Thr Pro Pro Leu Pro Ala Asp His Val
            100                 105                 110

Thr Ala Ile Leu Ala Ser Gly Phe Pro Ala Ser Arg Glu Ala Gly Ala
        115                 120                 125

Ala Pro Arg Phe Arg Val Ser Glu Arg Val Arg Thr Arg Asn Ile Asn
    130                 135                 140

Pro Thr Thr His Thr Arg Leu Pro Arg Tyr Ala Arg Arg Lys Leu Gly
145                 150                 155                 160

Thr Ile Glu Arg Asp His Gly Val Phe Val Phe Pro Asp Thr Asn Ala
                165                 170                 175

His Ala Leu Gly Glu Lys Pro Gln His Val Tyr Ser Val Arg Phe Glu
            180                 185                 190

Ala Arg Glu Leu Trp Gly Glu Thr Ala Arg Pro Glu Asp Ser Val Tyr
        195                 200                 205

Ile Asp Leu Trp Asp Glu Tyr Leu Glu Pro Val
    210                 215
```

<210> SEQ ID NO 67
<211> LENGTH: 660
<212> TYPE: DNA
<213> ORGANISM: Unknown
<220> FEATURE:
<223> OTHER INFORMATION: Metagenome - beta unit nitrile hydratase - M2K17
<220> FEATURE:
<221> NAME/KEY: CDS

<222> LOCATION: (1)..(660)

<400> SEQUENCE: 67

```
atg acc aat tcg ctg cac gac atg ggc ggc atg cac ggc ttt ggc cgg      48
Met Thr Asn Ser Leu His Asp Met Gly Gly Met His Gly Phe Gly Arg
1               5                   10                  15 gtc gag ccc gag ccg aac gag ccg ccg ttt cac cag cgc tgg gag ggc      96
Val Glu Pro Glu Pro Asn Glu Pro Pro Phe His Gln Arg Trp Glu Gly
            20                  25                  30 cgg gtg ctg ggg atg cag cgc gcc atg ggc ttt acc ggg ctg tgg acc     144
Arg Val Leu Gly Met Gln Arg Ala Met Gly Phe Thr Gly Leu Trp Thr
        35                  40                  45 atc gac gcc ggc cgc gcc tcg ctc gaa gcc ctg ccg cca tta gcg tat     192
Ile Asp Ala Gly Arg Ala Ser Leu Glu Ala Leu Pro Pro Leu Ala Tyr
    50                  55                  60 ctg ggt tcg tcc tac tat cgg cgc tgg ttt ctt ggc ctg gag agc cgg     240
Leu Gly Ser Ser Tyr Tyr Arg Arg Trp Phe Leu Gly Leu Glu Ser Arg
65                  70                  75                  80 ctg ctg ctg cgc ggc ctc gtt ggc gag gac gag atc gcg gca ggc cgt     288
Leu Leu Leu Arg Gly Leu Val Gly Glu Asp Glu Ile Ala Ala Gly Arg
                85                  90                  95 tcg atg cgc gcc ggc gcc atg ttg ccg cgc acc ctg acc cag gcc gat     336
Ser Met Arg Ala Gly Ala Met Leu Pro Arg Thr Leu Thr Gln Ala Asp
            100                 105                 110 gtg gag aaa acc ctg acc cgc ggc gac ttc gcc cgc ccg acc aac acc     384
Val Glu Lys Thr Leu Thr Arg Gly Asp Phe Ala Arg Pro Thr Asn Thr
        115                 120                 125 ccg gcg cgt ttc cag ccg ggc gac cgg gtg caa acg aag aac atc aac     432
Pro Ala Arg Phe Gln Pro Gly Asp Arg Val Gln Thr Lys Asn Ile Asn
    130                 135                 140 ccg gcg acc cac acc cgc ctg ccg cgc tat gcc cgc ggc aag act ggc     480
Pro Ala Thr His Thr Arg Leu Pro Arg Tyr Ala Arg Gly Lys Thr Gly
145                 150                 155                 160 acg gtc gag gcg gtc cgc ggc gtt cac gtc ttt ccc gac acc gcc gcg     528
Thr Val Glu Ala Val Arg Gly Val His Val Phe Pro Asp Thr Ala Ala
                165                 170                 175 ctc ggc gcc ggc gac gac ccg caa tgg ctc tac gcc gtg gtc ttc ccg     576
Leu Gly Ala Gly Asp Asp Pro Gln Trp Leu Tyr Ala Val Val Phe Pro
            180                 185                 190 gcg cgc gag ttg tgg gga gag gcg gcc gat ccc gcg atc aaa atc tcg     624
Ala Arg Glu Leu Trp Gly Glu Ala Ala Asp Pro Ala Ile Lys Ile Ser
        195                 200                 205 atc gag gcg ttc gaa ccc tat atc gac ccc gca tga                     660
Ile Glu Ala Phe Glu Pro Tyr Ile Asp Pro Ala
    210                 215
```

<210> SEQ ID NO 68
<211> LENGTH: 219
<212> TYPE: PRT
<213> ORGANISM: Unknown
<220> FEATURE:
<223> OTHER INFORMATION: Metagenome - beta unit nitrile hydratase - M2K17

<400> SEQUENCE: 68

```
Met Thr Asn Ser Leu His Asp Met Gly Gly Met His Gly Phe Gly Arg
1               5                   10                  15

Val Glu Pro Glu Pro Asn Glu Pro Pro Phe His Gln Arg Trp Glu Gly
            20                  25                  30

Arg Val Leu Gly Met Gln Arg Ala Met Gly Phe Thr Gly Leu Trp Thr
        35                  40                  45
```

```
Ile Asp Ala Gly Arg Ala Ser Leu Glu Ala Leu Pro Pro Leu Ala Tyr
    50                  55                  60

Leu Gly Ser Ser Tyr Tyr Arg Arg Trp Phe Leu Gly Leu Glu Ser Arg
65                  70                  75                  80

Leu Leu Leu Arg Gly Leu Val Gly Glu Asp Glu Ile Ala Ala Gly Arg
                85                  90                  95

Ser Met Arg Ala Gly Ala Met Leu Pro Arg Thr Leu Thr Gln Ala Asp
            100                 105                 110

Val Glu Lys Thr Leu Thr Arg Gly Asp Phe Ala Arg Pro Thr Asn Thr
        115                 120                 125

Pro Ala Arg Phe Gln Pro Gly Asp Arg Val Gln Thr Lys Asn Ile Asn
130                 135                 140

Pro Ala Thr His Thr Arg Leu Pro Arg Tyr Ala Arg Gly Lys Thr Gly
145                 150                 155                 160

Thr Val Glu Ala Val Arg Gly Val His Val Phe Pro Asp Thr Ala Ala
                165                 170                 175

Leu Gly Ala Gly Asp Asp Pro Gln Trp Leu Tyr Ala Val Val Phe Pro
            180                 185                 190

Ala Arg Glu Leu Trp Gly Glu Ala Ala Asp Pro Ala Ile Lys Ile Ser
        195                 200                 205

Ile Glu Ala Phe Glu Pro Tyr Ile Asp Pro Ala
    210                 215
```

```
<210> SEQ ID NO 69
<211> LENGTH: 663
<212> TYPE: DNA
<213> ORGANISM: Unknown
<220> FEATURE:
<223> OTHER INFORMATION: Metagenome - beta unit nitrile hydratase -
      M23dA12
<220> FEATURE:
<221> NAME/KEY: CDS
<222> LOCATION: (1)..(663)

<400> SEQUENCE: 69 atg gac ggc gtg cac gac atg ggc ggc atg cac ggt ttc ggc aag gtc      48
Met Asp Gly Val His Asp Met Gly Gly Met His Gly Phe Gly Lys Val
1               5                   10                  15 gag ccg gaa gcg aac gag ccc gcc ttc cat gcg gaa tgg gaa ggc cgc      96
Glu Pro Glu Ala Asn Glu Pro Ala Phe His Ala Glu Trp Glu Gly Arg
            20                  25                  30 tgc ctc gcg ctc aac cgc gcc atg ggt gcg atc ggc gcc tgg acc atc     144
Cys Leu Ala Leu Asn Arg Ala Met Gly Ala Ile Gly Ala Trp Thr Ile
        35                  40                  45 gat gaa ggc cgt gcc ggc atc gag atc ctg ccg ccg gag att tat ctt     192
Asp Glu Gly Arg Ala Gly Ile Glu Ile Leu Pro Pro Glu Ile Tyr Leu
    50                  55                  60 ggc agt tcg tac tat gga aaa tgg gcg cgg cgg ctg gag aat atg gtg     240
Gly Ser Ser Tyr Tyr Gly Lys Trp Ala Arg Arg Leu Glu Asn Met Val
65                  70                  75                  80 gtc gca cgc ggg ttc gcg ggc gcc gat gaa ctc gcc gcg ggt cgc gca     288
Val Ala Arg Gly Phe Ala Gly Ala Asp Glu Leu Ala Ala Gly Arg Ala
                85                  90                  95 gcg cgt ccc ggc aga tcg gtg aaa cga aag ctt acg gtc gcc gaa gtg     336
Ala Arg Pro Gly Arg Ser Val Lys Arg Lys Leu Thr Val Ala Glu Val
            100                 105                 110 ccg cgc acg ctg acg cgc ggt tca ttt ttc cgc gag gca aca aag ccg     384
Pro Arg Thr Leu Thr Arg Gly Ser Phe Phe Arg Glu Ala Thr Lys Pro
        115                 120                 125
```

```
gca cga ttt gcg gtc ggc gaa cgc gtg cgc acc agg aac att cat ccg    432
Ala Arg Phe Ala Val Gly Glu Arg Val Arg Thr Arg Asn Ile His Pro
    130                 135                 140 gcg acg cac act cgg ttg ccg cga tat gcg cgc ggc cat gtc ggc gtg    480
Ala Thr His Thr Arg Leu Pro Arg Tyr Ala Arg Gly His Val Gly Val
145                 150                 155                 160 atc gag gcg atc cgc ggt tgc cac gta ttt ccc gac tcg gtt gcg atc    528
Ile Glu Ala Ile Arg Gly Cys His Val Phe Pro Asp Ser Val Ala Ile
                165                 170                 175 ggc gcc ggc gag aac ccg caa tgg ctt tat acg gtg gtg ttc gaa ggc    576
Gly Ala Gly Glu Asn Pro Gln Trp Leu Tyr Thr Val Val Phe Glu Gly
            180                 185                 190 cgc acg ctg tgg ggc gat agc gcc gat ccg acg ctt aag gtc tcg atc    624
Arg Thr Leu Trp Gly Asp Ser Ala Asp Pro Thr Leu Lys Val Ser Ile
        195                 200                 205 gag gcg ttc gag ccg tat ctg gaa ccg gcc caa cca tga                663
Glu Ala Phe Glu Pro Tyr Leu Glu Pro Ala Gln Pro
    210                 215                 220

<210> SEQ ID NO 70
<211> LENGTH: 220
<212> TYPE: PRT
<213> ORGANISM: Unknown
<220> FEATURE:
<223> OTHER INFORMATION: Metagenome - beta unit nitrile hydratase -
      M23dA12

<400> SEQUENCE: 70

Met Asp Gly Val His Asp Met Gly Gly Met His Gly Phe Gly Lys Val
1               5                   10                  15

Glu Pro Glu Ala Asn Glu Pro Ala Phe His Ala Glu Trp Glu Gly Arg
            20                  25                  30

Cys Leu Ala Leu Asn Arg Ala Met Gly Ala Ile Gly Ala Trp Thr Ile
        35                  40                  45

Asp Glu Gly Arg Ala Gly Ile Glu Ile Leu Pro Pro Glu Ile Tyr Leu
    50                  55                  60

Gly Ser Ser Tyr Tyr Gly Lys Trp Ala Arg Arg Leu Glu Asn Met Val
65                  70                  75                  80

Val Ala Arg Gly Phe Ala Gly Ala Asp Glu Leu Ala Ala Gly Arg Ala
                85                  90                  95

Ala Arg Pro Gly Arg Ser Val Lys Arg Lys Leu Thr Val Ala Glu Val
            100                 105                 110

Pro Arg Thr Leu Thr Arg Gly Ser Phe Phe Arg Glu Ala Thr Lys Pro
        115                 120                 125

Ala Arg Phe Ala Val Gly Glu Arg Val Arg Thr Arg Asn Ile His Pro
    130                 135                 140

Ala Thr His Thr Arg Leu Pro Arg Tyr Ala Arg Gly His Val Gly Val
145                 150                 155                 160

Ile Glu Ala Ile Arg Gly Cys His Val Phe Pro Asp Ser Val Ala Ile
                165                 170                 175

Gly Ala Gly Glu Asn Pro Gln Trp Leu Tyr Thr Val Val Phe Glu Gly
            180                 185                 190

Arg Thr Leu Trp Gly Asp Ser Ala Asp Pro Thr Leu Lys Val Ser Ile
        195                 200                 205

Glu Ala Phe Glu Pro Tyr Leu Glu Pro Ala Gln Pro
    210                 215                 220
```

<210> SEQ ID NO 71
<211> LENGTH: 888
<212> TYPE: DNA
<213> ORGANISM: Unknown
<220> FEATURE:
<223> OTHER INFORMATION: Metagenome - beta unit nitrile hydratase - M49bD9
<220> FEATURE:
<221> NAME/KEY: CDS
<222> LOCATION: (1)..(888)

<400> SEQUENCE: 71

| | | | | | | | | | | | | | | | | |
|---|---|---|---|---|---|---|---|---|---|---|---|---|---|---|---|---|
| atg | aac | ggc | gta | cac | gat | ctt | ggc | ggg | atg | gat | ggt | ttc | ggc | cgg | gtg | 48 |
| Met | Asn | Gly | Val | His | Asp | Leu | Gly | Gly | Met | Asp | Gly | Phe | Gly | Arg | Val | |
| 1 | | | | 5 | | | | | 10 | | | | | 15 | | |
| atg | gcg | gag | gcg | gac | gag | ccg | gtc | ttt | cat | gag | ccc | tgg | gaa | ggt | cgc | 96 |
| Met | Ala | Glu | Ala | Asp | Glu | Pro | Val | Phe | His | Glu | Pro | Trp | Glu | Gly | Arg | |
| | | | 20 | | | | | 25 | | | | | 30 | | | |
| gtg | ttt | gcg | ctc | aac | atg | ctc | ggc | atc | ggg | cgc | gag | ccc | att | ccg | gtg | 144 |
| Val | Phe | Ala | Leu | Asn | Met | Leu | Gly | Ile | Gly | Arg | Glu | Pro | Ile | Pro | Val | |
| | | 35 | | | | | 40 | | | | | 45 | | | | |
| gac | gcg | ctg | cgc | cat | cgc | att | gag | cgg | atc | gag | ccg | tgg | cgc | tat | ctg | 192 |
| Asp | Ala | Leu | Arg | His | Arg | Ile | Glu | Arg | Ile | Glu | Pro | Trp | Arg | Tyr | Leu | |
| | 50 | | | | | 55 | | | | | 60 | | | | | |
| acg | tcg | agc | tat | tac | gaa | cga | tgg | ctg | gcc | gaa | atg | gag | cag | gcc | atc | 240 |
| Thr | Ser | Ser | Tyr | Tyr | Glu | Arg | Trp | Leu | Ala | Glu | Met | Glu | Gln | Ala | Ile | |
| 65 | | | | | 70 | | | | | 75 | | | | | 80 | |
| atc | gat | gcg | ggc | acg | ctg | act | cct | ggt | gaa | atc | gat | gcg | cga | atg | ggc | 288 |
| Ile | Asp | Ala | Gly | Thr | Leu | Thr | Pro | Gly | Glu | Ile | Asp | Ala | Arg | Met | Gly | |
| | | | | 85 | | | | | 90 | | | | | 95 | | |
| gag | ctc | gaa | acg | gat | cct | gat | cgc | cca | ctg | cca | agg | act | gat | aac | cct | 336 |
| Glu | Leu | Glu | Thr | Asp | Pro | Asp | Arg | Pro | Leu | Pro | Arg | Thr | Asp | Asn | Pro | |
| | | | 100 | | | | | 105 | | | | | 110 | | | |
| gag | cat | gcc | gat | ggg | gtg | gcg | gcg | gcg | ttg | cgc | gcc | ggc | agt | ccc | gta | 384 |
| Glu | His | Ala | Asp | Gly | Val | Ala | Ala | Ala | Leu | Arg | Ala | Gly | Ser | Pro | Val | |
| | | 115 | | | | | 120 | | | | | 125 | | | | |
| acg | cgc | aag | att | cgc | aag | cag | ccg | cgc | ttc | aca | atc | ggc | gat | cgg | gtc | 432 |
| Thr | Arg | Lys | Ile | Arg | Lys | Gln | Pro | Arg | Phe | Thr | Ile | Gly | Asp | Arg | Val | |
| | 130 | | | | | 135 | | | | | 140 | | | | | |
| gta | acg | cgc | aat | ctt | aat | ccg | cac | ggc | cat | acg | cgg | ctg | ccg | cgc | tat | 480 |
| Val | Thr | Arg | Asn | Leu | Asn | Pro | His | Gly | His | Thr | Arg | Leu | Pro | Arg | Tyr | |
| 145 | | | | | 150 | | | | | 155 | | | | | 160 | |
| gcg | cgc | ggc | aag | cgc | ggc | gtc | gta | acg | ctg | cac | cat | ggc | gca | cat | gtc | 528 |
| Ala | Arg | Gly | Lys | Arg | Gly | Val | Val | Thr | Leu | His | His | Gly | Ala | His | Val | |
| | | | | 165 | | | | | 170 | | | | | 175 | | |
| ttt | ccg | gat | acg | aac | gcg | cac | ggg | ctg | ggc | gag | cat | ccg | cag | cat | ctc | 576 |
| Phe | Pro | Asp | Thr | Asn | Ala | His | Gly | Leu | Gly | Glu | His | Pro | Gln | His | Leu | |
| | | | 180 | | | | | 185 | | | | | 190 | | | |
| tat | acg | gtg | cga | ttt | cct | gcg | cgc | gag | tta | tgg | agc | gac | gcg | gcc | gag | 624 |
| Tyr | Thr | Val | Arg | Phe | Pro | Ala | Arg | Glu | Leu | Trp | Ser | Asp | Ala | Ala | Glu | |
| | | 195 | | | | | 200 | | | | | 205 | | | | |
| ccg | aaa | gaa | tcg | ata | atg | atc | gat | ttg | tgg | gag | agc | tat | ctt | caa | ccc | 672 |
| Pro | Lys | Glu | Ser | Ile | Met | Ile | Asp | Leu | Trp | Glu | Ser | Tyr | Leu | Gln | Pro | |
| | 210 | | | | | 215 | | | | | 220 | | | | | |
| gat | atc | ggc | agc | aaa | gcg | tcg | tcg | tcc | gcg | aaa | ggc | aaa | gcg | acg | ccg | 720 |
| Asp | Ile | Gly | Ser | Lys | Ala | Ser | Ser | Ser | Ala | Lys | Gly | Lys | Ala | Thr | Pro | |
| 225 | | | | | 230 | | | | | 235 | | | | | 240 | |
| aaa | gtt | aag | ccc | gca | atg | gcc | aag | gca | acc | gcc | aag | gta | agc | gtc | tcg | 768 |
| Lys | Val | Lys | Pro | Ala | Met | Ala | Lys | Ala | Thr | Ala | Lys | Val | Ser | Val | Ser | |
| | | | | 245 | | | | | 250 | | | | | 255 | | |
| gcc | aag | gcc | aaa | act | cgg | gga | aag | gcg | gcg | ccg | aag | gag | cgt | cca | aaa | 816 |
| Ala | Lys | Ala | Lys | Thr | Arg | Gly | Lys | Ala | Ala | Pro | Lys | Glu | Arg | Pro | Lys | |

```
                260                 265                 270
ctg aaa cct gcg cga gcg gcg acc tca gca gca tcc ggc ggc gaa aaa          864
Leu Lys Pro Ala Arg Ala Ala Thr Ser Ala Ala Ser Gly Gly Glu Lys
        275                 280                 285 gct aag cga aag gcc aaa cga tga                                          888
Ala Lys Arg Lys Ala Lys Arg
    290                 295

<210> SEQ ID NO 72
<211> LENGTH: 295
<212> TYPE: PRT
<213> ORGANISM: Unknown
<220> FEATURE:
<223> OTHER INFORMATION: Metagenome - beta unit nitrile hydratase -
      M49bD9

<400> SEQUENCE: 72

Met Asn Gly Val His Asp Leu Gly Gly Met Asp Gly Phe Gly Arg Val
1               5                   10                  15

Met Ala Glu Ala Asp Glu Pro Val Phe His Glu Pro Trp Glu Gly Arg
            20                  25                  30

Val Phe Ala Leu Asn Met Leu Gly Ile Gly Arg Glu Pro Ile Pro Val
        35                  40                  45

Asp Ala Leu Arg His Arg Ile Glu Arg Ile Glu Pro Trp Arg Tyr Leu
    50                  55                  60

Thr Ser Ser Tyr Tyr Glu Arg Trp Leu Ala Glu Met Glu Gln Ala Ile
65                  70                  75                  80

Ile Asp Ala Gly Thr Leu Thr Pro Gly Glu Ile Asp Ala Arg Met Gly
                85                  90                  95

Glu Leu Glu Thr Asp Pro Asp Arg Pro Leu Pro Arg Thr Asp Asn Pro
            100                 105                 110

Glu His Ala Asp Gly Val Ala Ala Leu Arg Ala Gly Ser Pro Val
        115                 120                 125

Thr Arg Lys Ile Arg Lys Gln Pro Arg Phe Thr Ile Gly Asp Arg Val
    130                 135                 140

Val Thr Arg Asn Leu Asn Pro His Gly His Thr Arg Leu Pro Arg Tyr
145                 150                 155                 160

Ala Arg Gly Lys Arg Gly Val Val Thr Leu His His Gly Ala His Val
                165                 170                 175

Phe Pro Asp Thr Asn Ala His Gly Leu Gly Glu His Pro Gln His Leu
            180                 185                 190

Tyr Thr Val Arg Phe Pro Ala Arg Glu Leu Trp Ser Asp Ala Ala Glu
        195                 200                 205

Pro Lys Glu Ser Ile Met Ile Asp Leu Trp Gln Ser Tyr Leu Gln Pro
    210                 215                 220

Asp Ile Gly Ser Lys Ala Ser Ser Ala Lys Gly Lys Ala Thr Pro
225                 230                 235                 240

Lys Val Lys Pro Ala Met Ala Lys Ala Thr Ala Lys Val Ser Val Ser
                245                 250                 255

Ala Lys Ala Lys Thr Arg Gly Lys Ala Ala Pro Lys Glu Arg Pro Lys
            260                 265                 270

Leu Lys Pro Ala Arg Ala Ala Thr Ser Ala Ala Ser Gly Gly Glu Lys
        275                 280                 285

Ala Lys Arg Lys Ala Lys Arg
    290                 295
```

<210> SEQ ID NO 73
<211> LENGTH: 630
<212> TYPE: DNA
<213> ORGANISM: Unknown
<220> FEATURE:
<223> OTHER INFORMATION: Metagenome - beta unit nitrile hydratase - M6dE2
<220> FEATURE:
<221> NAME/KEY: CDS
<222> LOCATION: (1)..(630)

<400> SEQUENCE: 73

| | | | | | | | | | | | | | | | | |
|---|---|---|---|---|---|---|---|---|---|---|---|---|---|---|---|---|
| atg | gac | ggc | att | cat | gat | ctc | ggt | ggg | atg | agc | ggg | ttc | ggt | ctc | gtg | 48 |
| Met | Asp | Gly | Ile | His | Asp | Leu | Gly | Gly | Met | Ser | Gly | Phe | Gly | Leu | Val | |
| 1 | | | | 5 | | | | | 10 | | | | | 15 | | |
| gag | atc | gag | ccc | gat | gag | ccg | gtg | ttc | cac | gag | ccc | tgg | gag | gcg | ctg | 96 |
| Glu | Ile | Glu | Pro | Asp | Glu | Pro | Val | Phe | His | Glu | Pro | Trp | Glu | Ala | Leu | |
| | | 20 | | | | | 25 | | | | | 30 | | | | |
| gtt | ttc | gct | ctg | atg | act | ctc | ggt | atc | ggg | aag | ctc | ggc | gcg | tac | aac | 144 |
| Val | Phe | Ala | Leu | Met | Thr | Leu | Gly | Ile | Gly | Lys | Leu | Gly | Ala | Tyr | Asn | |
| | 35 | | | | | 40 | | | | | 45 | | | | | |
| gcc | gat | gag | tac | cgc | cac | tcg | atc | gag | cgg | atg | gat | ccg | gcc | cac | tac | 192 |
| Ala | Asp | Glu | Tyr | Arg | His | Ser | Ile | Glu | Arg | Met | Asp | Pro | Ala | His | Tyr | |
| 50 | | | | | 55 | | | | | 60 | | | | | | |
| ctt | gcg | gcg | acg | tac | tac | gag | cgc | atg | ctc | acc | ggc | gtc | gca | acg | ctc | 240 |
| Leu | Ala | Ala | Thr | Tyr | Tyr | Glu | Arg | Met | Leu | Thr | Gly | Val | Ala | Thr | Leu | |
| 65 | | | | | 70 | | | | | 75 | | | | | 80 | |
| ctc | gtc | gag | aag | aac | gtc | gtt | gcc | cgc | gac | gag | ctc | gaa | gcg | cgc | gcc | 288 |
| Leu | Val | Glu | Lys | Asn | Val | Val | Ala | Arg | Asp | Glu | Leu | Glu | Ala | Arg | Ala | |
| | | | | 85 | | | | | 90 | | | | | 95 | | |
| ggc | ggg | ccc | ttc | ccg | ctg | tca | cgg | ccg | gtg | gcc | gag | cgg | ccg | acg | gcg | 336 |
| Gly | Gly | Pro | Phe | Pro | Leu | Ser | Arg | Pro | Val | Ala | Glu | Arg | Pro | Thr | Ala | |
| | | 100 | | | | | 105 | | | | | 110 | | | | |
| gac | ctt | cgg | ccc | cag | cca | caa | cca | cgc | ttc | gcg | gtc | ggg | gat | cgg | gtc | 384 |
| Asp | Leu | Arg | Pro | Gln | Pro | Gln | Pro | Arg | Phe | Ala | Val | Gly | Asp | Arg | Val | |
| | 115 | | | | | 120 | | | | | 125 | | | | | |
| gtc | gtg | cgc | gac | atc | cac | ccg | gcc | ggg | cat | act | cgt | gtg | ccg | cgc | tac | 432 |
| Val | Val | Arg | Asp | Ile | His | Pro | Ala | Gly | His | Thr | Arg | Val | Pro | Arg | Tyr | |
| 130 | | | | | 135 | | | | | 140 | | | | | | |
| gtg | cgg | ggc | aag | cgc | ggg | acc | gtc | gtg | cac | gtc | gcg | ccg | aaa | ttc | tcg | 480 |
| Val | Arg | Gly | Lys | Arg | Gly | Thr | Val | Val | His | Val | Ala | Pro | Lys | Phe | Ser | |
| 145 | | | | | 150 | | | | | 155 | | | | | 160 | |
| ttc | ccc | gac | acg | gcc | gcg | cac | ggg | ctg | acc | cat | cgg | agc | gag | cac | acg | 528 |
| Phe | Pro | Asp | Thr | Ala | Ala | His | Gly | Leu | Thr | His | Arg | Ser | Glu | His | Thr | |
| | | | | 165 | | | | | 170 | | | | | 175 | | |
| tat | cac | gtg | gaa | ttc | gtc | gcg | agt | gac | ctt | tgg | gcc | gac | gtg | gcc | ggg | 576 |
| Tyr | His | Val | Glu | Phe | Val | Ala | Ser | Asp | Leu | Trp | Ala | Asp | Val | Ala | Gly | |
| | | 180 | | | | | 185 | | | | | 190 | | | | |
| agc | aat | gag | agc | gta | ctc | gtg | gac | ctg | tgg | gac | ggc | tat | ctg | gag | ggc | 624 |
| Ser | Asn | Glu | Ser | Val | Leu | Val | Asp | Leu | Trp | Asp | Gly | Tyr | Leu | Glu | Gly | |
| | 195 | | | | | 200 | | | | | 205 | | | | | |
| gca | tga | | | | | | | | | | | | | | | 630 |
| Ala | | | | | | | | | | | | | | | | |

<210> SEQ ID NO 74
<211> LENGTH: 209
<212> TYPE: PRT
<213> ORGANISM: Unknown
<220> FEATURE:
<223> OTHER INFORMATION: Metagenome - beta unit nitrile hydratase - M6dE2

<400> SEQUENCE: 74

-continued

```
Met Asp Gly Ile His Asp Leu Gly Gly Met Ser Gly Phe Gly Leu Val
1               5                   10                  15

Glu Ile Glu Pro Asp Glu Pro Val Phe His Glu Pro Trp Glu Ala Leu
            20                  25                  30

Val Phe Ala Leu Met Thr Leu Gly Ile Gly Lys Leu Gly Ala Tyr Asn
        35                  40                  45

Ala Asp Glu Tyr Arg His Ser Ile Glu Arg Met Asp Pro Ala His Tyr
    50                  55                  60

Leu Ala Ala Thr Tyr Tyr Glu Arg Met Leu Thr Gly Val Ala Thr Leu
65                  70                  75                  80

Leu Val Glu Lys Asn Val Val Ala Arg Asp Glu Leu Glu Ala Arg Ala
                85                  90                  95

Gly Gly Pro Phe Pro Leu Ser Arg Pro Val Ala Glu Arg Pro Thr Ala
            100                 105                 110

Asp Leu Arg Pro Gln Pro Gln Pro Arg Phe Ala Val Gly Asp Arg Val
        115                 120                 125

Val Val Arg Asp Ile His Pro Ala Gly His Thr Arg Val Pro Arg Tyr
    130                 135                 140

Val Arg Gly Lys Arg Gly Thr Val Val His Val Ala Pro Lys Phe Ser
145                 150                 155                 160

Phe Pro Asp Thr Ala Ala His Gly Leu Thr His Arg Ser Glu His Thr
                165                 170                 175

Tyr His Val Glu Phe Val Ala Ser Asp Leu Trp Ala Asp Val Ala Gly
            180                 185                 190

Ser Asn Glu Ser Val Leu Val Asp Leu Trp Asp Gly Tyr Leu Glu Gly
        195                 200                 205

Ala
```

<210> SEQ ID NO 75
<211> LENGTH: 651
<212> TYPE: DNA
<213> ORGANISM: Unknown
<220> FEATURE:
<223> OTHER INFORMATION: Metagenome - beta unit nitrile hydratase - M25A18
<220> FEATURE:
<221> NAME/KEY: CDS
<222> LOCATION: (1)..(651)

<400> SEQUENCE: 75

```
atg cgc ggc acg cac gat ctc ggc gga ttg ccc gcc ggc ccg gtg gac      48
Met Arg Gly Thr His Asp Leu Gly Gly Leu Pro Ala Gly Pro Val Asp
1               5                   10                  15 acc gct ccc cac gaa ccg acc ttc tgg gaa aag cag gtg gac gcg atc      96
Thr Ala Pro His Glu Pro Thr Phe Trp Glu Lys Gln Val Asp Ala Ile
            20                  25                  30 cac ggc ctg ctc ggc gat tcc aag cgc cgc atc acg ctg cgc gac gag     144
His Gly Leu Leu Gly Asp Ser Lys Arg Arg Ile Thr Leu Arg Asp Glu
        35                  40                  45 aac cgc ctc tat atc gaa tcg ctc ggc gac gac gtc tac aac acg ctc     192
Asn Arg Leu Tyr Ile Glu Ser Leu Gly Asp Asp Val Tyr Asn Thr Leu
    50                  55                  60 ggc tat tac gag cgc tgg acc gcc gcc atg tgc cgc cag ctc atc gac     240
Gly Tyr Tyr Glu Arg Trp Thr Ala Ala Met Cys Arg Gln Leu Ile Asp
65                  70                  75                  80 aag ggc gtg ctg acg cag gac gag atc gac gcc aag atc gcc gag ctg     288
Lys Gly Val Leu Thr Gln Asp Glu Ile Asp Ala Lys Ile Ala Glu Leu
                85                  90                  95
```

```
cgc gcc cgc ggc gtc ggc gcg gga cga cga cga aac ggc ctg caa acc    336
Arg Ala Arg Gly Val Gly Ala Gly Arg Arg Arg Asn Gly Leu Gln Thr
        100                 105                 110 gtg agc gcc gat ctg gcc gcc gat ctg gcc atc gcg ccg cgc ttc gcc    384
Val Ser Ala Asp Leu Ala Ala Asp Leu Ala Ile Ala Pro Arg Phe Ala
        115                 120                 125 gcc ggc gac cgc gtg cgg gtg cgc gac gat tat ccg ccc ggg cac atc    432
Ala Gly Asp Arg Val Arg Val Arg Asp Asp Tyr Pro Pro Gly His Ile
130                 135                 140 cgc acg ccg gtc tat gtg cgc ggc aag acg ggc gtg gtg acg cgc tgc    480
Arg Thr Pro Val Tyr Val Arg Gly Lys Thr Gly Val Val Thr Arg Cys
145                 150                 155                 160 ttc ggc gcg ttc aag aac ccg gaa ttg ctc gcc atc ggc aag gac ggc    528
Phe Gly Ala Phe Lys Asn Pro Glu Leu Leu Ala Ile Gly Lys Asp Gly
                165                 170                 175 ctg ccc aag aaa att ctc tac gaa gtg cgc ttc aag cag acc gat ctc    576
Leu Pro Lys Lys Ile Leu Tyr Glu Val Arg Phe Lys Gln Thr Asp Leu
            180                 185                 190 tgg ccc gac tat gcc ggg ccg gcg acc gat acg ctg ctg atc gac atc    624
Trp Pro Asp Tyr Ala Gly Pro Ala Thr Asp Thr Leu Leu Ile Asp Ile
        195                 200                 205 tac gaa cat tgg ctg agc gac gcg tga                                651
Tyr Glu His Trp Leu Ser Asp Ala
    210                 215

<210> SEQ ID NO 76
<211> LENGTH: 216
<212> TYPE: PRT
<213> ORGANISM: Unknown
<220> FEATURE:
<223> OTHER INFORMATION: Metagenome - beta unit nitrile hydratase -
      M25A18

<400> SEQUENCE: 76

Met Arg Gly Thr His Asp Leu Gly Gly Leu Pro Ala Gly Pro Val Asp
1               5                   10                  15

Thr Ala Pro His Glu Pro Thr Phe Trp Glu Lys Gln Val Asp Ala Ile
            20                  25                  30

His Gly Leu Leu Gly Asp Ser Lys Arg Ile Thr Leu Arg Asp Glu
        35                  40                  45

Asn Arg Leu Tyr Ile Glu Ser Leu Gly Asp Val Tyr Asn Thr Leu
    50                  55                  60

Gly Tyr Tyr Glu Arg Trp Thr Ala Ala Met Cys Arg Gln Leu Ile Asp
65                  70                  75                  80

Lys Gly Val Leu Thr Gln Asp Glu Ile Asp Ala Lys Ile Ala Glu Leu
                85                  90                  95

Arg Ala Arg Gly Val Gly Ala Gly Arg Arg Arg Asn Gly Leu Gln Thr
            100                 105                 110

Val Ser Ala Asp Leu Ala Ala Asp Leu Ala Ile Ala Pro Arg Phe Ala
        115                 120                 125

Ala Gly Asp Arg Val Arg Val Arg Asp Asp Tyr Pro Pro Gly His Ile
    130                 135                 140

Arg Thr Pro Val Tyr Val Arg Gly Lys Thr Gly Val Val Thr Arg Cys
145                 150                 155                 160

Phe Gly Ala Phe Lys Asn Pro Glu Leu Leu Ala Ile Gly Lys Asp Gly
                165                 170                 175

Leu Pro Lys Lys Ile Leu Tyr Glu Val Arg Phe Lys Gln Thr Asp Leu
            180                 185                 190
```

```
Trp Pro Asp Tyr Ala Gly Pro Ala Thr Asp Thr Leu Leu Ile Asp Ile
        195                 200                 205

Tyr Glu His Trp Leu Ser Asp Ala
    210                 215

<210> SEQ ID NO 77
<211> LENGTH: 657
<212> TYPE: DNA
<213> ORGANISM: Unknown
<220> FEATURE:
<223> OTHER INFORMATION: Metagenome - beta unit nitrile hydratase -
      M50bD9
<220> FEATURE:
<221> NAME/KEY: CDS
<222> LOCATION: (1)..(657)

<400> SEQUENCE: 77 atg aac ggc atg cat gac atg ggc ggc atg cac ggc atg gga ccc att      48
Met Asn Gly Met His Asp Met Gly Gly Met His Gly Met Gly Pro Ile
1               5                  10                  15 cag atc gag aag gac gag tcg ccc ttc cat gcg cgc tgg gaa ggc cgg      96
Gln Ile Glu Lys Asp Glu Ser Pro Phe His Ala Arg Trp Glu Gly Arg
                20                  25                  30 gcg caa gcg atg tac aac gcc att gcg gcc acg ggc aga ctg gtg ctt     144
Ala Gln Ala Met Tyr Asn Ala Ile Ala Ala Thr Gly Arg Leu Val Leu
            35                  40                  45 ggc ggt aga ccc aca cgg gaa ggg ttc ccg ccg gcc gaa tat ctc cgc     192
Gly Gly Arg Pro Thr Arg Glu Gly Phe Pro Pro Ala Glu Tyr Leu Arg
        50                  55                  60 atg agc tac tat gaa ttg ggt ttc agg gtg ctg gtc gag gac ttg gtc     240
Met Ser Tyr Tyr Glu Leu Gly Phe Arg Val Leu Val Glu Asp Leu Val
65                  70                  75                  80 ctg aac ggt ttg gtg acg cgc gcg gaa atc acg agc ggc cgt ccg gca     288
Leu Asn Gly Leu Val Thr Arg Ala Glu Ile Thr Ser Gly Arg Pro Ala
                85                  90                  95 aag ggg gct gca aag tcg acg ccc gca atc acc gcc gcc acc gcg cag     336
Lys Gly Ala Ala Lys Ser Thr Pro Ala Ile Thr Ala Ala Thr Ala Gln
            100                 105                 110 gca tat atg ttc gcg ctc aaa tcg acc cgg cga gac gta ccg gtc acg     384
Ala Tyr Met Phe Ala Leu Lys Ser Thr Arg Arg Asp Val Pro Val Thr
        115                 120                 125 gcg cgt ttc caa gtc ggt cag cgt gtg cgc gcg cgc aac atc aat ccg     432
Ala Arg Phe Gln Val Gly Gln Arg Val Arg Ala Arg Asn Ile Asn Pro
    130                 135                 140 gtc acc cat acg cgc ctg ccc cgt tac gcg cgc ggc aaa ttc ggc gtt     480
Val Thr His Thr Arg Leu Pro Arg Tyr Ala Arg Gly Lys Phe Gly Val
145                 150                 155                 160 atc gaa cgt gac cac ggt gtt tac agg ttc gac gat tcc ttt gcc acg     528
Ile Glu Arg Asp His Gly Val Tyr Arg Phe Asp Asp Ser Phe Ala Thr
                165                 170                 175 tcc ggc gac gag aag ccc cag cac gtt tat tct gtg cgc ttc gcg gcg     576
Ser Gly Asp Glu Lys Pro Gln His Val Tyr Ser Val Arg Phe Ala Ala
            180                 185                 190 cgc gaa cta tgg ggc gaa gcc gcg ccg ccg cga gat gct gtc tat atc     624
Arg Glu Leu Trp Gly Glu Ala Ala Pro Pro Arg Asp Ala Val Tyr Ile
        195                 200                 205 gaa atc tgg gat gac aac ctt gag cca gcg tga                         657
Glu Ile Trp Asp Asp Asn Leu Glu Pro Ala
        210                 215

<210> SEQ ID NO 78
<211> LENGTH: 218
```

```
<212> TYPE: PRT
<213> ORGANISM: Unknown
<220> FEATURE:
<223> OTHER INFORMATION: Metagenome - beta unit nitrile hydratase -
      M50bD9

<400> SEQUENCE: 78

Met Asn Gly Met His Asp Met Gly Gly Met His Gly Met Gly Pro Ile
1               5                   10                  15

Gln Ile Glu Lys Asp Glu Ser Pro Phe His Ala Arg Trp Glu Gly Arg
            20                  25                  30

Ala Gln Ala Met Tyr Asn Ala Ile Ala Ala Thr Gly Arg Leu Val Leu
        35                  40                  45

Gly Gly Arg Pro Thr Arg Glu Gly Phe Pro Pro Ala Glu Tyr Leu Arg
    50                  55                  60

Met Ser Tyr Tyr Glu Leu Gly Phe Arg Val Leu Val Glu Asp Leu Val
65                  70                  75                  80

Leu Asn Gly Leu Val Thr Arg Ala Glu Ile Thr Ser Gly Arg Pro Ala
                85                  90                  95

Lys Gly Ala Ala Lys Ser Thr Pro Ala Ile Thr Ala Ala Thr Ala Gln
            100                 105                 110

Ala Tyr Met Phe Ala Leu Lys Ser Thr Arg Arg Asp Val Pro Val Thr
        115                 120                 125

Ala Arg Phe Gln Val Gly Gln Arg Val Arg Ala Arg Asn Ile Asn Pro
    130                 135                 140

Val Thr His Thr Arg Leu Pro Arg Tyr Ala Arg Gly Lys Phe Gly Val
145                 150                 155                 160

Ile Glu Arg Asp His Gly Val Tyr Arg Phe Asp Asp Ser Phe Ala Thr
                165                 170                 175

Ser Gly Asp Glu Lys Pro Gln His Val Tyr Ser Val Arg Phe Ala Ala
            180                 185                 190

Arg Glu Leu Trp Gly Glu Ala Ala Pro Pro Arg Asp Ala Val Tyr Ile
        195                 200                 205

Glu Ile Trp Asp Asp Asn Leu Glu Pro Ala
    210                 215

<210> SEQ ID NO 79
<211> LENGTH: 696
<212> TYPE: DNA
<213> ORGANISM: Unknown
<220> FEATURE:
<223> OTHER INFORMATION: Metagenome - beta unit nitrile hydratase -
      M3aG10
<220> FEATURE:
<221> NAME/KEY: CDS
<222> LOCATION: (1)..(696)

<400> SEQUENCE: 79 atg gat cca acg agg cgt agt ttc ctg gcg tct acc gtt gcc ctg acc     48
Met Asp Pro Thr Arg Arg Ser Phe Leu Ala Ser Thr Val Ala Leu Thr
1               5                   10                  15 ggc ggc gca gct atc ccc gat ctg gct cat gcg gca gac cac gac cac     96
Gly Gly Ala Ala Ile Pro Asp Leu Ala His Ala Ala Asp His Asp His
            20                  25                  30 cag cat caa gat ttg ccg tcc gat ctg gcg ctg cgg gtg aag tcg ctc    144
Gln His Gln Asp Leu Pro Ser Asp Leu Ala Leu Arg Val Lys Ser Leu
        35                  40                  45 gaa tcg ctg ctt gtc gag aag ggg ctg gtg gag cga gca gcg ctc gac    192
Glu Ser Leu Leu Val Glu Lys Gly Leu Val Glu Arg Ala Ala Leu Asp
    50                  55                  60
```

```
gcg ctg gtg gac acc tac gag cac aaa gtc ggg ccg cga aac gga gcg      240
Ala Leu Val Asp Thr Tyr Glu His Lys Val Gly Pro Arg Asn Gly Ala
 65                  70                  75                  80 cgc gtt gtc gcg cgg gcc tgg gtt gac ccg gac tac aag caa cgg tta      288
Arg Val Val Ala Arg Ala Trp Val Asp Pro Asp Tyr Lys Gln Arg Leu
                 85                  90                  95 ttc gcg aac ggt acc gcc gca gtc gcg gag ttc ggc tac tcc ggc tcg      336
Phe Ala Asn Gly Thr Ala Ala Val Ala Glu Phe Gly Tyr Ser Gly Ser
            100                 105                 110 cag ggc gct gac atc cgg gtc gtc gaa aac acg gcc act gta cat aac      384
Gln Gly Ala Asp Ile Arg Val Val Glu Asn Thr Ala Thr Val His Asn
        115                 120                 125 ctc gtc gtg tgc acg ctg tgc tct tgt tat ccc tgg ccg gtg ctg ggc      432
Leu Val Val Cys Thr Leu Cys Ser Cys Tyr Pro Trp Pro Val Leu Gly
    130                 135                 140 ttg ccg ccg gtc tgg tac aag tcc gcg ccc tat cgg tct cgc gtg gtg      480
Leu Pro Pro Val Trp Tyr Lys Ser Ala Pro Tyr Arg Ser Arg Val Val
145                 150                 155                 160 atc gat ccg cga ggt gtg ctg cgc gag ttc ggc gtg gtg ctg ccg gac      528
Ile Asp Pro Arg Gly Val Leu Arg Glu Phe Gly Val Val Leu Pro Asp
                165                 170                 175 cat atc gaa gtg cgt gtc tat gac agc acg gcg gag caa cgc tat cta      576
His Ile Glu Val Arg Val Tyr Asp Ser Thr Ala Glu Gln Arg Tyr Leu
            180                 185                 190 gtg ctg ccg gag cgg ccg gcc gga acc gaa aac ctg aca gaa gaa gcg      624
Val Leu Pro Glu Arg Pro Ala Gly Thr Glu Asn Leu Thr Glu Glu Ala
        195                 200                 205 ctg gcg ctg ctg gtg acg cgc gac gcg atg att ggc gtg gcc aag gtc      672
Leu Ala Leu Leu Val Thr Arg Asp Ala Met Ile Gly Val Ala Lys Val
    210                 215                 220 gcg ccg ccg gga ggc cgc gga tga                                      696
Ala Pro Pro Gly Gly Arg Gly
225                 230
```

<210> SEQ ID NO 80
<211> LENGTH: 231
<212> TYPE: PRT
<213> ORGANISM: Unknown
<220> FEATURE:
<223> OTHER INFORMATION: Metagenome - beta unit nitrile hydratase - M3aG10

<400> SEQUENCE: 80

```
Met Asp Pro Thr Arg Arg Ser Phe Leu Ala Ser Thr Val Ala Leu Thr
 1               5                  10                  15

Gly Gly Ala Ala Ile Pro Asp Leu Ala His Ala Ala Asp His Asp His
            20                  25                  30

Gln His Gln Asp Leu Pro Ser Asp Leu Ala Leu Arg Val Lys Ser Leu
        35                  40                  45

Glu Ser Leu Leu Val Glu Lys Gly Leu Val Glu Arg Ala Ala Leu Asp
    50                  55                  60

Ala Leu Val Asp Thr Tyr Glu His Lys Val Gly Pro Arg Asn Gly Ala
 65                  70                  75                  80

Arg Val Val Ala Arg Ala Trp Val Asp Pro Asp Tyr Lys Gln Arg Leu
                 85                  90                  95

Phe Ala Asn Gly Thr Ala Ala Val Ala Glu Phe Gly Tyr Ser Gly Ser
            100                 105                 110

Gln Gly Ala Asp Ile Arg Val Val Glu Asn Thr Ala Thr Val His Asn
        115                 120                 125
```

```
Leu Val Val Cys Thr Leu Cys Ser Cys Tyr Pro Trp Pro Val Leu Gly
    130                 135                 140

Leu Pro Pro Val Trp Tyr Lys Ser Ala Pro Tyr Arg Ser Arg Val Val
145                 150                 155                 160

Ile Asp Pro Arg Gly Val Leu Arg Glu Phe Gly Val Val Leu Pro Asp
                165                 170                 175

His Ile Glu Val Arg Val Tyr Asp Ser Thr Ala Glu Gln Arg Tyr Leu
            180                 185                 190

Val Leu Pro Glu Arg Pro Ala Gly Thr Glu Asn Leu Thr Glu Glu Ala
        195                 200                 205

Leu Ala Leu Leu Val Thr Arg Asp Ala Met Ile Gly Val Ala Lys Val
    210                 215                 220

Ala Pro Pro Gly Gly Arg Gly
225                 230

<210> SEQ ID NO 81
<211> LENGTH: 327
<212> TYPE: DNA
<213> ORGANISM: Unknown
<220> FEATURE:
<223> OTHER INFORMATION: Metagenome - p12K unit
<220> FEATURE:
<221> NAME/KEY: CDS
<222> LOCATION: (1)..(327)

<400> SEQUENCE: 81 atg aaa gat agc ccg gtc ttt cgc gag ccg tgg gaa gcg cag gcg ttt      48
Met Lys Asp Ser Pro Val Phe Arg Glu Pro Trp Glu Ala Gln Ala Phe
1               5                   10                  15 gcg ttg gcg atc tcg ttg caa gac cgt ggc gtg ttc acg cga gac gaa      96
Ala Leu Ala Ile Ser Leu Gln Asp Arg Gly Val Phe Thr Arg Asp Glu
                20                  25                  30 tgg gcg gcg gca ctc ggc gat gaa atc aag aag gcg caa gct gcc ggc     144
Trp Ala Ala Ala Leu Gly Asp Glu Ile Lys Lys Ala Gln Ala Ala Gly
            35                  40                  45 gat ccc gat acg ggc gag act tat tac cat cat tgg atg gca gcg ctc     192
Asp Pro Asp Thr Gly Glu Thr Tyr Tyr His His Trp Met Ala Ala Leu
        50                  55                  60 gaa cgg ctg att gca gcc aag ggt gtt gcc gat acg cag acg ctc gcg     240
Glu Arg Leu Ile Ala Ala Lys Gly Val Ala Asp Thr Gln Thr Leu Ala
65                  70                  75                  80 cgc aca cgc gac gcc tgg cag cac gcc tgt gcg cga acg cca cat ggc     288
Arg Thr Arg Asp Ala Trp Gln His Ala Cys Ala Arg Thr Pro His Gly
                85                  90                  95 gcg cca atc gag cta aga ccg gac gac ttc agg aat tga                 327
Ala Pro Ile Glu Leu Arg Pro Asp Asp Phe Arg Asn
                100                 105

<210> SEQ ID NO 82
<211> LENGTH: 108
<212> TYPE: PRT
<213> ORGANISM: Unknown
<220> FEATURE:
<223> OTHER INFORMATION: Metagenome - p12K unit

<400> SEQUENCE: 82

Met Lys Asp Ser Pro Val Phe Arg Glu Pro Trp Glu Ala Gln Ala Phe
1               5                   10                  15

Ala Leu Ala Ile Ser Leu Gln Asp Arg Gly Val Phe Thr Arg Asp Glu
                20                  25                  30
```

```
Trp Ala Ala Ala Leu Gly Asp Glu Ile Lys Lys Ala Gln Ala Ala Gly
        35                  40                  45

Asp Pro Asp Thr Gly Glu Thr Tyr Tyr His His Trp Met Ala Ala Leu
    50                  55                  60

Glu Arg Leu Ile Ala Ala Lys Gly Val Ala Asp Thr Gln Thr Leu Ala
65                  70                  75                  80

Arg Thr Arg Asp Ala Trp Gln His Ala Cys Ala Arg Thr Pro His Gly
                85                  90                  95

Ala Pro Ile Glu Leu Arg Pro Asp Asp Phe Arg Asn
            100                 105
```

<210> SEQ ID NO 83
<211> LENGTH: 321
<212> TYPE: DNA
<213> ORGANISM: Unknown
<220> FEATURE:
<223> OTHER INFORMATION: Metagenome - p12K unit
<220> FEATURE:
<221> NAME/KEY: CDS
<222> LOCATION: (1)..(321)

<400> SEQUENCE: 83

```
atg aga aca gtt gct gag caa atc gcg gct gat ctt gcg agt ccg gcg        48
Met Arg Thr Val Ala Glu Gln Ile Ala Ala Asp Leu Ala Ser Pro Ala
1               5                   10                  15 gcg att ccg cgc cgc aac ggc gag ccg gtc ttc gac gag cct tgg gaa        96
Ala Ile Pro Arg Arg Asn Gly Glu Pro Val Phe Asp Glu Pro Trp Glu
                20                  25                  30 agt cgt gcg ttt ggg ata gcg gtc gcc ctt tcc gag ggt ggc ctc tat       144
Ser Arg Ala Phe Gly Ile Ala Val Ala Leu Ser Glu Gly Gly Leu Tyr
            35                  40                  45 tca tgg gat gaa ttt cgc gat tgc ctg att gct gaa atc aca gcg gcg       192
Ser Trp Asp Glu Phe Arg Asp Cys Leu Ile Ala Glu Ile Thr Ala Ala
        50                  55                  60 gat gcg cgc ggc gag cat acg agc tat tac gaa cgg ttt ctc gcc gcc       240
Asp Ala Arg Gly Glu His Thr Ser Tyr Tyr Glu Arg Phe Leu Ala Ala
65                  70                  75                  80 ctg cag cat ctg ctc gcg gcc aaa cgc ctc tgc act ccc gat gaa gtc       288
Leu Gln His Leu Leu Ala Ala Lys Arg Leu Cys Thr Pro Asp Glu Val
                85                  90                  95 gag cgg cgg atg aac act agc gca ggc acc tga                            321
Glu Arg Arg Met Asn Thr Ser Ala Gly Thr
            100                 105
```

<210> SEQ ID NO 84
<211> LENGTH: 106
<212> TYPE: PRT
<213> ORGANISM: Unknown
<220> FEATURE:
<223> OTHER INFORMATION: Metagenome - p12K unit

<400> SEQUENCE: 84

```
Met Arg Thr Val Ala Glu Gln Ile Ala Ala Asp Leu Ala Ser Pro Ala
1               5                   10                  15

Ala Ile Pro Arg Arg Asn Gly Glu Pro Val Phe Asp Glu Pro Trp Glu
                20                  25                  30

Ser Arg Ala Phe Gly Ile Ala Val Ala Leu Ser Glu Gly Gly Leu Tyr
            35                  40                  45

Ser Trp Asp Glu Phe Arg Asp Cys Leu Ile Ala Glu Ile Thr Ala Ala
        50                  55                  60

Asp Ala Arg Gly Glu His Thr Ser Tyr Tyr Glu Arg Phe Leu Ala Ala
```

```
                    65                   70                  75                  80
Leu Gln His Leu Leu Ala Ala Lys Arg Leu Cys Thr Pro Asp Glu Val
                85                  90                  95

Glu Arg Arg Met Asn Thr Ser Ala Gly Thr
            100                 105

<210> SEQ ID NO 85
<211> LENGTH: 426
<212> TYPE: DNA
<213> ORGANISM: Unknown
<220> FEATURE:
<223> OTHER INFORMATION: Metagenome - p12K unit
<220> FEATURE:
<221> NAME/KEY: CDS
<222> LOCATION: (1)..(426)

<400> SEQUENCE: 85 atg aca acc ttg agc cag cgt gaa gcg gcc ccc tcg gcc gag ctt ctt      48
Met Thr Thr Leu Ser Gln Arg Glu Ala Ala Pro Ser Ala Glu Leu Leu
1               5                   10                  15 gac cta ccg caa ctt cca agc gac acc gac ggc ccc gtc ttc gcg gaa      96
Asp Leu Pro Gln Leu Pro Ser Asp Thr Asp Gly Pro Val Phe Ala Glu
                20                  25                  30 cct tgg gaa gcg gaa gcg ttt gcg ctt gcc gta agt ctt tca gag caa     144
Pro Trp Glu Ala Glu Ala Phe Ala Leu Ala Val Ser Leu Ser Glu Gln
            35                  40                  45 gga cat ttc acg tgg aag gaa tgg gca gca acg ctc gcc gat gaa ctg     192
Gly His Phe Thr Trp Lys Glu Trp Ala Ala Thr Leu Ala Asp Glu Leu
        50                  55                  60 gag ggc gcc gcc aat cgc ggc gag ccg gat gac ggt acg cat tat tat     240
Glu Gly Ala Ala Asn Arg Gly Glu Pro Asp Asp Gly Thr His Tyr Tyr
65                  70                  75                  80 gag tac tgg ctg acg gcc ctg gaa agg ctg gtt acg atc aag ggc ctg     288
Glu Tyr Trp Leu Thr Ala Leu Glu Arg Leu Val Thr Ile Lys Gly Leu
                85                  90                  95 aca gat cag caa gcg atg cgc gag cgc aaa gag gcg tgg gaa gaa gcc     336
Thr Asp Gln Gln Ala Met Arg Glu Arg Lys Glu Ala Trp Glu Glu Ala
            100                 105                 110 tat cgc cat acc ccg cat ggc gcg cca gtt gaa ctt atg tct ccg ctc     384
Tyr Arg His Thr Pro His Gly Ala Pro Val Glu Leu Met Ser Pro Leu
        115                 120                 125 gat caa agc cgg ata gcc gaa gag gac agc gaa tcc tca tag             426
Asp Gln Ser Arg Ile Ala Glu Glu Asp Ser Glu Ser Ser
    130                 135                 140

<210> SEQ ID NO 86
<211> LENGTH: 141
<212> TYPE: PRT
<213> ORGANISM: Unknown
<220> FEATURE:
<223> OTHER INFORMATION: Metagenome - p12K unit

<400> SEQUENCE: 86

Met Thr Thr Leu Ser Gln Arg Glu Ala Ala Pro Ser Ala Glu Leu Leu
1               5                   10                  15

Asp Leu Pro Gln Leu Pro Ser Asp Thr Asp Gly Pro Val Phe Ala Glu
                20                  25                  30

Pro Trp Glu Ala Glu Ala Phe Ala Leu Ala Val Ser Leu Ser Glu Gln
            35                  40                  45

Gly His Phe Thr Trp Lys Glu Trp Ala Ala Thr Leu Ala Asp Glu Leu
        50                  55                  60
```

-continued

```
Glu Gly Ala Ala Asn Arg Gly Glu Pro Asp Asp Gly Thr His Tyr Tyr
 65              70                  75                  80

Glu Tyr Trp Leu Thr Ala Leu Glu Arg Leu Val Thr Ile Lys Gly Leu
             85                  90                  95

Thr Asp Gln Gln Ala Met Arg Glu Arg Lys Glu Ala Trp Glu Glu Ala
            100                 105                 110

Tyr Arg His Thr Pro His Gly Ala Pro Val Glu Leu Met Ser Pro Leu
        115                 120                 125

Asp Gln Ser Arg Ile Ala Glu Glu Asp Ser Glu Ser Ser
        130             135                 140
```